US009862930B2

(12) United States Patent
Dowdy et al.

(10) Patent No.: US 9,862,930 B2

(45) Date of Patent: Jan. 9, 2018

(54) GENERATION OF HUMAN IPS CELLS BY A SYNTHETIC SELF-REPLICATIVE RNA

(71) Applicant: The Regents of the University of California, Oakland, CA (US)

(72) Inventors: Steven F. Dowdy, La Jolla, CA (US); Naohisa Yoshioka, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 89 days.

(21) Appl. No.: 14/402,924

(22) PCT Filed: May 21, 2013

(86) PCT No.: PCT/US2013/041980

§ 371 (c)(1),
(2) Date: Nov. 21, 2014

(87) PCT Pub. No.: WO2013/177133

PCT Pub. Date: Nov. 28, 2013

(65) Prior Publication Data

US 2015/0159143 A1 Jun. 11, 2015

Related U.S. Application Data

(60) Provisional application No. 61/649,876, filed on May 21, 2012, provisional application No. 61/798,229, filed on Mar. 15, 2013.

(51) Int. Cl.

| | |
|---|---|
| ***C12N 5/074*** | (2010.01) |
| ***G01N 33/569*** | (2006.01) |
| ***C07K 14/47*** | (2006.01) |
| ***C12N 9/12*** | (2006.01) |
| ***C12N 15/86*** | (2006.01) |

(52) U.S. Cl.

CPC ........ *C12N 5/0696* (2013.01); *C07K 14/4702* (2013.01); *C07K 14/4705* (2013.01); *C12N 9/127* (2013.01); *C12N 15/86* (2013.01); *G01N 33/56966* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2506/1307* (2013.01); *C12N 2770/36122* (2013.01); *C12N 2770/36143* (2013.01); *C12N 2840/206* (2013.01)

(58) Field of Classification Search

CPC ...... C12N 5/0696; C12N 9/127; C12N 15/86; C12N 2501/60; C12N 2501/602; C12N 2501/603; C12N 2501/604; C12N 2501/605; C12N 2501/606; C12N 2506/1307; C12N 2770/36122; C12N 2770/36143; C12N 2840/206; C07K 14/4702; C07K 14/4705; G01N 33/56966

See application file for complete search history.

(56) References Cited

U.S. PATENT DOCUMENTS

| | | | |
|---|---|---|---|
| 6,583,121 | B1 | 6/2003 | Johnston et al. |
| 2006/0198854 | A1 | 9/2006 | Pushko |
| 2006/0292175 | A1 | 12/2006 | Polo et al. |
| 2011/0061118 | A1 | 3/2011 | Kuhn et al. |
| 2011/0065103 | A1 | 3/2011 | Sahin et al. |

FOREIGN PATENT DOCUMENTS

| | | | | |
|---|---|---|---|---|
| EP | 1 386 926 A1 | | 2/2004 | |
| WO | 97/38087 A2 | | 10/1997 | |
| WO | 2005/116192 A2 | | 12/2005 | |
| WO | 2009/067563 A1 | | 5/2009 | |
| WO | WO 2009093022 A2 | * | 7/2009 | ........... C12N 5/0695 |
| WO | WO 2009152529 A2 | * | 12/2009 | ......... A01K 67/0271 |
| WO | 2010028019 A2 | | 3/2010 | |
| WO | 2010/098419 A1 | | 9/2010 | |
| WO | WO 2010098419 A1 | * | 9/2010 | ........... C12N 5/0696 |
| WO | 2010118244 A1 | | 10/2010 | |
| WO | WO 2011109612 A2 | * | 9/2011 | ........... C12N 5/0696 |
| WO | 2014/072061 A1 | | 5/2014 | |

OTHER PUBLICATIONS

Smerdou et al., Current Opinion in Molecular Therapeutics, 1(2): 244-251, 1999.*

Liu et al., Cell Stem Cell, 3: 587-590, 2008.*

Clark et al., Stem Cells, 22(2): 169-179, 2004.*

Stevanovic et al., Mammalian Genome, 5: 640-642, 1994.*

Maekawa et al., Nature, 474: 225-229, 2011.*

Sommer, C.A. et al., "Induced Pluripotent Stem Cell Generation Using a Single Lentiviral Stem Cell Cassette", Stem Cells, Mar. 2009, vol. 27, pp. 543-549.

Sommer, C.A. et al., "Generation of Transgene-Free Lung Disease-Specific Human Induced Pluripotent Stem Cells Using a Single Excisable Lentiviral Stem Cell Cassette", Stem Cells, Oct. 2010, vol. 28, No. 10, pp. 1728-1740, Sep. 15, 2016.

Strauss, J.H. et al., "The alphaviruses: gene expression, replication, and evolution", Microbiological Reviews, Sep. 1994, pp. 491-562.

Zhenling Luo, Written Opinion and Search Report, Singapore Patent Application No. 11201407595U, Singapore Patent Office, dated Nov. 12, 2015.

Ban, Hiroshi et al, "Efficient generation of transgene-free human induced pluripotent stem cells (iPSCs) by temperature-sensitive Sendai virus vectors", PNAS, vol. 108, No. 34, Aug. 23, 2011, pp. 14234-14239.

Offermann, Stefanie, Extended European Search Report, EP Patent Application No. 13794196.9, dated Nov. 24, 2015.

Wiley, Luke A. et al., "Patient-specific induced pluripotent stem cells (iPSCs) for the study and treatment of retinal degenerative diseases", Progress in Retinal and Eye Research, vol. 44, Nov. 4, 2014, pp. 15-35.

Yoshioka, Naohisa et al., "Efficient Generation of Human iPSCs by a Synthetic Self-Replicative RNA", Cell Stem Cell, vol. 13, No. 2, Aug. 1, 2013, pp. 246-254.

(Continued)

*Primary Examiner* — Thaian N Ton

(74) *Attorney, Agent, or Firm* — Gavrilovich, Dodd & Lindsey LLP

(57) ABSTRACT

The disclosure provides methods and compositions useful for obtaining induced stem cells, methods of making and use thereof.

23 Claims, 14 Drawing Sheets

(56) References Cited

OTHER PUBLICATIONS

Becamel, Philippe, International Preliminary Report on Patentability and Written Opinion, International Application No. PCT/US2013/041980, dated Dec. 4, 2014.
Heo, Joo Hyung, International Search Report and Written Opinion, International Application No. PCT/US2013/041980, dated Jan. 27, 2014.
Nishimura, Ken et al., "Persistent and stable gene expression by a cytoplasmic RNA replicon based on a noncytopathic variant Sendai virus," The Journal of biological chemistry, Sep. 14, 2007, vol. 282, No. 37, pp. 27383-27391.
Fera Goh, Written Opinion, Patent Application No. 11201407595U, Intellectual Property Office of Singapore, dated Dec. 8, 2016.
Stadtfeld M. et al., "Induced pluripotent stem cells generated without viral integration", Science, Nov. 7, 2008, vol. 322, No. 5903, pp. 945-949.
Angel et al., "Innate Immune Suppression Enables Frequent Transfection with RNA Encoding Reprogramming Proteins", Plos One, Jul. 23, 2010, vol. 5, Issue 7, e1175.
Kamrud et al., "Alphavirus replicon approach to promoterless analysis of IRES elements", Virology, 360, 2007, pp. 376-387.
Perri et al., "Replicon Vectors Derived from Sindbis Virus and Semliki Forest Virus That Establish Persistent Replication in Host Cells", Journal of Virology, Oct. 2000, vol. 74, No. 20, pp. 9802-9807.
Petrakova et al., "Noncytopathic Replication of Venezuelan Equine Encephalitis Virus and Eastern Equine Encephalitis Virus Replicons in Mammalian Cells", Journal of Virology, Jun. 2005, vol. 79, No. 12, pp. 7597-7608.
Warren et al., "Highly Efficient Reprogramming to Pluripotency and Directed Differentiation of Human Cells with Synthetic Modified mRNA", Cell Stem Cell, Nov. 5, 2010, 7, pp. 618-630.
Xiong et al., "Sindbis Virus: An Efficient, Broad Host Range Vector for Gene Expression in Animal Cells", Science, 1989, vol. 243, pp. 1188-1191.

* cited by examiner

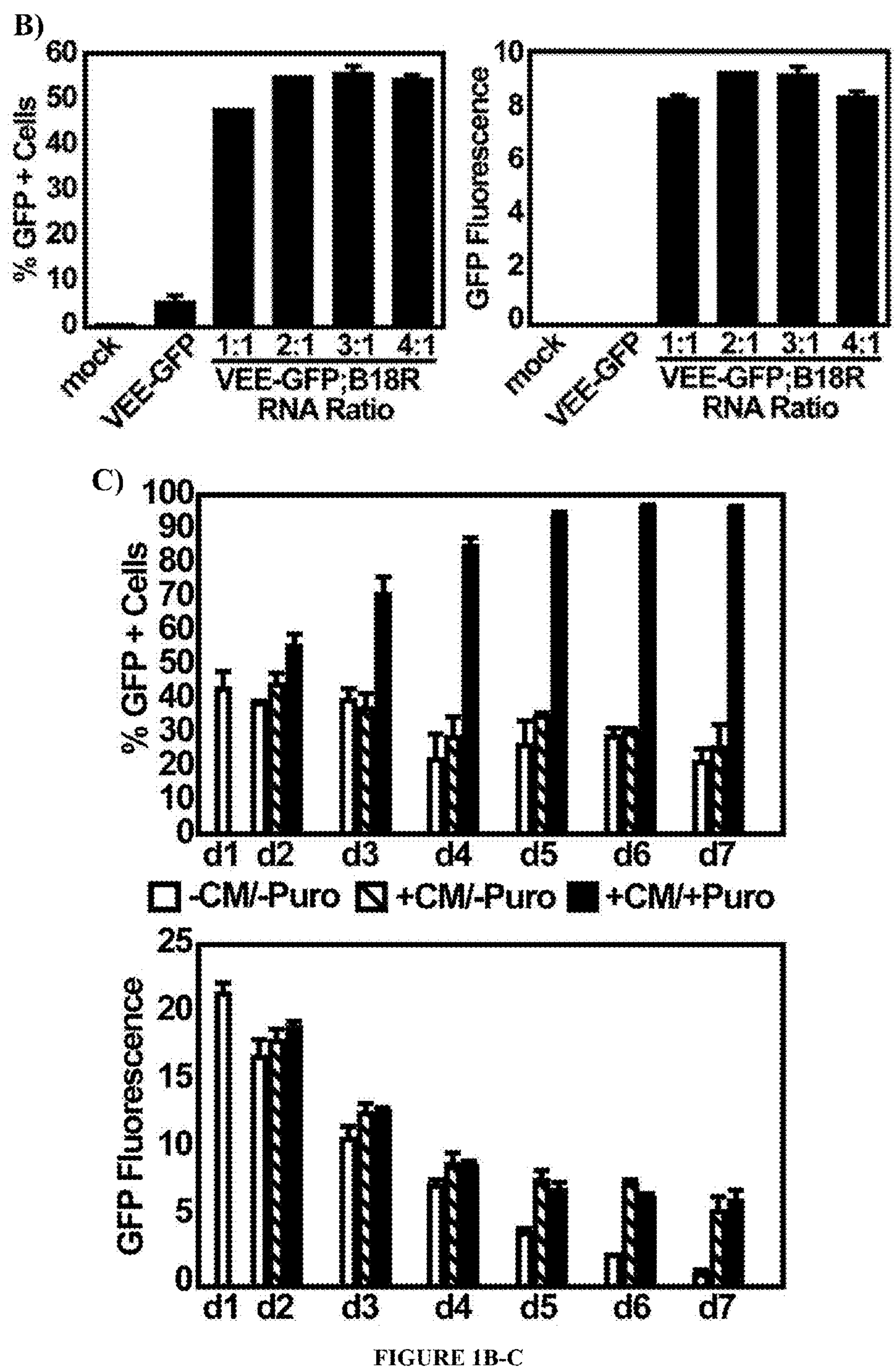
FIGURE 1B-C

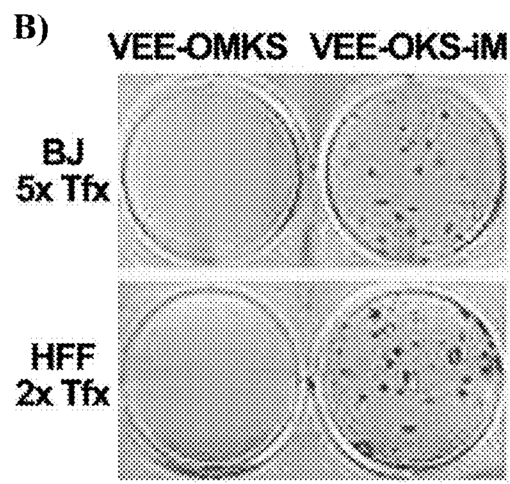
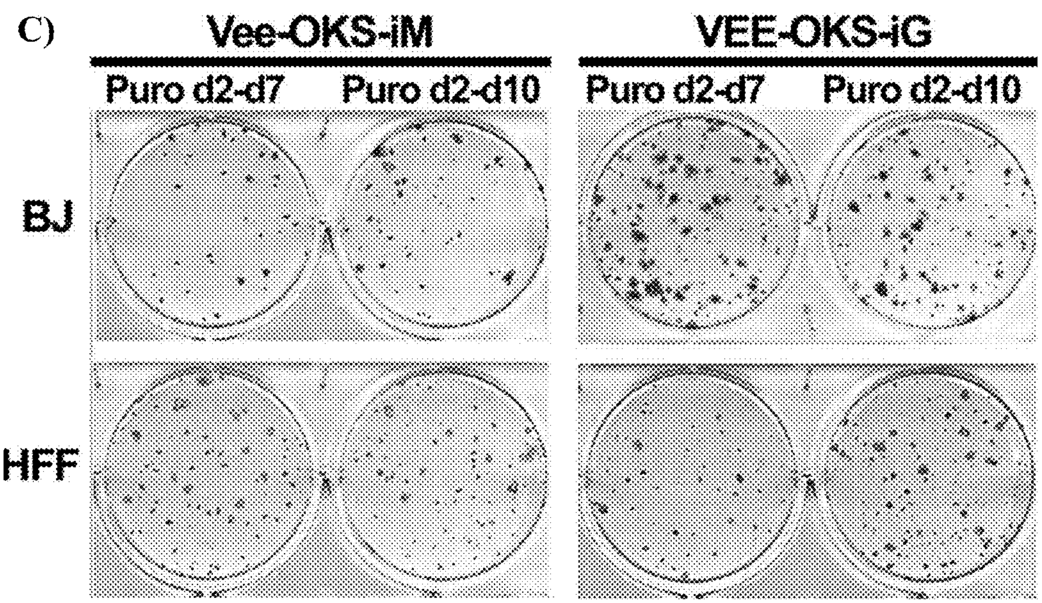
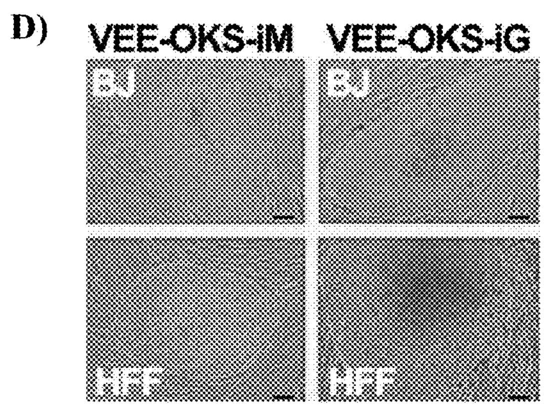
FIGURE 2B-D

C)

D)
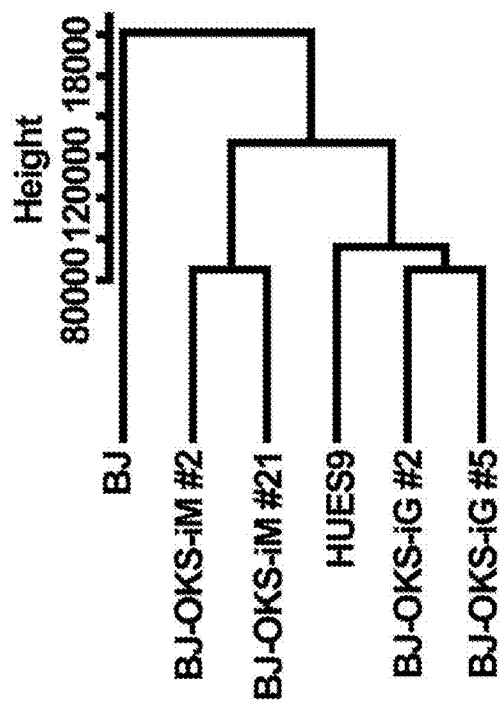
E)
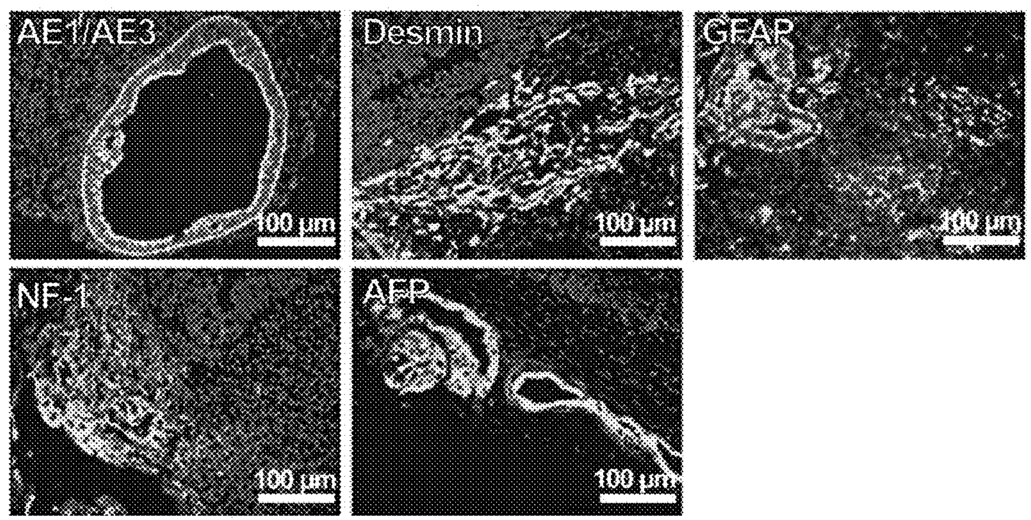
FIGURE 3D-E

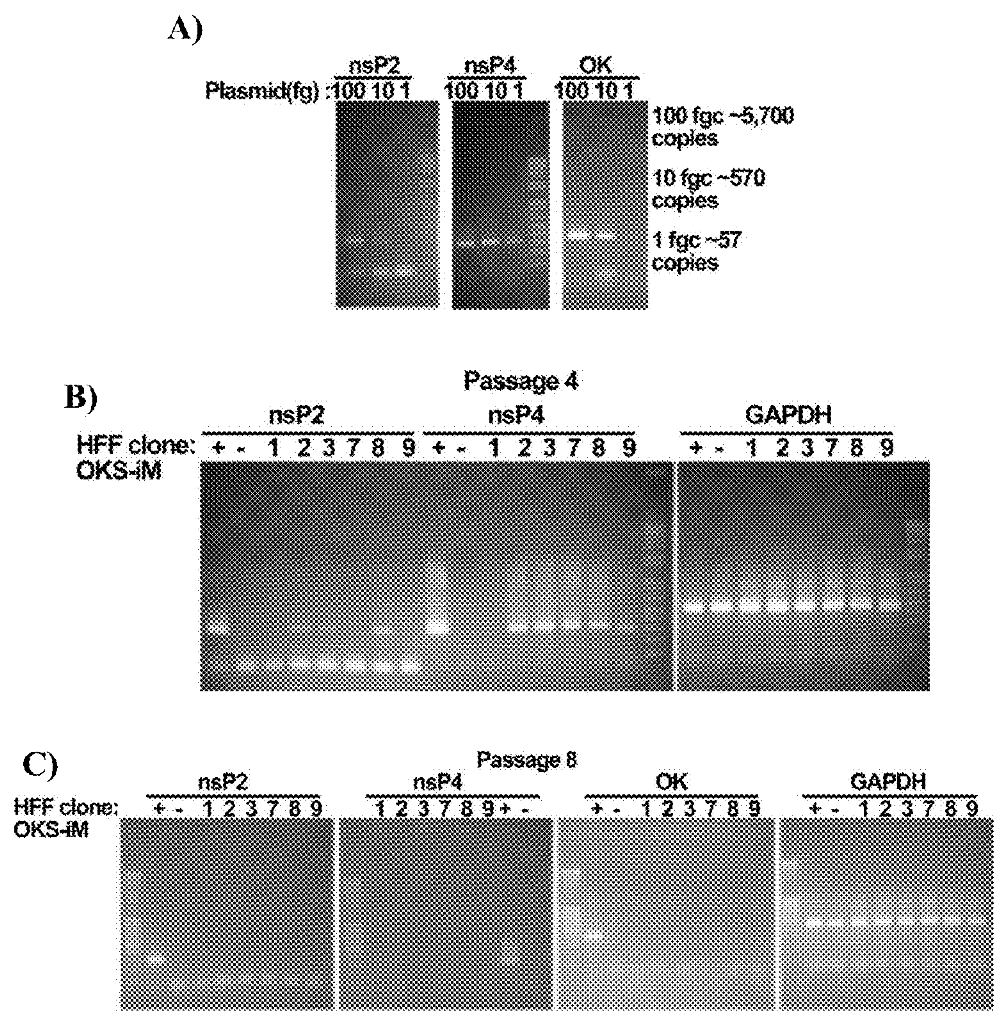
FIGURE 4A-C

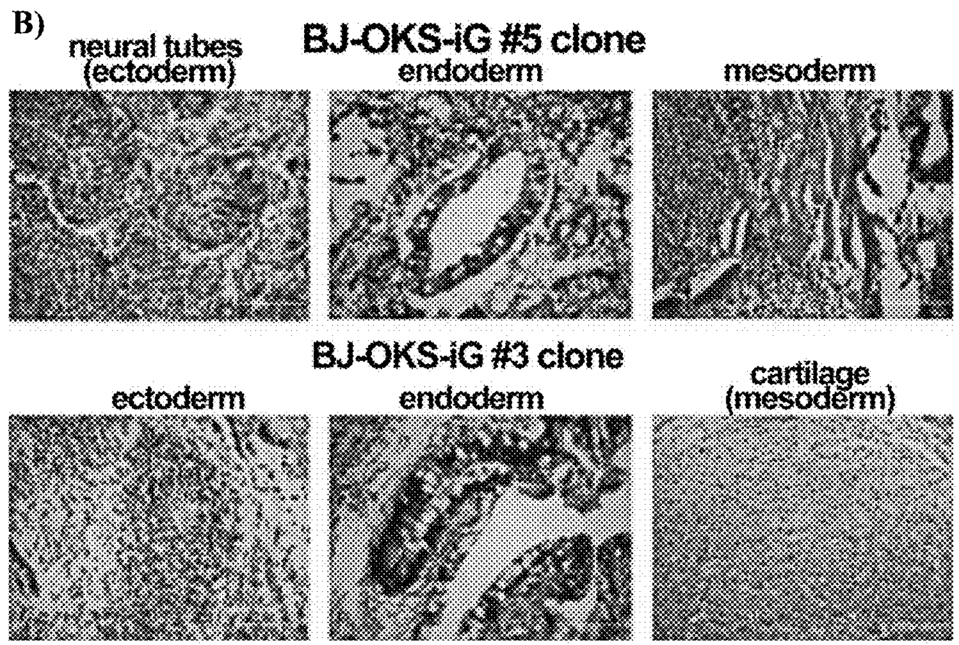
FIGURE 6B
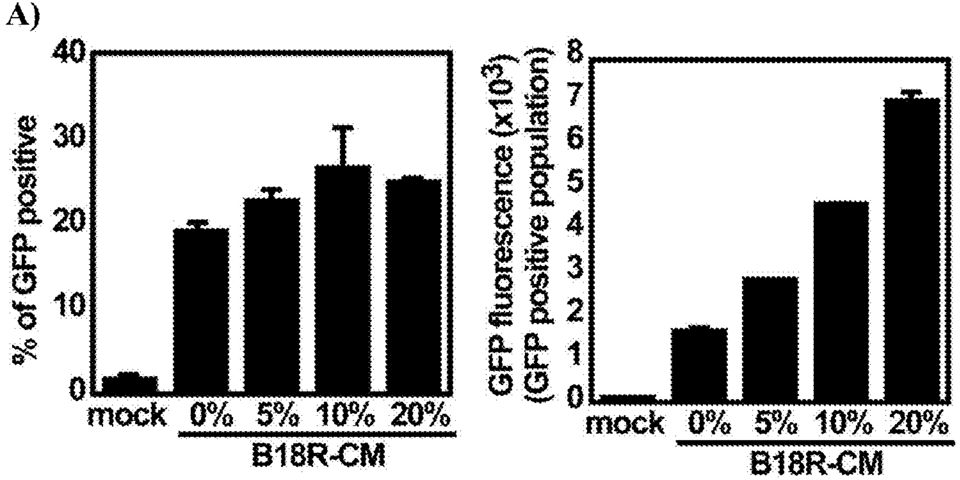
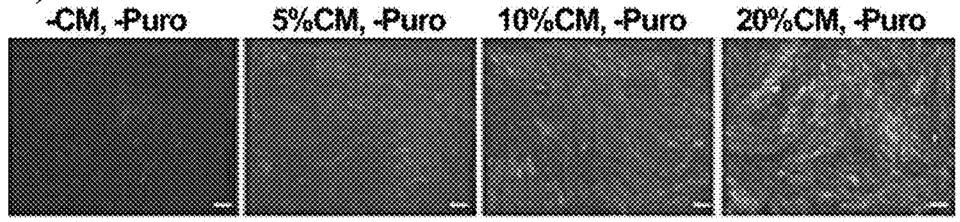
FIGURE 7A-B

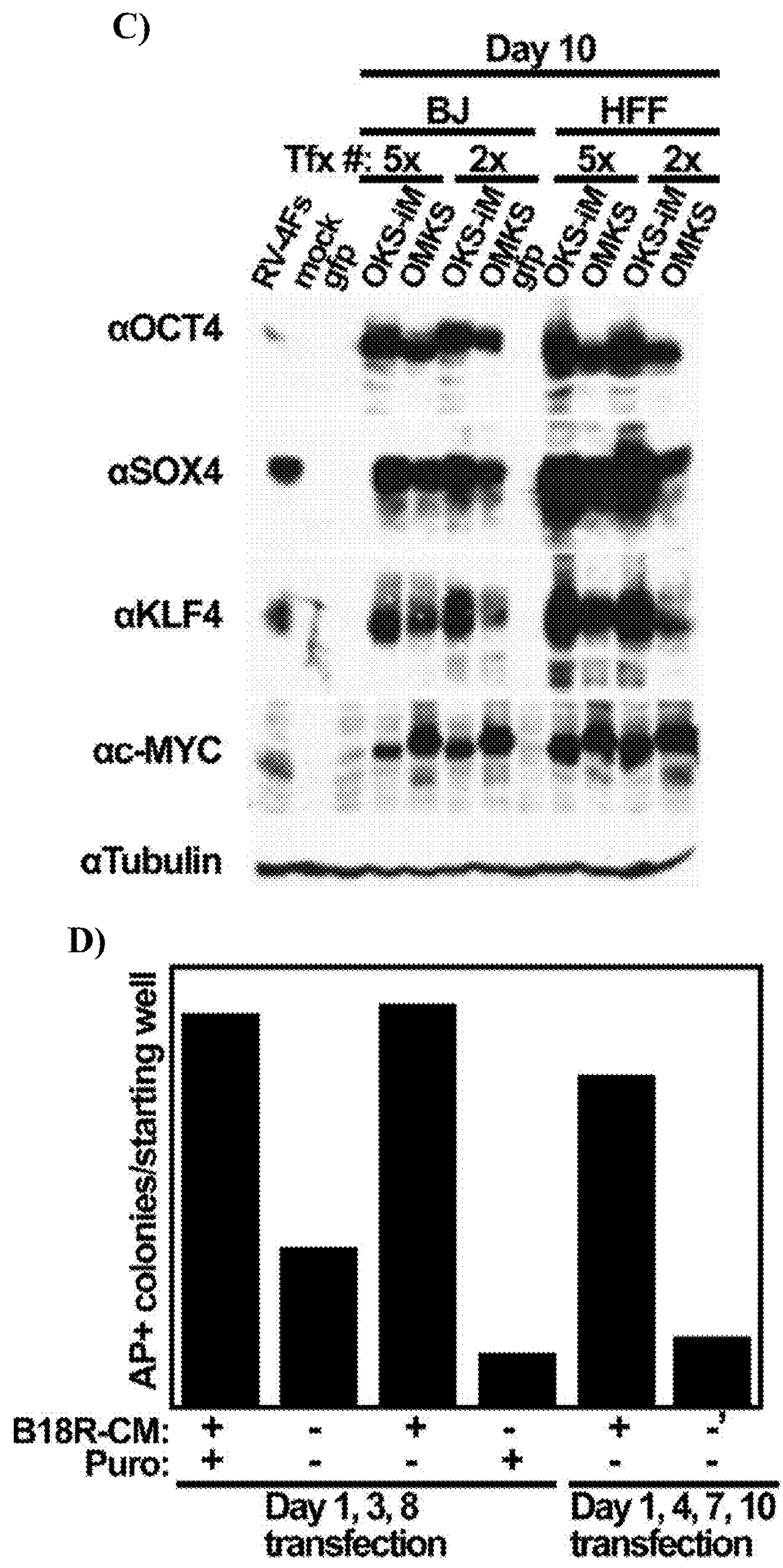
FIGURE 7C-D

GENERATION OF HUMAN IPS CELLS BY A SYNTHETIC SELF-REPLICATIVE RNA

CROSS REFERENCE TO RELATED APPLICATION

This application is a U.S. National Stage Application filed under 35 U.S.C. §371 and claims priority to International Application No. PCT/US2013/041980, filed May 21, 2013, which application claims priority to U.S. Provisional Application Ser. No. 61/649,876, filed May 21, 2012 and 61/798,229, filed Mar. 15, 2013, each of which are hereby incorporated by reference in their entirety.

TECHNICAL FIELD

Provided are methods and compositions useful for producing and propagating stem cells from fibroblasts. The disclosure relates to the production of induced pluripotent stem cells (iPS) and methods of use thereof.

BACKGROUND

Stems cells are a potential source from which organs may be regenerated, tissues may be repaired, biological factors prepared or delivered and disease or disorders treated.

SUMMARY

Generation of induced Pluripotent Stem (iPS) cells from patients is important to use stem cells therapeutically. Generation of iPS cells requires expression of several pluripotent transcription factors or Reprogramming Factors (RFs), including Oct4, Sox2, Klf4, cMyc, Glis1 (and potentially Nanog and Lin28). However, due to concerns with integration of DNA vectors (viruses and naked DNA) into the genome during iPS cell generation excludes these approaches from being subsequently used in patients.

The disclosure describes an approach to generate induced Pluripotent Stem (iPS) cells by ectopically expressing RFs using a synthetic self-replicating RNA from a modified alphavirus (e.g., Venezuelan Equine Encephalitis (VEE) virus). The alphavirus was designed to express, in one embodiment, four RFs that resulted in the following advantages over mRNA transfection approaches: 1) utilized a single RNA species capable of self-replicating for a limited number cell divisions, thereby reducing the number of transfections; 2) is capable of encoding at one, two, three, four, or more RF open reading frames (ORFs); and 3) consistently expressed all the RF genes at high threshold levels over multiple cellular divisions. By using the self-replicating backbone of an alphavirus (the structural genes being removed) to express the RFs requires only 3 to 4 transfections (and even only 1 or 2) into primary human fibroblasts to generate iPS cells. The generation of the alphavirus RF-RNA transcript utilizes a SP6 (or T7) in vitro transcription kit that does not require special conditions and thereby, further simplifies the approach for broad use. By expressing the four RFs at consistent, high levels over time in the same cell combined with replication of the alphavirus-RF RNA for a limited number of multiple cell generations, the alphavirus-RF RNA approach solves both of the major inefficiency problems associated with attempting to generate iPS cells by daily repeated daily transfections for >14 days of four individual RF mRNAs. The alphavirus-RF RNA is an ectopic approach that does not utilize a DNA intermediate and therefore, there is no opportunity for integrative mutation that can occur with DNA vector-based iPS cell approaches. Moreover, the timing of RNA replicon loss by degradation can be regulated by B18R withdrawal from the media. Using this approach, >100 independent iPS cell clones were generated from both OCT4/KLF4/SOX2/c-MYC and OCT4/KLF4/SOX2/GLIS1 alphavirus-RF RNA protocols from two independent parental human fibroblast populations. In addition, the approach can be engineered to express alternative RF combinations and/or insertion of additional RF ORFS into the RF-RNA backbone for refining iPS cell generation from specific cell types or for use in driving transdifferentiation.

The disclosure provides an alphavirus replicon RNA comprising at least one non-structural replicase domain from an alphavirus and at least one non-alphavirus heterologous sequence encoding factors for inducing the generation of pluripotent stem cells when expressed in a somatic cell. In one embodiment, the replicon comprises sequences obtained from an alphavirus selected from the group consisting of Eastern Equine Encephalitis virus (EEE), Venezuelan Equine Encephalitis virus (VEE), Everglades virus, Mucambo virus, Pixuna virus and Western Equine Encephalitis virus (WEE). In another embodiment, the replicon comprises sequences obtained from an alphavirus selected from the group consisting of Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus. In yet another embodiment, the at least one non-alphavirus heterologous sequence comprises at least 2, 3, 4 or 5 non-alphavirus heterologous sequences. In yet another embodiment, of any of the foregoing the non-alphavirus heterologous sequence is selected from a polynucleotide encoding a KLF polypeptide, a SOX-2 polypeptide, a OCT-3/4 polypeptide, a c-MYC or n-MYC or L-MYC polypeptide, a GLIS1 polypeptide, a NANOG polypeptide and any combination thereof. In a further embodiment, the polynucleotide encoding the KLF polypeptide encodes a KLF polypeptide having at least 95% identity to a sequence of SEQ ID NO:8. In another embodiment, the polynucleotide encoding the KLF polypeptide encodes a KLF polypeptide having a sequence of SEQ ID NO:8. In yet another embodiment, the polynucleotide encoding the KLF polypeptide comprises a sequence as set forth in SEQ ID NO:7, wherein "T" is "U". In another embodiment, the polynucleotide encoding the SOX-2 polypeptide encodes a SOX-2 polypeptide having at least 95% identity to a sequence of SEQ ID NO:6. In another embodiment, the polynucleotide encoding the SOX-2 polypeptide encodes a SOX-2 polypeptide having a sequence of SEQ ID NO:6. In yet another embodiment, the polynucleotide encoding the Sox-2 polypeptide comprises a sequence as set forth in SEQ ID NO:5, wherein "T" is "U". In another embodiment, the polynucleotide encoding the OCT-4 polypeptide encodes a OCT-4 polypeptide having at least 95% identity to a sequence of SEQ ID NO:4. In a further embodiment, the polynucleotide encoding the OCT-4 polypeptide encodes a OCT-4 polypeptide having a sequence of SEQ ID NO:4. In a further embodiment, the polynucleotide encoding the OCT-4 polypeptide comprises a sequence as set forth in SEQ ID NO:3, wherein "T" is "U". In another embodiment, the polynucleotide encoding the c-MYC polypeptide encodes a c-MYC polypeptide having at least 95% identity to a sequence of SEQ ID NO:10. In a further embodiment, the polynucleotide encoding the c-MYC polypeptide encodes a c-MYC polypeptide having a sequence of SEQ ID NO:10. In yet a further embodiment, the polynucleotide encoding the c-MYC polypeptide comprises a sequence as set forth in SEQ ID NO:9, wherein "T" is "U". In another embodiment, the polynucleotide encoding the GLIS1 polypeptide encodes a GLIS1 polypeptide having at least 95% identity to a sequence of SEQ ID NO:34. In a further embodiment, the polynucleotide encoding the GLIS1 polypeptide encodes a GLIS1 polypeptide having a sequence of SEQ ID NO:34. In yet a further embodiment, the polynucleotide encoding the GLIS1 polypeptide comprises a sequence as set forth in SEQ ID NO:33, wherein "T" is "U". In another embodiment, the polynucleotide encoding the NANOG polypeptide encodes a NANOG polypeptide having at least 95% identity to a sequence of SEQ ID NO:2. In a further embodiment, the polynucleotide encoding the NANOG polypeptide encodes a NANOG polypeptide having a sequence of SEQ ID NO:2. In yet a further embodiment, the polynucleotide encoding the NANOG polypeptide comprises a sequence as set forth in SEQ ID NO:1, wherein "T" is "U". In one embodiment of any of the foregoing, the replicon comprises from 5' to 3': (VEE RNA replicases)-(promoter)-($RF_1$)-(self cleaving peptide)-($RF_2$)-(self cleaving peptide)-($RF_3$)-(IRES or core promoter)-($RF_4$)-(IRES or optional promoter)-(optional selectable marker)-(VEE 3'UTR and polyA tail)-(optional selectable marker)-promoter; wherein $RF_{1-4}$ are factors that induce de-differentiation of a somatic cell to a pluripotent cells, wherein $RF_{2-3}$ are optional, $RF_{3-4}$ are optional, or $RF_4$ is optional; wherein $RF_{1-4}$ are selected from the group consisting of Oct-4, Klf4, Sox-2, c-Myc, Nanog, and Glis1. In another embodiment, the replicon comprise a sequence that is 90%, 95%, 98%, 99% or 100% identical to SEQ ID NO:29, 30, 31, or 32 from about position 1 to about position 7561 wherein "T" of the sequence is substituted with "U", followed by one or more RFs, followed by a 3'UTR and polyA tail, wherein the one or more RFs are selected from the group consisting of Oct-3/4, Sox-2, Klf4, c-Myc, Nanog, and Glis1; wherein when more than one RF is present, the coding sequences may be separated by an internal ribosome entry site (IRES) or a small promoter. In a further embodiment, the replicon comprise a sequence that is at least 95%, 98%, 99% or 100% identical to a sequence selected from the group consisting of SEQ ID NO:29, 30, 31, or 32, wherein "T" is "U".

The disclosure also provides a composition comprising human cells transformed with a replicon as described in any of the foregoing embodiments and embodiments further described herein. In one embodiment, the composition further comprises B18R conditioned media. In another embodiment, the human cells are somatic cells. In a further embodiment, the human cells are fibroblasts.

The disclosure also provides a method of making stem cells comprising culturing the composition described above and elsewhere herein, for at least 30 days under conditions to express the coding sequences of the replicon and isolating stem cells.

The disclosure also provides a method of making stem cells comprising transforming somatic cells with a replicon of the disclosure, culturing the somatic cells under conditions to promote expression of the replicon and isolating stem cells. In one embodiment, the culturing comprise culturing the cells in media conditioned with B18R. In another embodiment, the B18R conditioned media is produced by transfection of B18R mRNA into primary human fibroblasts.

The disclosure also provides isolated stem cells obtained from the methods described herein, wherein the stem cells are retroviral DNA- or RNA-free.

The disclosure also provides a method comprising contacting a human somatic cell with an ectopic self-replicating RNA replicon comprising polynucleotides encoding at least four de-differentiation factors selected from the group consisting of a (i) KLF4, (ii) OCT4, (iii) SOX2, (iv) c-MYC or n-MYC or L-MYC, (v) GLIS1 and (vi) NANOG; culturing the somatic cell to express the de-differentiation factor; selecting cells that display a stem cell morphology and/or stem cell markers; and subculturing the cells to obtain a population of induced stem cells. In one embodiment, the cells are selected by detecting expression of a Tumor Rejection Antigen 1-60 and/or 1-81.

The disclosure also provides a vector system for producing human stem cells, comprising at least one self-replicating RNA replicon comprising one or more polynucleotides encoding de-differentiation factors selected from the group consisting of a KLF4, OCT4, SOX2, c-MYC or n-MYC or L-MYC, GLIS1, and NANOG. In one embodiment, the replicon comprises (a) Oct4, Sox2, Klf4, and c-Myc, or (b) Oct4, Sox2, Klf4, and Glis1. In another embodiment, the at least one self-replicating RNA vector is derived from an alphavirus. In a further embodiment, the alphavirus is VEE.

The disclosure also provides an isolated human somatic cell comprising an ectopic RNA replicon comprising one or more de-differentiation polynucleotide sequences. In a further embodiment, wherein upon culture conditions to express the de-differentiation polynucleotides in the ectopic RNA replicon, the somatic cell de-differentiates.

The disclosure also provides a cell population comprising the human somatic cell containing an ectopic RNA replicon comprising one or more de-differentiation polynucleotide sequences.

The disclosure also provides a cell population obtained by contacting a human somatic cell with an ectopic self-replicating RNA replicon comprising polynucleotides encoding at least four de-differentiation factors selected from the group consisting of a (i) KLF4, (ii) OCT4, (iii) SOX2, (iv) c-MYC or n-MYC or L-MYC, (v) GLIS1 and (vi) NANOG; culturing the somatic cell to express the de-differentiation factor; selecting cells that display a stem cell morphology and/or stem cell markers; and subculturing the cells to obtain a population of induced stem cells. In one embodiment, the cells are selected by detecting expression of a Tumor Rejection Antigen 1-60 and/or 1-81.

The disclosure also provides a recombinant human fibroblast cells containing an ectopic RNA molecule encoding B18R. In one embodiment, the RNA encoding B18R comprise SEQ ID NO:39, wherein "T" is replaced with "U". In another embodiment, the RNA encodes a polypeptide comprising the sequence set forth in SEQ ID NO:40.

The disclosure also provides a method of making B18R conditioned media comprising culturing a human fibroblast cell transformed with RNA encoding B18R under conditions that allow expression of B18R and isolating media from the culture.

DESCRIPTION OF THE FIGURES

FIG. 1A-E shows construction and Persistence of Synthetic VEE-RF RNA Replicons in Primary Human Fibroblasts. (A) Schematic of VEE-RF RNA replicon. 5' end nsP1-4: non-structural proteins1-4; 3' end C, E2, E1: Structural proteins. Locations of 26S internal promoter, ribosome shifting 2A peptide, IRES sequence, Puromycin (Puro)

Figure 1A:
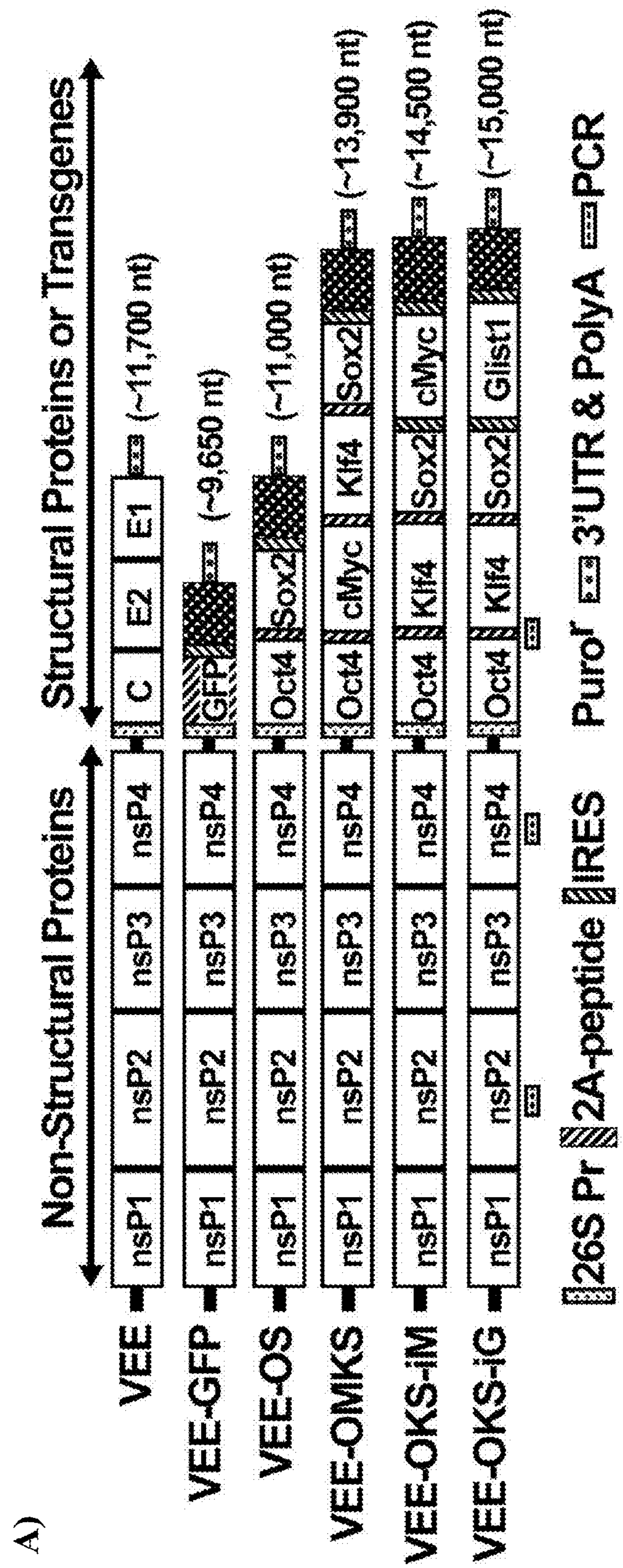

resistance gene and the regions for PCR detections of replicon as indicated. (B) Co-transfection of B18R mRNA with VEE RNA replicon enables to express VEE-GFP on day 1. (C) B18R Conditioned Media (B18R-CM) and puromycin selection are required for persistence of VEE-GFP RNA over 7 days. (D) B18R-CM and puromycin are required for retention of VEE-GFP RNA. Photographs of GFP expression on day 7 as indicated. Bar, 200 μm. (E) Immunoblot analysis of VEE RNA expressed reprogramming factors expressed in HFFs cells on day 1 versus retrovirus (RV-4Fs) expression.

FIG. 2A-E shows generation of iPS cells by VEE-RF RNA. (A) Schematic of epigenetic VEE-RF RNA iPS cell generation protocol. Human fibroblasts were plated on day 0 (d0) and co-transfected (Tfx) with VEE-RF RNA replicon plus B18R mRNA (3:1 ratio) on day 1 (confluent, ~$4\times10^5$ cells) and treated with puromycin until day 7 (or 10) as indicated. Cells were cultured in B18R-CM until iPS cell colonies were isolated on day 25-30. (B) iPS cell colonies stained with Alkaline Phosphatase were generated with VEE-OKS-iM RNA, but not VEE-OMKS RNA. (C) Alkaline Phosphatase staining of iPS cell colonies generated from BJ or HFFs from d1, 4, 7, 10 transfection protocol as indicated. (D) Typical images of iPS cell colonies on day 26 by VEE-OKS-iM RNA and day 22 for VEE-OKS-iG RNA from BJ or HFFs fibroblasts as indicated. Bar, 100 μm. (E) Immunohistochemistry staining of pluripotent ES marker genes in isolated iPS cell clones generated as indicated. Similar results obtained for 26 additional iPS cell clones (30 clones total). Bar, 100 μm; insert, 10× amplification.

FIG. 3A-E shows characterization of VEE-RF RNA iPS Cell Clones. (A) Expression of ES maker genes by qRT-RCR analysis of BJ and HFF VEE-OKS-iM iPS clones as indicated. (B) DNA methylation analysis of NANOG and OCT4 promoter regions. Solid circle, methylated; Open circle, demethylated. Top numbers indicate CpG number relative to the transcription start site. (C) Genome-wide mRNA sequence profile scatter plot analysis of BJ-OKS-iM #2 and BJ-OKS-iG #5 compared to parental human BJ fibroblasts and human HUES9 embryonic stem cells with pluripotency NANOG, OCT4, SOX2 indicated. (D) Unsupervised hierarchical dendrogram of genome-wide RNA sequences analysis showing clustering of four independent iPS cell clones with HUES9 compared to BJ fibroblasts. (E) Teratoma formation of BJ-OKS-iM #21 clone in nude mice. AE1/AE3 (cytokeratin), NF-1 (neuronal cells) and GFAP (neuronal cells) used for markers of ectoderm; Desmin (muscle cells) used for marker of mesoderm; and AFP (primitive and definitive endoderm) used for marker of endoderm. Bar, 100 μm.

FIG. 4 shows RT-PCR analysis for checking up the existence of RNA replicon. Measurement of PCR sensitivity with the plasmid of OKS-iM-RNA replicon. PCRs for nsP2, nsP4 and OCT4-T2A-KLF4 (OK) regions were performed with 100, 10 and 1 fg of plasmid (Top Panel). RT-PCR of HFF-OKS-iM iPSCs clones. +; positive control, total RNA was prepared from one day after transfection of OKS-iM-RNA replicon. –; negative control, total RNA was prepared from mock transfected HFFs. Total RNAs from iPS cell clones were prepared from passage 8 (Bottom Panel).

Figure 5:
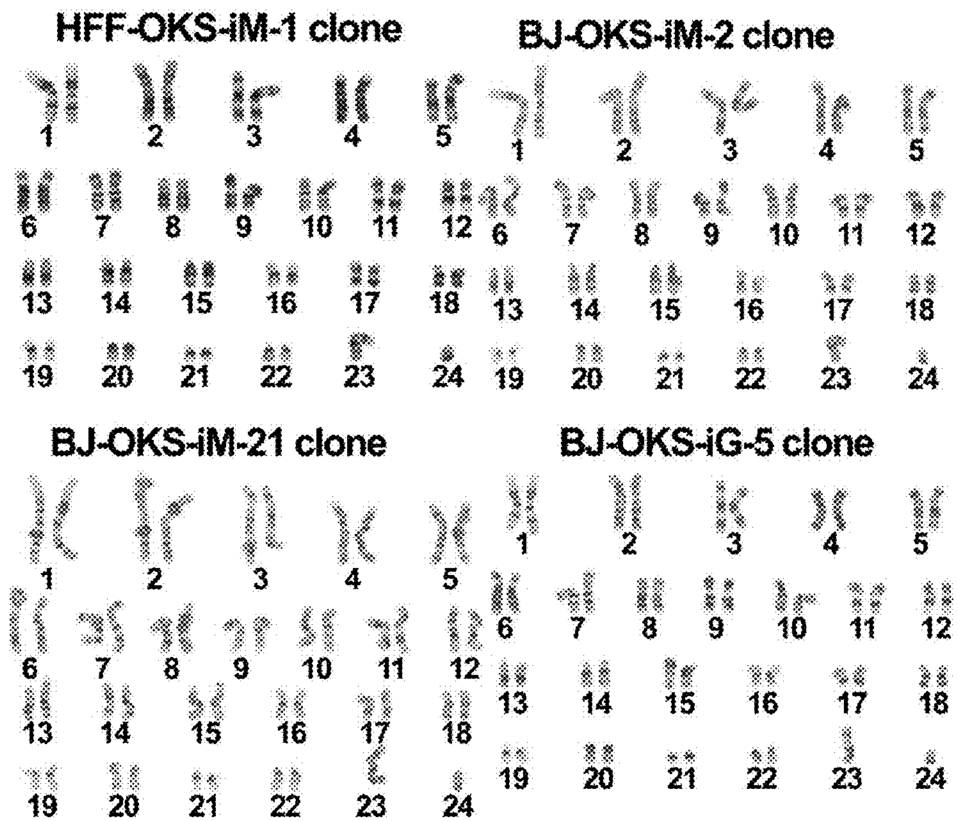

FIG. 5 shows Karyotype Analysis of iPS Cell Clones. G-Banded Karyotyping of HFF-OKS-iM-1, BJ-OKS-iM-2, BJ-OKS-iM-21 and BJ-OKS-iG-5 clones was performed on twenty G-banded metaphase cells from each clone and judged as normal male human karyotype in all clones (Cell line GENETICS).

Figure 6A:
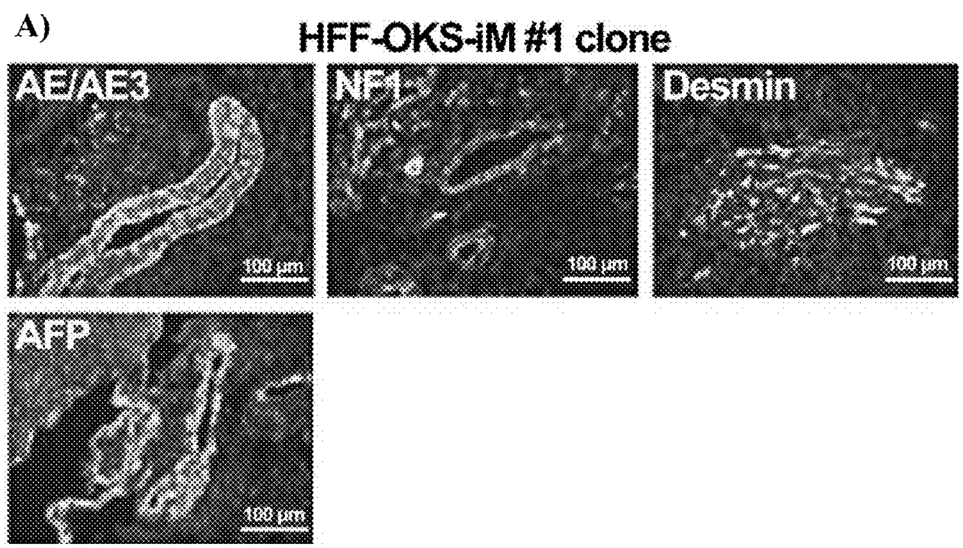

FIG. 6A-B shows iPS cell clones were cultured with STO feeder cells. Cells were collected, and then intramuscularly or subcutaneously injected into the hind limb muscles or dorsal flank of nude mice. After 5 to 8 weeks of injection, tumors were dissected and fixed with 4% paraformaldehyde. (A) Teratoma analysis of HFF-OKS-iM #1 clone in nude mice. AE1/AE3 (cytokeratin) and NF-1 (neuronal cells) used for markers of ectoderm; Desmin (muscle cells) used for marker of mesoderm; and AFP (primitive and definitive endoderm) used for marker of endoderm. Bar, 100 μm. (B) H&E staining of teratomas from BJ-OKS-iG clones 3 and 5. Bar, 100 μm.

FIG. 7A-D shows (A) B18R Conditioned Media is useful for persistent existence of VEE RNA replicon. Top; % of GFP positive cells, Bottom: mean value of GFP fluorescence in GFP positive population. (B) Photographs of cells. Bar, 200 μm. (C) Protein expression of RFs on day 10 as indicated. (D) B18R-CM is required for generation of iPS cells in feeder culture. HFFs were co-transfected with OKS-iM RNA and B18R mRNA as indicated, and then cells were cultured in the presence of B18R-CM and puromycin. Cells were passaged to STO feeder cells on day 10 (d1, 3, 8 transfections) or day 11 (d1, 4, 7, 10 transfections), and cultured in the presence or absence of B18R-CM plus/minus puromycin.

DETAILED DESCRIPTION

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods, devices and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

While induced pluripotent stem cells (iPS cells) are virtually identical to ES cells at molecular and functional levels, there are critical hurdles to translation of their therapeutic potentials into medical applications. One of the issues is that because the current standard protocols for reprogramming and propagation of iPS cells include animal-derived materials that are unsuitable for potential clinical purposes, a fully defined method to generate and expand hiPS cells needs to be developed.

Induced pluripotent stem cells (iPS) are described by Shinya Yamanaka's team at Kyoto University, Japan. Yamanaka identified genes that are particularly active in embryonic stem cells, and used retroviruses to transfect mouse fibroblasts with a selection of those genes. Eventually, four key pluripotency genes essential for the production of pluripotent stem cells were isolated; Oct-3/4, SOX2, c-Myc, and Klf4. Cells were isolated by antibiotic selection for Fbx15$^{+}$ cells. The same group published a study along with two other independent research groups from Harvard, MIT, and the University of California, Los Angeles, showing successful reprogramming of mouse fibroblasts into iPS and even producing a viable chimera.

The generation of human iPS cells by retroviral expression of four reprogramming factors (RFs; also referred to a de-differentiation factors) opened the potential for regenerative medicine therapies based on patient-specific, personalized stem cells. However, the insertional mutagenic potential of retroviruses combined with the potential for latent RF gene activation, especially c-MYC, all but eliminates integrative DNA-based approaches for use in regenerative medicine therapies. Other DNA-based iPS approaches using episomal vectors, adenovirus, integrated and excised piggyBac transposon or floxed lentivirus have been developed; however, these approaches either suffer from low efficiency of iPS cell generation or require genomic excision strategies that leaves behind an inserted DNA element tag. RNA-based iPS cell approaches using Sendai virus or mRNA transfection avoid potential integration problems associated with DNA-based approaches and are inherently safer methods for clinical applications. Although Sendai virus offers a reasonably efficient iPS approach, problems associated with persistent Sendai virus replication in iPS cell clones requires a negative selection step followed by several recloning steps from the single cell level to isolate virus-free iPS cells, such processes result in excessive iPS cellular division and passage. One of the more promising non-DNA based approaches involves daily transfection of four individual RF mRNAs (plus GFP mRNA) over 16 days. Unfortunately, this approach remains problematic. For example, experiments to replace KLF4 and c-MYC retroviruses with corresponding transfected mRNAs were performed and the results validated; however OCT4 and SOX2 retroviruses could not be replaced with transfected mRNAs. The problem appears to stem from both the rapid degradation of RF mRNAs combined with the inconsistent cell-to-cell threshold expression level variation over time, which derives from attempting to transfect four independent mRNAs into the same cell on a daily basis for >14 days during reprogramming. Consequently, there remains a significant need for a simple and highly reproducible, non-DNA based approach to generate human iPS cells.

The disclosure provides methods and compositions for generating iPS cells from somatic cells (e.g., fibroblast cells). The compositions and method comprise the use of replicons derived from alphaviruses. The replicons comprise an RNA sequence encoding non-structural alphavirus proteins necessary for replication and 1, 2, 3, 4 or more coding sequences heterologous to the alphavirus and which induce dedifferentiation of somatic cells to stem cell phenotypes.

As used herein, the term "alphavirus" has its conventional meaning in the art, and includes the various species such as Venezuelan Equine Encephalistis (VEE) Virus, Eastern Equine Encephalistis (EEE) virus, Everglades Virus (EVE), Mucambo Virus (MUC), Pixuna Virus (PIX), and Western Equine Encephalitis Virus, all of which are members of the VEE/EEE Group of alphaviruses. Other alphaviruses include, e.g., Semliki Forest Virus (SFV), Sindbis, Ross River Virus, Chikungunya Virus, S.A. AR86, Barmah Forest Virus, Middleburg Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus, Fort Morgan Virus, Ndumu Virus, and Buggy Creek Virus. Alphaviruses particularly useful in the constructs and methods described herein are VEE/EEE group alphaviruses.

The terms "alphavirus RNA replicon", "alphavirus replicon RNA", "alphavirus RNA vector replicon", and "vector replicon RNA" are used interchangeably to refer to an RNA molecule expressing nonstructural protein genes such that it can direct its own replication (amplification) and comprises, at a minimum, 5' and 3' alphavirus replication recognition sequences, coding sequences for alphavirus nonstructural proteins, and a polyadenylation tract. It may additionally contain one or more elements (e.g., IRES sequences, core or mini-promoters and the like) to direct the expression, meaning transcription and translation, of a heterologous RNA sequence. The alphavirus replicon of the disclosure can comprise, in one embodiment, 5' and 3' alphavirus replication recognition sequences, coding sequences for alphavirus nonstructural proteins, a polyadenylation tract and one or more of a coding sequence selected from the group consisting of SOX-2, c-Myc, OCT-3/4, Klf, Glis1 and Nanog.

The term "polynucleotide," "nucleic acid" or "recombinant nucleic acid" refers to polynucleotides such as deoxyribonucleic acid (DNA), and, where appropriate (particularly with reference to a replicon), ribonucleic acid (RNA).

The term "expression" with respect to a gene or polynucleotide refers to transcription of the gene or polynucleotide and, as appropriate, translation of an mRNA transcript to a protein or polypeptide. Thus, as will be clear from the context, expression of a protein or polypeptide results from transcription and/or translation of the open reading frame.

Those of skill in the art will recognize that, due to the degenerate nature of the genetic code, a variety of codons differing in their nucleotide sequences can be used to encode a given amino acid. A particular polynucleotide or gene sequence encoding a polypeptide described herein are referenced merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the RNA or DNA sequences shown herein merely illustrate embodiments of the disclosure.

The disclosure provides polynucleotides in the form of recombinant DNA expression vectors, RNA replicons or plasmids, as described in more detail elsewhere herein, that encode one or more polypeptides.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by sequence analysis. Furthermore, oligonucleotides corresponding to nucleotide sequences can be prepared by standard synthetic techniques, e.g., using an automated DNA synthesizer.

In one embodiment, a replicon of the disclosure comprise a sequence that is 90%, 95%, 98%, 99% or 100% identical to SEQ ID NO:29, 30, 31, or 32 from about position 1 to about position 7561 (including wherein "T" of the sequence can be substituted with "U"), followed by one or more RFs selected from the group consisting of Oct-3/4, Sox-2, Klf4, c-Myc, Nanog, and Glis1. Where more than one RF is present, the coding sequences may be separated by an internal ribosome entry site (IRES) or a small (e.g., a core) promoter such as SP1. The order of the RFs is not critical to the disclosure; thus the order may be Klf4, Oct-3/4, Sox-2, c-Myc or can be Sox-2, Klf4, Oct-3/4, c-Myc, or Oct4, Klf4, Sox2, c-Myc or any variation of the order of the RFs. The replicon may further comprise a selectable marker (e.g., an antibiotic resistance marker). In other embodiments, coding sequences of RFs may be separated by self-cleaving peptides such as T2A and/or E2A. In another embodiment, the replicon comprises from 5' to 3': (VEE RNA replicases)-(26S promoter)-($RF_1$)-(self cleaving peptide)-($RF_2$)-(self cleaving peptide)-($RF_3$)-(IRES or core promoter)-($RF_4$)-(IRES or optional promoter)-(optional selectable marker)-(VEE 3'UTR and polyA tail); wherein $RF_{1-4}$ are factors that induce de-differentiation of a somatic cell to a pluripotent cells, wherein $RF_{2-3}$ are optional, $RF_{3-4}$ are optional, or $RF_4$ is optional; wherein $RF_{1-4}$ are selected from the group consisting of Oct-4, Klf4, Sox-2, c-Myc, Nanog, and Glis1. In one embodiment, the replicon of the foregoing is an RNA molecule. In a further embodiment, the replicon is derived from VEE and includes a mutation to reduce pathogenicity. In one embodiment, the VEE is a TC-83 strain (vaccine strain)-based RNA replicon with one point mutation ($nsP2P_{773}$ to S mutation), which reduced the cytopathic effect of replicon.

In any of the foregoing embodiments, the RFs include variants and degenerate polynucleotide sequences. For example, an RF can comprise homologs and variants of an OCT-4 polypeptide, KLF4 polypeptide, SOX-2 polypeptide, c-MYC polypeptide, NANOG polypeptide or GLIS1. For example, an RF coding sequence for NANOG useful in any of the replicon embodiments described herein can comprise (i) a polynucleotide encoding a polypeptide of SEQ ID NO:2; (ii) a polynucleotide comprising at least 95% identity to SEQ ID NO:1 and which encodes a polypeptide having NANOG activity; (iii) a polynucleotide having a sequence as set forth in SEQ ID NO:1 or (iv) a polynucleotide encoding a polypeptide of SEQ ID NO:2 containing 1 to 10 conservative amino acid substitutions and wherein the polypeptide has Nanog activity; and wherein any of the foregoing nucleic acid sequences can have "T" replaced with "U". For example, an RF coding sequence for Oct-4 useful in any of the replicon embodiments described herein can comprise (i) a polynucleotide encoding a polypeptide of SEQ ID NO:4; (ii) a polynucleotide comprising at least 95% identity to SEQ ID NO:3 and which encodes a polypeptide having Oct-4 activity; (iii) a polynucleotide having a sequence as set forth in SEQ ID NO:3 or (iv) a polynucleotide encoding a polypeptide of SEQ ID NO:4 containing 1 to 10 conservative amino acid substitutions and wherein the polypeptide has Oct-4 activity; and wherein any of the foregoing nucleic acid sequences can have "T" replaced with "U". For example, an RF coding sequence for Sox-2 useful in any of the replicon embodiments described herein can comprise (i) a polynucleotide encoding a polypeptide of SEQ ID NO:6; (ii) a polynucleotide comprising at least 95% identity to SEQ ID NO:5 and which encodes a polypeptide having SOX-2 activity; (iii) a polynucleotide having a sequence as set forth in SEQ ID NO:5 or (iv) a polynucleotide encoding a polypeptide of SEQ ID NO:6 containing 1 to 10 conservative amino acid substitutions and wherein the polypeptide has SOX-2 activity; and wherein any of the foregoing nucleic acid sequences can have "T" replaced with "U". For example, an RF coding sequence for KLF4 useful in any of the replicon embodiments described herein can comprise (i) a polynucleotide encoding a polypeptide of SEQ ID NO:8; (ii) a polynucleotide comprising at least 95% identity to SEQ ID NO:7 and which encodes a polypeptide having KLF4 activity; (iii) a polynucleotide having a sequence as set forth in SEQ ID NO:7 or (iv) a polynucleotide encoding a polypeptide of SEQ ID NO:8 containing 1 to 10 conservative amino acid substitutions and wherein the polypeptide has KLF4 activity; and wherein any of the foregoing nucleic acid sequences can have "T" replaced with "U". For example, an RF coding sequence for c-MYC useful in any of the replicon embodiments described herein can comprise (i) a polynucleotide encoding a polypeptide of SEQ ID NO:10; (ii) a polynucleotide comprising at least 95% identity to SEQ ID NO:9 and which encodes a polypeptide having c-MYC activity; (iii) a polynucleotide having a sequence as set forth in SEQ ID NO:9 or (iv) a polynucleotide encoding a polypeptide of SEQ ID NO:10 containing 1 to 10 conservative amino acid substitutions and wherein the polypeptide has c-MYC activity; and wherein any of the foregoing nucleic acid sequences can have "T" replaced with "U". For example, an RF coding sequence for GLIS1 useful in any of the replicon embodiments described herein can comprise (i) a polynucleotide encoding a polypeptide of SEQ ID NO:34; (ii) a polynucleotide comprising at least 95% identity to SEQ ID NO:33 and which encodes a polypeptide having GLIS1 activity; (iii) a polynucleotide having a sequence as set forth in SEQ ID NO:33 or (iv) a polynucleotide encoding a polypeptide of SEQ ID NO:34 containing 1 to 10 conservative amino acid substitutions and wherein the polypeptide has GLIS1 activity; and wherein any of the foregoing nucleic acid sequences can have "T" replaced with "U".

Nanog is a gene expressed in embryonic stem cells (ESCs) and plays a role in maintaining pluripotency. Nanog is thought to function with SOX2. A polynucleotide and polypeptide encoding a Nanog is set forth in SEQ ID NO:1 and 2, respectively. Furthermore, SEQ ID NO:1 comprises a DNA sequence it will be recognized that "T" can be replaced with "U". Human NANOG protein (see, e.g., Accession number NP_079141, incorporated herein by reference) is a 305 amino acid protein with a homeodomain motif that is localized to the nuclear component of cells. Similar to murine NANOG, N-terminal region of human NANOG is rich in Ser, Thr and Pro residues and the C-terminus comprises Trp repeats. The homeodomain in human NANOG ranges from about residue 95 to about residue 155. Homologs of human Nanog are known.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include, Oct-1, Oct-2, Oct-3/4, Oct-6, Oct-7, Oct-8, Oct-9, and Oct-11. e.g. Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G. Genes Dev. 11, 1207-1225 (1997). In some embodiments, variants have at least 85%, 90%, or 95% amino acid sequence identity across their whole sequence compared to a naturally occurring Oct polypeptide family member such as to those listed above or such as listed in Genbank accession number NP002692.2 (human Oct4) or NP038661.1 (mouse Oct4). Oct polypeptides (e.g., Oct3/4) can be from human, mouse, rat, bovine, porcine, or other animals. Generally, the same species of protein will be used with the species of cells being manipulated. Oct-4 (Octamer-4) is a homeodomain transcription factor of the POU family and regulates the expression of numerous genes (see, e.g., J. Biol. Chem., Vol. 282, Issue 29, 21551-21560, Jul. 20, 2007, incorporated herein by reference). A polynucleotide and polypeptide encoding an Oct4 is set forth in SEQ ID NO:3 and 4, respectively. Furthermore, SEQ ID NO:3 comprises a DNA sequence it will be recognized that "T" can be replaced with "U". Homologs of human Oct-4 are known as set forth in the following accession numbers NP_038661.1 and NM_013633.1 (*Mus musculus*), NP_001009178 and NM_001009178 (*Rattus norvegicus*), and NP_571187 and NM_131112 (*Danio rerio*), which are incorporated herein by reference.

SRY (sex determining region Y)-box 2, also known as SOX2, is a transcription factor that plays a role in self-renewal of undifferentiated embryonic stem cells and trans-activation of Fgf4 as well as modulating DNA bending (see, e.g., Scaffidi et al. J. Biol. Chem., Vol. 276, Issue 50, 47296-47302, Dec. 14, 2001, incorporated herein by reference). A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, e.g., Dang, D. T., et al., Int. J. Biochem. Cell Biol. 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. See, Nakagawa, et al., Nature Biotechnology 26:101-106 (2007). In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated. A polynucleotide and polypeptide encoding a Sox2 is set forth in SEQ ID NO:5 and 6, respectively. Furthermore, SEQ ID NO:5 comprises a DNA sequence it will be recognized that "T" can be replaced with "U". Homologs of human Sox2 are known.

Kruppel-like factor 4, also known as KLF4 plays a role in stem cell maintenance and growth. A "Klf polypeptide" refers to any of the naturally-occurring members of the family of Kruppel-like factors (Klfs), zinc-finger proteins that contain amino acid sequences similar to those of the *Drosophila* embryonic pattern regulator Kruppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W., Cell Biol. 32, 1103-1121 (2000). Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. See, Nakagawa, et al., Nature Biotechnology 26:101-106 (2007). In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. To the extent a Klf polypeptide is described herein, it can be replaced with an estrogen-related receptor beta (Essrb) polypeptide. Thus, it is intended that for each Klf polypeptide embodiment described herein, a corresponding embodiment using Essrb in the place of a Klf4 polypeptide is equally described. A polynucleotide and polypeptide encoding an KLF4 is set forth in SEQ ID NO:7 and 8, respectively. Furthermore, SEQ ID NO:7 comprises a DNA sequence it will be recognized that "T" can be replaced with "U". Homologs of human KLF4 are known and include NP_034767, NM_010637 (*Mus musculus*), which are incorporated herein by reference.

The MYC family of cellular genes is comprised of c-myc, N-myc, and L-myc, three genes that function in regulation of cellular proliferation, differentiation, and apoptosis (Henriksson and Luscher 1996; Facchini and Penn 1998). A "Myc polypeptide" refers any of the naturally-occurring members of the Myc family (see, e.g., Adhikary, S. & Eilers, M. Nat. Rev. Mol. Cell Biol. 6:635-645 (2005)), or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated. Although myc family genes have common structural and biological activity. N-Myc is a member of the MYC family and encodes a protein with a basic helix-loop-helix (bHLH) domain. The genomic structures of c-myc and N-myc are similarly organized and are comprised of three exons. Most of the first exon and the 3' portion of the third exon contain untranslated regions that carry transcriptional or post-transcriptional regulatory sequences. N-myc protein is found in the nucleus and dimerizes with another bHLH protein in order to bind DNA. A polynucleotide and polypeptide encoding an c-Myc is set forth in SEQ ID NO:9 and 10, respectively. Furthermore, SEQ ID NO:9 comprises a DNA sequence it will be recognized that "T" can be replaced with "U". Homologs and variants of the Myc family of proteins are known in the art.

Glis1 (Glis Family Zinc Finger 1) is gene encoding a Krüppel-like protein of the same name whose locus is found on Chromosome 1p32.3. The gene is enriched in unfertilised eggs and embryos at the one cell stage and it can be used to promote direct reprogramming of somatic cells to induced pluripotent stem cells. Glis1 can be used as one of the four factors used in reprogramming somatic cells to induced pluripotent stem cells. The three other transcription factors used are Oct3/4, Sox2 and Klf4. A human Glis1 (NM_147193) is set forth in SEQ ID NO:33 and 34 (cDNA and polypeptide, respectively).

cDNA coding for the human oct4 (pour5f1), sox2, klf4, c-myc (n-myc or L-myc), Glis1 and nanog, variants and homologs thereof can be cloned and expressed using techniques known in the art. Using the sequences set forth herein polynucleotides encoding one or more de-differentiation factors can be cloned into a suitable vector for expression in a cell type of interest.

An RF "activity" (e.g., an RF variant activity) refers the ability to de-differentiate a somatic cell when expressed in combination with other RFs as known in the art. For example, an Oct-4 variant can be measured for Oct-4 activity by co-expressing the Oct-4 variant in a somatic cell with klf4, Sox-2 and c-myc and determining if a somatic cell de-differentiates. If the cell de-differentiates than the Oct-4 variant can be said to have Oct-4 activity.

In another embodiment, the replicon comprises a sequence as set forth in SEQ ID NO:29, 30, 31, or 32. In yet another embodiment, the replicon comprises a sequence that is about 90%, 92%, 93%, 94%, 95%, 96%, 97%, 98%, 99%, 99.5% identical to SEQ ID NO:29, 30, 31, or 32, and wherein when the replicon is transfected into a somatic cells, the somatic cell is "induced" to become a stem cell. In addition, any of SEQ ID NO:29, 30, 31, or 32, wherein "T" is replaced by "U".

In one embodiment, SEQ ID NO:29 provides a replicon of the disclosure. In another embodiment the sequence of SEQ ID NO:29 has "T" replaced with "U". The replicon comprises VEE RNA replicases from nucleotide 1 to about nucleotide 7561, a human Oct-4 sequence from nucleotide 7592 to 8671, a coding sequence for a T2A self-cleaving peptide from nucleotide 8678-8731, a human Klf4 sequence from 8738-10147, a coding sequence for a self-cleaving E2A peptide from nucleotide 10154-10213, a human Sox-2 sequence from 10223-11176, an internal ribosome entry site from 11195-11805, a human c-Myc sequence from 11818-13140, an internal ribosome entry site from 13165-13776, a puromycin resistance gene from 13777-14376, the VEE 3'UTR and polyA tail from 14383-14510, an ampicillin resistance gene from 14679-15539 and a SP6 promoter from 16320-16337.

In one embodiment, SEQ ID NO:30 provides a replicon of the disclosure. In another embodiment the sequence of SEQ ID NO:30 has "T" replaced with "U". The replicon comprises VEE RNA replicases from nucleotide 1 to about nucleotide 7561, a human Oct-4 sequence from nucleotide 7592 to 8671, a coding sequence for a T2A self-cleaving peptide from nucleotide 8678-8731, a human Klf4 sequence from 8738-10147, a coding sequence for a self-cleaving E2A peptide from nucleotide 10154-10213, a human Sox-2 sequence from 10223-11176, an internal ribosome entry site from 11195-11805, a human c-Myc sequence from 11818-13140, an internal ribosome entry site from 13165-13776, a puromycin resistance gene from 13777-14376, the VEE 3'UTR and polyA tail from 14383-14510, an ampicillin resistance gene from 14679-15539 and a T7 promoter from 16319-16336.

In one embodiment, SEQ ID NO:31 provides a replicon of the disclosure. In another embodiment the sequence of SEQ ID NO:31 has "T" replaced with "U". The replicon comprises VEE RNA replicases from nucleotide 1 to about nucleotide 7561, a human Oct-4 sequence from nucleotide 7592 to 8671, a coding sequence for a T2A self-cleaving peptide from nucleotide 8678-8731, a human Klf4 sequence from 8738-10147, a coding sequence for a self-cleaving E2A peptide from nucleotide 10154-10213, a human Sox-2 sequence from 10223-11176, an internal ribosome entry site from 11195-11805, a human Glis1 sequence from 11818-13680, an internal ribosome entry site from 13689-14300, a puromycin resistance gene from 14301-14900, the VEE 3'UTR and polyA tail from 14907-15034, an ampicillin resistance gene from 15203-16063 and a SP6 promoter from 16844-16861.

In one embodiment, SEQ ID NO:32 provides a replicon of the disclosure. In another embodiment the sequence of SEQ ID NO:32 has "T" replaced with "U". The replicon comprises VEE RNA replicases from nucleotide 1 to about nucleotide 7561, a human Oct-4 sequence from nucleotide 7592 to 8671, a coding sequence for a T2A self-cleaving peptide from nucleotide 8678-8731, a human Klf4 sequence from 8738-10147, a coding sequence for a self-cleaving E2A peptide from nucleotide 10154-10213, a human Sox-2 sequence from 10223-11176, an internal ribosome entry site from 11195-11805, a human Glis1 sequence from 11818-13680, an internal ribosome entry site from 13689-14300, a puromycin resistance gene from 14301-14900, the VEE 3'UTR and polyA tail from 14907-15034, an ampicillin resistance gene from 15203-16063 and a T7 promoter from 16843-16860.

In another embodiment, more than one alphavirus replicon may be used, each replicon comprising one or more coding sequences for factors that induce a somatic cell to become a stem cell, wherein the combination of the more than one alphavirus replicons include all the coding sequence for all RFs necessary for inducing de-differentiation into a stem cell.

In more specific embodiments, an alphavirus replicon comprises coding sequences for expression of OCT-3/4, SOX-2, KLF, c-MYC, GLIS1 and/or NANOG. In a specific embodiment, the alphavirus replicon comprises coding sequences for OCT-4, KLF4, SOX-2, GLIS1 and c-MYC.

The replicon may also be engineered to express alphavirus structural proteins. U.S. Pat. Nos. 7,045,335, 7,078,218, 7,425,337 and 7,442,381 describe numerous constructs for such alphavirus RNA replicons consisting of the 5' and 3' alphavirus replication recognition sequences, coding sequences for alphavirus nonstructural proteins, and a polyadenylation tract, and such constructs are incorporated herein by reference. Specific embodiments of the alphavirus RNA replicons may contain one or more attenuating mutations, an attenuating mutation being a nucleotide deletion, addition, or substitution of one or more nucleotide(s), or a mutation that comprises rearrangement or chimeric construction which results in a loss of virulence in a live virus containing the mutation as compared to the appropriate wild-type alphavirus.

The terms "alphavirus structural protein/protein(s)" refers to one or a combination of the structural proteins encoded by alphaviruses. These are produced by the virus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2. Attenuating mutations can be introduced into any one or more of the alphavirus structural proteins.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 920, 930, 940, 950, 960, 970, 980, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

As described herein, the compositions and methods of the disclosure provide the ability to de-differentiate somatic cells to form stem cells (e.g., induce the formation of stem cells). Stem cells are cells capable of differentiation into other cell types, including those having a particular, specialized function (e.g., tissue specific cells, parenchymal cells and progenitors thereof). There are various classes of stem cells, which can be characterized in their ability to differentiate into a desired cell/tissue type. For example, "progenitor cells" can be either multipotent or pluripotent. Progenitor cells are cells that can give rise to different terminally differentiated cell types, and cells that are capable of giving rise to various progenitor cells. The term "pluripotent" or "pluripotency" refers to cells with the ability to give rise to progeny cells that can undergo differentiation, under the appropriate conditions, into cell types that collectively demonstrate characteristics associated with cell lineages from all of the three germinal layers (endoderm, mesoderm, and ectoderm). Pluripotent stem cells can contribute to all embryonic derived tissues of a prenatal, postnatal or adult animal. A standard art-accepted test, such as the ability to form a teratoma in 8-12 week old SCID mice, can be used to establish the pluripotency of a cell population; however identification of various pluripotent stem cell characteristics can also be used to detect pluripotent cells. "Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least some, and in some embodiments, all of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics. In comparison, a multipotent stem cell is capable of differentiating into a subset of cells compared to a pluripotent stem cell. For example, a multipotent stem cell may be able to undergo differentiation into one or two of the three germinal layers. As used herein, "non-pluripotent cells" refer to mammalian cells that are not pluripotent cells. Examples of such cells include differentiated cells as well as multipotent cells. Examples of differentiated cells include, but are not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells.

Another class of cells even more primitive (i.e., uncommitted to a particular differentiation fate) than pluripotent stem cells are the so-called "totipotent" stem cells (e.g., fertilized oocytes, cells of embryos at the two and four cell stages of development), which have the ability to differentiate into any type of cell of the particular species. For example, a single totipotent stem cell could give rise to a complete animal, as well as to any of the myriad of cell types found in the particular species (e.g., humans).

Pluripotent stem cells are a type of cells that undergo self-renewal while maintaining an ability to give rise to all three germ layer-derived tissues and germ cell lineages. Although pluripotent human embryonic stem (hES) cells derived from human blastocysts are promising sources for cell-based therapies to treat diseases and disorders such as Parkinson's disease, cardiac infarction, spinal cord injury, and diabetes mellitus, their clinical potentials has been hampered by their immunogenicity and ethical concerns.

The term "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew its line or to produce progeny cells which will differentiate into fibroblasts or a lineage-committed progenitor cell and its progeny, which is capable of self-renewal and is capable of differentiating into a parenchymal cell type. Unlike pluripotent stem cells, lineage-committed progenitor cells are generally considered to be incapable of giving rise to numerous cell types that phenotypically differ from each other. Instead, they give rise to one or possibly two lineage-committed cell types.

The disclosure demonstrates that terminally differentiated human cells (e.g., human dermal fibroblasts) can be induced to de-differentiate using an ectopic mRNA expression system (e.g., a replicon system). The disclosure contemplates the use of a variety of de-differentiation (also referred to as Reprogramming Factors (RFs)) coding sequence comprising, for example, a polynucleotide that encodes KLF4, OCT4, SOX2, c-MYC or n-MYC (L-Myc), GLIS1, NANOG or any combination thereof (e.g., KLF4, OCT4, SOX2, c-MYC or n-MYC (L-Myc) and optionally NANOG). De-differentiation may be achieved by contacting a cell, in vivo or in vitro, with one or more self-replicating RNA vectors that remain ectopic to the host cell genome and encode factors that induce de-differentiation. In various embodiments the ectopic self-replicating RNA vector of the disclosure can be controlled by culturing a host cell transformed with the self-replicating RNA vector in the presence of B18R. Methods for promoting de-differentiation provide methods of promoting regeneration of mammalian cells and tissues damaged by injury or disease. The disclosure also provides methods for enriching for induced stem cells and populations comprising such enriched stem cells.

The generation of patient-specific pluripotent stem cells has the potential to dramatically speed the implementation of stem cells into clinical use to treat degenerative diseases. The disclosure provides methods to employ easily donated stromal cells, such as dermal fibroblasts, from a patient and generate Human Induced Pluripotent Stem (hiPS or iPS) cells by ectopic expression of a set of de-differentiation factors comprising RNA encoding (i) KLF4, OCT4, SOX2, c-MYC or n-MYC(L-Myc), NANOG or any combination thereof; (ii) KLF4, OCT4, SOX2, and GLIS1; and (iii) KLF4, OCT4, SOX2, and NANOG. The cell lines generated are physiologically and morphologically indistinguishable from Human Embryonic Stem Cells (HESC) generated from the inner cell mass of a human embryo. hiPS cells share a nearly identical gene expression profile with two established HESC lines.

The term "de-differentiation" is familiar to the person skilled in the relevant art. In general de-differentiation signifies the regression of lineage committed cell to the status of a stem cell, for example, by "inducing" a de-differentiated phenotype. For example, as described further herein KLF4, OCT4, SOX2, c-MYC or n-MYC or L-MYC, GLIS1 and/or Nanog can induce de-differentiation and induction of mitosis in lineage committed mitotically inhibited cells.

In one embodiment, the disclosure provides a cell culture comprising human somatic cells that have been transformed with a replicon of the disclosure. In one embodiment the somatic cells are fibroblasts. In another embodiment, the somatic cells are keratinocytes. In another embodiment, the replicon comprises a sequence that is 90%, 95%, 98%, 99% or 100% identical to SEQ ID NO:29, 30, 31, or 32 from about position 1 to about position 7561 (including wherein "T" of the sequence can be substituted with "U"), followed by one or more RFs selected from the group consisting of Oct-3/4, Sox-2, Klf4, c-Myc, Nanog, and Glis1 followed by a VEE 3'UTR and polyA tail. Where when more than one RF is present, the coding sequences may be separated by an internal ribosome entry site (IRES) or a small (e.g., a core) promoter such as SP1. The order of the RFs is not critical to the disclosure; thus the order may be Klf4, Oct-3/4, Sox-2, c-Myc or can be Sox-2, Klf4, Oct-3/4, c-Myc, or Oct4, Klf4, Sox2, c-Myc or any variation of the order of the RFs. In one embodiment, the replicon comprises a sequence that is at least about 95%, 98%, 99% or 100% identical to a sequence as set forth in SEQ ID NO:29, 30, 31, or 32. In yet another embodiment, the cells are cultured in conditioned media comprising B18R and/or are co-transformed with a polynucleotide encoding B18R.

The disclosure also provide methods of making a stem cell from a somatic cell comprising transforming the somatic cell with an RNA replicon as described in the disclosure and culturing the somatic cell under conditions to promote expression of coding sequences in the replicon and culturing the cells for a sufficient period of time to de-differentiate the cells to stem cells. In one embodiment, the cells are passaged at least 5, 10, 15, 20 or more times. In another embodiment, the cells are cultured for at least 10, 20, 30 or more days. In yet another embodiment, the cells are cultured in conditioned media comprising B18R or are co-transformed with a polynucleotide encoding B18R.

The disclosure also provides induced stem cell cultures obtained by the methods described herein. In one embodiment, the stem cells do not contain any heterologous RF factors in the genomic DNA of the cell. In another embodiment, the stem cells do not contain any retroviral DNA or RNA (e.g., stem cells that are retroviral DNA- or RNA-free).

In one embodiment, the disclosure provides isolated induced stem cells, individually or in populations. The term "isolated" or "purified" when referring to stem cells of the disclosure means cells that are substantially free of cells carrying markers associated with lineage dedication. In particular embodiments, the human induced pluripotent stem cells are at least 30%, 35%, 40%, 45%, 50%, 55%, 60%, 65%, 70%, 75%, 80%, 85%, 90%, 95% or 99% free of such contaminating cell types. In another embodiment, the isolated stem cells also are substantially free of soluble, naturally occurring molecules. As discussed more fully below, a substantially purified stem cell of the disclosure can be obtained, for example, by extraction (e.g., via density gradient centrifugation and/or flow cytometry) from a culture source. Purity can be measured by any appropriate method. A stem cell of the disclosure can be 99%-100% purified by, for example, flow cytometry (e.g., FACS analysis), as discussed herein. Such purified iPS cells will lack any retroviral DNA or RNA.

In one embodiment, the disclosure provides an enriched population of induced stem cells. An "enriched population of induced stem cells" is one wherein induced stem cells of the disclosure have been partially separated from other cell types, such that the resulting population of cells has a greater concentration of induced stem cells than the original population of cells. The enriched population of induced stem cells can have greater than about a 10-fold, 100-fold, 500-fold, 1,000-fold, 2,000-fold, 3,000-fold, 4,000-fold, 5,000-fold, 6,000-fold, 7,000-fold, 8,000-fold, 9,000-fold, 10,000-fold or greater concentration of induced stem cells than the original population had prior to separation. Induced stem cells of the disclosure can, for example, make up at least 5%, 10%, 15%, 20%, 35%, 30%, 35%, 40%, 45%, 50%, 55%, 60%, 65%, 70%, 75%, 80%, 85%, 90%, 95%, 99% or more of the enriched population of stem cells. The enriched population of induced stem cells may be obtained by, for example, selecting against cells displaying markers associated with differentiated cells, or other undesired cell types, and/or selecting for cells displaying markers (e.g., TRA-1-81 and/or TRA-1-60) associated with the human induced pluripotent stem cells of the disclosure, and/or by regenerating isolated stem cells in defined culture systems. Alternatively, or in addition to, the enrichment for the expression of a marker, the loss of expression of a marker may also be used for enrichment. Such enriched iPS cells will lack any retroviral RNA or DNA typically used to transform cells with RFs.

In another embodiment, the disclosure provides cell lines of induced stem cells. As used herein a "cell line" means a culture of stem cells of the disclosure, or progeny cells thereof, that can be reproduced for an extended period of time, preferably indefinitely, and which term includes, for example, cells that are cultured, cryopreserved and re-cultured following cryopreservation. As used herein a "culture" means a population of induced stem cells grown in a medium and optionally passaged accordingly. A stem cell culture may be a primary culture (e.g., a culture that has not been passaged) or may be a secondary or subsequent culture (e.g., a population of cells which have been subcultured or passaged one or more times).

In one embodiment, the disclosure provides cells that are de-differentiated to stem cells (i.e., induced stem cells) comprising characteristics including the ability of self-renewal and differentiation into mesoderme, endoderm and epiderm, wherein the de-differentiated cells can be produced by expression of one or more RFs ectopic to the host cell genome using a replicating RNA vector. In one embodiment, the replicon vector is derived from an alphavirus (e.g., Venezuelan Equine Encehalitis virus).

Therapeutic uses of the human induced pluripotent stem cells of the disclosure include transplanting the human induced pluripotent stem cells, stem cell populations, or progeny thereof into individuals to treat a variety of pathological states including diseases and disorders resulting from cancers, neoplasms, injury, viral infections, diabetes and the like. Stem cells or stem cell populations (including genetically altered stem cells) are introduced into a subject in need of such stem cells or progeny or in need of a KLF4, OCT4, SOX2, c-MYC or n-MYC or L-MYC, NANOG, GLIS1 or any combination thereof protein or molecule encoded or produced by the genetically altered cell. For example, in one embodiment, the human induced pluripotent stem cells can be administered to cancer patients who have undergone chemotherapy that have killed, reduced, or damaged stem cells or other cells of a subject, wherein the induced stems cells replace the damaged or dead cells. In another embodiment, the human induced pluripotent stem cells can be transfected or transformed (in addition to the de-differentiation factors) with at least one additional therapeutic factor. For example, once human induced pluripotent stem cells of the disclosure are isolated or obtained by the methods of the disclosure, the stem cells may be transformed with a polynucleotide encoding a therapeutic polypeptide. Such a method and compositions can provide stem cell bioreactors for the production of a desired polypeptide or may be used for gene delivery or gene therapy. In this embodiment, the iPS cells may be isolated, transformed with a polynucleotide encoding a therapeutic polypeptide and may then be implanted or administered to a subject, or may be differentiated to a desired cell type and implanted and delivered to the subject. Under such conditions the polynucleotide is expressed within the subject for delivery of the polypeptide product.

If the human cells are derived from a heterologous (non-autologous/allogenic) source compared to the recipient subject, concomitant immunosuppression therapy is typically administered, e.g., administration of the immunosuppressive agent cyclosporine or FK506. However, due to the immature state of the human induced pluripotent stem cells of the disclosure such immunosuppressive therapy may not be required. Accordingly, in one embodiment, the human induced pluripotent stem cells of the disclosure can be administered to a recipient in the absence of immunomodulatory (e.g., immunosuppressive) therapy. Alternatively, the cells can be encapsulated in a membrane, which permits exchange of fluids but prevents cell/cell contact. Transplantation of microencapsulated cells is known in the art, e.g., Balladur et al., 1995, Surgery 117:189-94, 1995; and Dixit et al., 1992, Cell Transplantation 1:275-79.

The cells may be introduced directly into the peripheral blood or deposited within other locations throughout the body, e.g., a desired tissue, or on microcarrier beads in the peritoneum. For example, $10^2$ to $10^9$ cells can be transplanted in a single procedure, and additional transplants can be performed as required.

Differentiation of the human induced pluripotent stem cells or de-differentiation of lineage committed (mitotically inhibited) cells can be induced ex vivo, or alterantively may be induced by contact with tissue in vivo, (e.g., by contact with fibroblasts or cell matrix components). Optionally, a differentiating agent or de-differentiation agent (e.g., KLF4, OCT4, SOX2, c-MYC or n-MYC or L-MYC, NANOG, GLIS1, or any combination thereof or an agonist thereof) may be co-administered or subsequently administered to the subject.

It has been previously demonstrated that transplantation of beta islet cells provides therapy for patients with diabetes (Shapiro et al., 2000). The human induced pluripotent stem cells of the disclosure provide an alternative source of islet cells to prevent or treat diabetes. For example, induced pluripotent stem cells of the disclosure can be generated, isolated and differentiated to a pancreatic cell type and delivered to a subject. Alternatively, the induced pluripotent stem cells can be delivered to the pancreas of the subject and differentiated to islet cells in vivo. Accordingly, the cells are useful for transplantation in order to prevent or treat the occurrence of diabetes.

The disclosure contemplates that the in vitro methods described herein can be used for autologous transplantation of de-differentiated or redifferentiated cells (e.g., the cells are harvested from and returned to the same individual). The disclosure further contemplates that the in vitro methods described herein can be used for non-autologous transplantations. In one embodiment, the transplantation occurs between a genetically related donor and recipient. In another embodiment, the transplantation occurs between a genetically un-related donor and recipient. In any of the foregoing embodiments, the disclosure contemplates that de-differentiated cells can be expanded in culture and stored for later retrieval and use. Similarly, the disclosure contemplates that redifferentiated cells can be can be expanded in culture and stored for later retrieval and use.

The compositions and methods of the disclosure may be applied to a procedure wherein differentiated (lineage committed) cells are removed from the a subject, de-differentiated in culture, and then either reintroduced into that individual or, while still in culture, manipulated to redifferentiate along specific differentiation pathways (e.g., pancreatic cells, neuronal cells, liver cells, skin cells, cardiovascular cells, gastrointestinal cells and the like). Such redifferentiated cells can then be introduced to the individual. For example, differentiated fibroblasts can be removed, de-differentiated (e.g., with ectopic expression of a replicon of the disclosure comprising KLF4, OCT4, SOX2, c-MYC or n-MYC or L-MYC, GLIS1, NANOG or any combination thereof) and mitotically expanded and then redifferentiated (e.g., with a KLF4, OCT4, SOX2, c-MYC or n-MYC or L-MYC, NANOG, GLIS1 antagonists or any combination thereof) or factors (including physical stimuli) known to cause differentiation of hESCs down a lineage committed path. In one embodiment, the method comprises removing differentiated cells from an injured or diseased subject. Cells de-differentiated from cells harvested from an injured subject can later be returned to the injured or diseased subject to treat an injury or degenerative disease. The de-differentiated cells can be reintroduced at the site or injury, or the cells can be reintroduced at a site distant from the injury. Similarly, cells can be harvested from an injured subject, de-differentiated in vitro, redifferentiated in vitro, and transplanted back to the subject to treat an injury or degenerative disease.

The human induced pluripotent stem cells of the disclosure can be isolated from a sample obtained from a mammalian subject. The subject can be any mammal (e.g., bovine, ovine, porcine, canine, feline, equine, primate), including a human. The sample of cells may be obtained from any of a number of different sources including, for example, bone marrow, fetal tissue (e.g., fetal liver tissue), peripheral blood, umbilical cord blood, pancreas and the like.

In another embodiment, the disclosure provides methods of establishing and/or maintaining populations of stem cells, or the progeny thereof, as well as mixed populations comprising both stem cells and progeny cells, and the populations of cells so produced. As with the human induced pluripotent stem cells of the disclosure, once a culture of cells or a mixed culture of stem cells is established, the population of cells is mitotically expanded in vitro by passage to fresh medium as cell density dictates under conditions conducive to cell proliferation, with or without tissue formation. Such culturing methods can include, for example, passaging the cells in culture medium lacking particular growth factors that induce differentiation (e.g., IGF, EGF, FGF, VEGF, and/or other growth factor), in the presence of an agent that stimulates (e.g., an agonist) of KLF4, OCT4, SOX2, c-MYC or n-MYC or L-MYC, NANOG, GLIS1 or any combination thereof, in the presence of KLF4, OCT4, SOX2, c-MYC or n-MYC or L-MYC, NANOG, Glis1 or any combination thereof, or any combination of the foregoing. Cultures comprising fibroblast or fibroblast-like cells and mixed cultures comprising stem cells and fibroblast cells can be transferred to fresh medium when sufficient cell density is reached. Some stem cell types do not demonstrate typical contact inhibition-apoptosis or they become quiescent when density is maximum. Accordingly, appropriate passaging techniques can be used to reduce contact inhibition and quiescence. Thus, in one embodiment, for example, transferring a portion of the cells to a new culture vessel with fresh medium. Such removal or transfer can be done in any culture vessel.

Once the human induced pluripotent stem cells of the disclosure have been established in culture, as described above, they may be maintained or stored in cell “banks”

comprising either continuous in vitro cultures of cells requiring regular transfer or cells which have been cryopreserved.

Cryopreservation of stem cells, or other cell of the disclosure, may be carried out according to known methods, such as those described in Doyle et al., (eds.), 1995, Cell & Tissue Culture: Laboratory Procedures, John Wiley & Sons, Chichester. For example, but not by way of limitation, cells may be suspended in a "freeze medium" such as, for example, culture medium further comprising 15-20% fetal bovine serum (FBS) and 10% dimethylsulfoxide (DMSO), with or without 5-10% glycerol, at a density, for example, of about $4\text{-}10\times10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of −1° C./min through the heat of fusion may be used. Once vials containing the cells have reached −80° C., they are transferred to a liquid nitrogen storage area. Cryopreserved cells can be stored for a period of years, though they should be checked at least every 5 years for maintenance of viability.

The cryopreserved cells of the disclosure constitute a bank of cells, portions of which can be withdrawn by thawing and then used to produce a stem cell culture comprising stem cells, as needed. Thawing should generally be carried out rapidly, for example, by transferring a vial from liquid nitrogen to a 37° C. water bath. The thawed contents of the vial should be immediately transferred under sterile conditions to a culture vessel containing an appropriate medium. It is advisable that the cells in the culture medium be adjusted to an initial density of about $1\text{-}3\times10^5$ cells/ml. Once in culture, the cells may be examined daily, for example, with an inverted microscope to detect cell proliferation, and subcultured as soon as they reach an appropriate density.

The human induced pluripotent stem cells of the disclosure may be withdrawn from a cell bank as needed, and used for the production of new stem cells, either in vitro, for example, as a three dimensional tissue culture, as described below, or in vivo, for example, by direct administration of cells to the site where new fibroblasts or tissue is needed. As described herein, the human induced pluripotent stem cells of the disclosure may be used to produce new tissue for use in a subject where the cells were originally isolated from that subject's own blood or other tissue (i.e., autologous cells). Alternatively, the cells of the disclosure may be used as ubiquitous donor cells to produce new tissue for use in any subject (i.e., heterologous cells).

Once established, a culture of stem cells may be used to produce progeny cells and/or fibroblasts capable of producing new tissue. Differentiation of stem cells to fibroblasts or other cell types, followed by the production of tissue therefrom, can be triggered by specific exogenous growth factors or by changing the culture conditions (e.g., the density) of a stem cell culture. Since the cells are pluripotent, they can be used to reconstitute an irradiated subject and/or a subject treated with chemotherapy; or as a source of cells for specific lineages, by providing for their maturation, proliferation and differentiation into one or more selected lineages. Examples of factors that can be used to induce differentiation include erythropoietin, colony stimulating factors, e.g., GM-CSF, G-CSF, or M-CSF, interleukins, e.g., IL-1, -2, -3, -4, -5, -6, -7, -8, and the like, Leukemia Inhibitory Factory (LIF), Steel Factor (Stl), or the like, coculture with tissue committed cells, or other lineage committed cells types to induce the stem cells into becoming committed to a particular lineage.

In another embodiment, the human induced pluripotent stem cells are genetically engineered to express genes for specific types of growth factors for successful and/or improved differentiation to fibroblasts, other stromal cells, or parenchymal cells and/or turnover either pre- or post-implantation.

The cells of the disclosure may be used to treat subjects requiring the repair or replacement of tissue resulting from disease or trauma. Treatment may entail the use of the cells of the disclosure to produce new tissue, and the use of the tissue thus produced, according to any method presently known in the art or to be developed in the future. For example, the induced cells (e.g., cells comprising an ectopic expression vector expressing KLF4, OCT4, SOX2, c-MYC or n-MYC or L-MYC, NANOG, Glis1 or any combination thereof) of the disclosure may be implanted, injected or otherwise administered directly to the site of tissue damage so that they will produce new tissue in vivo. In one embodiment, administration includes the administration of genetically modified stem cells.

In one embodiment, a formulation comprising the cells of the disclosure is prepared for injection directly to the site where the production of new tissue is desired. For example, and not by way of limitation, the cells of the disclosure may be suspended in a hydrogel solution for injection. Alternatively, the hydrogel solution containing the cells may be allowed to harden, for instance in a mold to form a matrix having cells dispersed therein prior to implantation. Once the matrix has hardened, the cell formations may be cultured so that the cells are mitotically expanded prior to implantation. A hydrogel is an organic polymer (natural or synthetic) which is cross-linked via convalent, ionic, or hydrogen bonds to create a three-dimensional open-lattice structure, which entraps water molecules to form a gel. Examples of materials which can be used to form a hydrogel include polysaccharides such as alginate and salts thereof, polyphosphazines, and polyacrylates, which are cross-linked ionically, polyethylene oxide-polypropylene glycol block copolymers which are cross-linked by temperature or pH, respectively. Methods of synthesis of the hydrogel materials, as well as methods for preparing such hydrogels, are known in the art.

Such cell formulations may further comprise one or more other components, including selected extracellular matrix components, such as one or more types of collagen known in the art, and/or growth factors and drugs. Growth factors which may be usefully incorporated into the cell formulation include one or more tissue growth factors known in the art such as, but not limited to, any member of the TGF-β family, IGF-I and -II, growth hormone, BMPs such as BMP-13, and the like. Alternatively, the cells of the disclosure may be genetically engineered to express and produce growth factors such as BMP-13 or TGF-β. Other components may also be included in the formulation include, for example, buffers to provide appropriate pH and isotonicity, lubricants, viscous materials to retain the cells at or near the site of administration, (e.g., alginates, agars and plant gums) and other cell types that may produce a desired effect at the site of administration (e.g., enhancement or modification of the formation of tissue or its physicochemical characteristics, support for the viability of the cells, or inhibition of inflammation or rejection). The cells can be covered by an appropriate wound covering to prevent cells from leaving the site. Such wound coverings are known to those of skill in the art.

Alternatively, the human induced pluripotent stem cells of the disclosure may be seeded onto a three-dimensional framework or scaffold and cultured to allow the cells to differentiate, grow and fill the matrix or immediately implanted in vivo, where the seeded cells will proliferate on the surface of the framework and form a replacement tissue in vivo in cooperation with the cells of the subject. Such a framework can be implanted in combination with any one or more growth factors, drugs, additional cell types, or other components that stimulate formation or otherwise enhance or improve the practice of the disclosure.

In yet another embodiment, the human induced pluripotent stem cells of the disclosure can be used in conjunction with a three-dimensional culture system in a "bioreactor" to produce tissue constructs which possess critical biochemical, physical and structural properties of native human tissue by culturing the cells and resulting tissue under environmental conditions which are typically experienced by native tissue. The bioreactor may include a number of designs. Typically the culture conditions will include placing a physiological stress on the construct containing cells similar to what will be encountered in vivo.

The human induced pluripotent stem cells, their progeny, and tissue of the disclosure can be used in a variety of applications. These include, but are not limited to, transplantation or implantation of the cells either in a differentiated form, an undifferentiated form, a de-differentiated form. Such cells and tissues serve to repair, replace or augment tissue that has been damaged due to disease or trauma, or that failed to develop normally.

The human induced pluripotent stem cells and tissue produced according to the disclosure can be used to repair or replace damaged or destroyed tissue or to augment existing tissue.

In addition, the cells or tissue of the disclosure can be used, for example, to screen in vitro for the efficacy and/or cytotoxicity of compounds, allergens, growth/regulatory factors, pharmaceutical compounds, and the like on stem cells, to elucidate the mechanism of certain diseases by determining changes in the biological activity of the stem cells (e.g., changes in KLF4, OCT4, SOX2, c-MYC or n-MYC or L-MYC, NANOG, Glis1 or any combination thereof expression or activity, proliferative capacity, adhesion), to study the mechanism by which drugs and/or growth factors operate to modulate stem cell biological activity (e.g., KLF4, OCT4, SOX2, c-MYC or n-MYC or L-MYC, NANOG, Glis1 or any combination thereof expression or activity), to diagnose and monitor cancer in a patient, for gene therapy, gene delivery or protein delivery; and to produce biologically active products.

The human induced pluripotent stem cells also can be used in the isolation and evaluation of factors associated with the differentiation and maturation of stem cells. Thus, the human induced pluripotent stem cells may be used in assays to determine the activity of media, such as conditioned media, evaluate fluids for cell growth activity, involvement with dedication of particular lineages, or the like. Various systems are applicable and can be designed to induced differentiation of the human induced pluripotent stem cells based upon various physiological stresses.

The human induced pluripotent stem cells, progeny thereof, and tissues derived therefrom of the disclosure may be used in vitro to screen a wide variety of agents for effectiveness and cytotoxicity of pharmaceutical agents, growth/regulatory factors, anti-inflammatory agents, and the like. To this end, the cells or tissue cultures of the disclosure can be maintained in vitro and exposed to the agent to be tested. The activity of a cytotoxic agent can be measured by its ability to damage or kill stem cells or their progeny in culture. This can be assessed readily by staining techniques. The effect of growth/regulatory factors can be assessed by analyzing the number of living cells in vitro, e.g., by total cell counts, and differential cell counts. This can be accomplished using standard cytological and/or histological techniques, including the use of immunocytochemical techniques employing antibodies that define type-specific cellular antigens. The effect of various drugs on the cells of the disclosure can be assessed either in a suspension culture or in a three-dimensional system. In one aspect, the effect of a test agent on the human induced pluripotent stem cells of the disclosure can be analyzed.

Stem cells which express a gene product of interest, or tissue produced in vitro therefrom, can be implanted into a subject who is otherwise deficient in that gene product. For example, genes that express products capable of preventing or ameliorating symptoms of various types of vascular diseases or disorders, or that prevent or promote inflammatory disorders are of particular interest. In one embodiment, the cells of the disclosure are genetically engineered to express an anti-inflammatory gene product that would serve to reduce the risk of failure of implantation or further degenerative change in tissue due to inflammatory reaction. For example, a stem cell of the disclosure can be genetically engineered to express one or more anti-inflammatory gene products including, for example, peptides or polypeptides corresponding to the idiotype of antibodies that neutralize granulocyte-macrophage colony stimulating factor (GM-CSF), TNF, IL-1, IL-2, or other inflammatory cytokines. IL-1 has been shown to decrease the synthesis of proteoglycans and collagens type II, IX, and XI (Tyler et al., 1985, Biochem. J. 227:69-878; Tyler et al., 1988, Coll. Relat. Res. 82:393-405; Goldring et al., 1988, J. Clin. Invest. 82:2026-2037; and Lefebvre et al., 1990, Biophys. Acta. 1052:366-72). TNF also inhibits synthesis of proteoglycans and type II collagen, although it is much less potent than IL-1 (Yaron, I., et al., 1989, Arthritis Rheum. 32:173-80; Ikebe, T., et al., 1988, J. Immunol. 140:827-31; and Saklatvala, J., 1986, Nature 322:547-49). Also, for example, the cells of the disclosure may be engineered to express the gene encoding the human complement regulatory protein that prevents rejection of a graft by the host. See, for example, McCurry et al., 1995, Nature Medicine 1:423-27. In another embodiment, the human induced pluripotent stem cells may be engineered to include a gene or polynucleotides sequence that expresses or causes to be expressed an angiogenic factor.

The induced stem cells of the disclosure express one or more markers associated with a human pluripotent stem cell phenotype and/or lack one or more markers associated with a differentiated cell (e.g., a cell having a reduced capacity for self-renewal, regeneration, or differentiation) and/or a cell of neuronal origin. A molecule is a "marker" of a desired cell type if it is found on a sufficiently high percentage of cells of the desired cell type, and found on a sufficiently low percentage of cells of an undesired cell type. One can achieve a desired level of purification of the desired cell type from a population of cells comprising both desired and undesired cell types by selecting for cells in the population of cells that have the marker. A marker can be displayed on, for example, 300, 35%, 40%, 45%, 50%, 55%, 60%, 65%, 70%, 75%, 80%, 85%, 90%, 95%, 99% or more of the desired cell type, and can be displayed on fewer than 50%, 45%, 40%, 35%, 30%, 25%, 20%, 15%, 10%, 5%, 1% or fewer of an undesired cell type.

As discussed above, the induced stem cells of the disclosure or induced stem cells that have been differentiated are characterized by the presence and/or the absence of certain markers that are specifically recognized by a molecule. Accordingly, in one aspect, the disclosure provides methods of labeling induced stem cells of the disclosure. In one embodiment, the human induced pluripotent stem cells are labeled with a molecule (e.g., an antibody) that specifically recognizes a marker that is associated with an induced stem cell of the disclosure. In another embodiment, a population of cells is contacted with a molecule that specifically binds to a marker (e.g., TRA-1-81) under conditions that allow the molecule to bind to the marker, wherein the population of cells comprises at least one stem cell having said marker. In another embodiment, a population of cells is contacted with a molecule that specifically binds to a marker under conditions that allow the molecule to bind to the marker, wherein the population of cells comprises stem cells that do not have the marker and non-stem cells that do have the marker. The molecule used can be, for example, an antibody, an antibody derivative, or a ligand. The molecule optionally can comprise an additional moiety, for example, one that is detectable (e.g., a fluorescent or colorimetric label) or one that aids in the isolation of the labeled cells (e.g., a moiety that is bound by another molecule or a magnetic particle).

In one embodiment, the population of transformed somatic cells undergoes live staining for a Tumor Rejection Antigen 1-61 and 1-81 (TRA-1-60, TRA-1-81). TRA-1-60 and TRA-1-81 may be obtained commercially, for example from Chemicon International, Inc (Temecula, Calif., USA). The immunological detection of these antigens using monoclonal antibodies has been used to characterize pluripotent stem cells in combination with other markers (Shamblott M. J. et al. (1998) PNAS 95: 13726-13731; Schuldiner M. et al. (2000). PNAS 97: 11307-11312; Thomson J. A. et al. (1998). Science 282: 1145-1147; Reubinoff B. E. et al. (2000). Nature Biotechlnology 18: 399-404; Henderson J. K. et al. (2002). Stem Cells 20: 329-337; Pera M. et al. (2000). J. Cell Science 113: 5-10.). In one embodiment, a population of somatic cells that have been transformed with at least one ectopic RNA vector comprising a KLF4, OCT4, SOX2, c-MYC or n-MYC or L-MYC, and optionally or alternatively NANOG or Glis1 are enriched for cells comprising TRA-1-81 or TRA-1-60 expression. In a further embodiment, the cells may also be enriched for the loss of a detectable marker associated with a retroviral vector.

In another aspect, the disclosure provides methods of isolating induced stem cells of the disclosure. The human induced pluripotent stem cells of the disclosure can be isolated by, for example, utilizing molecules (e.g., antibodies, antibody derivatives, ligands or Fc-peptide fusion molecules) that bind to a marker (e.g., a TRA-1-81, a TRA-1-60 or a combination of markers) on the human induced pluripotent stem cells and thereby positively selecting cells that bind the molecule (i.e., a positive selection). Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of stem cell can be made.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Conveniently, antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the human induced pluripotent stem cells. In one embodiment, the cells are incubated with an antibody against a marker (e.g., a TRA-1-81 antibody) and the cells that stain positive for the marker are manually selected and subcultured.

Combinations of enrichment methods may be used to improve the time or efficiency of purification or enrichment. For example, after an enrichment step to remove cells having markers that are not indicative of the cell type of interest the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, Texas red, and the like.

Any cell type-specific markers can be used to select for or against a particular cell type. Induced stem cell markers useful for enrichment comprise expressed markers such as TRA-1-81 and loss of markers (e.g., GFP) associated with a retroviral vector or other exogenous vector.

Once stem cells have been isolated, they optionally can be propagated in appropriate medium in the presence of absence of a feeder layer. In addition, the human induced pluripotent stem cells of the invention may be cultured in a bioreactor system.

Once the human induced pluripotent stem cells of the disclosure have been established in culture, as described above, they may be maintained or stored in cell "banks" comprising either continuous in vitro cultures of cells requiring regular transfer or cells which have been cryopreserved. In some embodiments, the banked cells are used for autologous treatment of a subject.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

The isolation of fibroblasts may, for example, be carried out as follows: fresh tissue samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown.

Where the de-differentiated cells are to be used for transplantation or implantation in vivo it is useful to obtain the stromal cells from the patient's own tissues.

Oligonucleotide probes and primers can be used to identify expression of various factors described herein as well as in cloning and amplification procedures. An oligonucleotide probe or a primer refers to a nucleic acid molecule of between 8 and 2000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the disclosure under a particular set of conditions may be empirically determined by one of skill in the art.

Oligonucleotide primers and probes can be prepared by any suitable method, including, for example, cloning and restriction of appropriate sequences and direct chemical synthesis based upon the known KLF4, OCT4, SOX2, c-MYC or n-MYC or L-MYC, NANOG or any combination thereof polynucleotide and polypeptide sequence. Various orthologs from other species are known in the art.

Oligonucleotide probes and primers can comprise nucleic acid analogs such as, for example, peptide nucleic acids, locked nucleic acid (LNA) analogs, and morpholino analogs. The 3' end of the probe can be functionalized with a capture or detectable label to assist in detection of a KLF4, OCT4, SOX2, c-MYC or n-MYC or L-MYC, NANOG, Glis1 or any combination thereof nucleic acid.

Any of the oligonucleotides or nucleic acid of the disclosure can be labeled by incorporating a detectable label measurable by spectroscopic, photochemical, biochemical, immunochemical, or chemical means. For example, such labels can comprise radioactive substances ($^{32}P$, $^{35}S$, $^{3}H$, $^{125}I$), fluorescent dyes (5-bromodesoxyuridin, fluorescein, acetylaminofluorene, digoxigenin), biotin, nanoparticles, and the like. Such oligonucleotides are typically labeled at their 3' and 5' ends.

The oligonucleotide primers and probes can be immobilized on a solid support. Solid supports are known to those skilled in the art and include the walls of wells of a reaction tray, test tubes, polystyrene beads, magnetic beads, nitrocellulose strips, membranes, microparticles such as latex particles, glass and the like. The solid support is not critical and can be selected by one skilled in the art. Thus, latex particles, microparticles, magnetic or non-magnetic beads, membranes, plastic tubes, walls of microtiter wells, glass or silicon chips and the like are all suitable examples. Suitable methods for immobilizing oligonucleotides on a solid phase include ionic, hydrophobic, covalent interactions and the like. The solid support can be chosen for its intrinsic ability to attract and immobilize the capture reagent. The oligonucleotide probes or primers can be attached to or immobilized on a solid support individually or in groups of about 2-10,000 distinct oligonucleotides of the disclosure to a single solid support. A substrate comprising a plurality of oligonucleotide primers or probes of the disclosure may be used either for detecting or amplifying KLF4, OCT4, SOX2, c-MYC or n-MYC or L-MYC, NANOG, Glis1 or any combination thereof. For example, the oligonucleotide probes can be used in an oligonucleotide chip such as those marketed by Affymetrix and described in U.S. Pat. No. 5,143,854; PCT publications WO 90/15070 and 92/10092, the disclosures of which are incorporated herein by reference. These arrays can be produced using mechanical synthesis methods or light directed synthesis methods which incorporate a combination of photolithographic methods and solid phase oligonucleotide synthesis. The disclosure further contemplates antibodies capable of specifically binding to a KLF4, OCT4, SOX2, c-MYC or n-MYC or L-MYC, NANOG, or Glis1 polypeptide.

A reference or control population refers to a group of subjects or individuals who are predicted to be representative of the general population. A test sample is measured for the amount of KLF4, OCT4, SOX2, c-MYC or n-MYC or L-MYC, NANOG, Glis1 or any combination thereof in the sample, wherein the amount is compared to a control sample.

In another aspect, the disclosure provides methods of differentiating stem cells along a committed lineage comprising inhibiting the expression or activity of KLF4, OCT4, SOX2, c-MYC or n-MYC or L-MYC, NANOG, Glis1 or any combination thereof. Differentiation agents useful in this regard include, for example, antibodies, antisense oligonucleotides, RNAi constructs, or ribozymes.

Culture techniques useful in the methods of the disclosure are disclosed in International Patent Publication No. WO 2010/120785, which is incorporated herein by reference.

The following Examples are provided to illustrate certain aspects of the disclosure and to aid those of skill in the art in practicing the disclosure. These Examples are in no way to be considered to limit the scope of the disclosure in any manner.

EXAMPLES

Example 1

Cells.

BJ foreskin fibroblasts and STO cell line were obtained from ATCC. Primary human foreskin fibroblasts (HFF) and HUES-9 human ES cell line were obtained from existing sources. BJ, HFFs and STO were cultured in DMEM containing 10% FBS, MEM Non-Essential Amino Acids (NEAA), Pyruvate, penicillin, and streptomycin. HUES-9 and iPS cells were cultured with ES culture medium in Knockout D-MEM containing 20% Knockout SR, GlutaMAX, NEAA, 2-Mercaptoethanol (all from Invitrogen), penicillin, streptomycin, and bFGF (10 ng/ml). STO feeder cells were prepared by mitomycin C treatment (10 μg/ml, Sigma). For feeder free culture of iPS cell clones and HUES-9, cells were passaged on Matrigel™ (BD Bioscience) coated wells and cultured in the conditioned medium prepared from STO feeder cells with ES culture medium.

Plasmid Construction.

cDNAs coding for OCT4 (accession no. NM_002701), c-MYC (accession no. NM_002467) and GLIS1 (accession no. BC104911) were obtained from Open biosystems. SOX2 (accession no. NM_003106), KLF4 (accession no. NM_004235), NANOG (accession no. BC099704) are available from ATCC. B18R (accession no. D01019) was obtained from Addgene. The polynucleotide and polypeptide sequences associated with each of the foregoing accession nos. are incorporated herein by reference. The cDNAs were used as templates for PCR amplification to add restriction enzyme sites and/or Kozak sequence, and cloned into pBluescript SK+ vector for checking of cDNA sequences. Then cDNAs were cloned into pTNT vector (Promega) for mRNA synthesis and pCX4bsr1 for the retrovirus production. For the multicistronic expression using viral 2A peptide sequences, F2A oligos, T2A oligos and E2A oligos (Table 1) were annealed and cloned into EcoRI/SpeI, SpeI/XbaI and XbaI/NotI sites of pBluescript SK+ vector, respectively. cDNAs of reprogramming factors were linked with 2A peptide sequences in frame, and then cloned into pVEE-S-IRES-Puro. pVEE-S-IRES-Puro were constructed from p5'VEE/S/GFP/Pac3 to clone reprogramming factors. Briefly, GFP/Pac genes and partial 3'UTR in p5'VEE/S/GFP/Pac were deleted with XbaI/MfeI digestion, and then introduced the multiple cloning sites (MCS; NdeI, AscI, BbvCI, ClaI, MfeI, FseI and NotI) (Table 1), IRES and Puromycin resistance gene from pCX4puro. This vector was renamed as pVEE-IRES-Puro for convenience. To generate RNA with T7 RNA polymerase, the SP6 promoter (ATTTAGGTGACACTATAG (see, e.g., SEQ ID NO:31 from 16844-16861)) was replaced to T7 promoter (TAATACGACTCACTATAG (see, e.g., SEQ ID NO:32 from 16843-16860)) by PCR (Table 1) using the SacI/BstZ17I fragment of VEE vector as a template (SP6 promoter is located on next to the SacI site).

TABLE 1

| PCR Cloning Primers | | |
|---|---|---|
| F2A-Forward | 5'-AATTCACCGGTGTGAAACAGACTTTGAATTTTGACCTTCTCAAGTTGG CGGGAGACGTGGAGTCCAACCCAGGGCCCAGATCTA (SEQ ID NO: 11) | F2A-oligo |
| F2A-Reverse | 5'-CTAGTAGATCTGGGCCCTGGGTTGGACTCCACGTCTCCCGCCAACT TGAGAAGGTCAAAATTCAAAGTCTGTTTCACACCGGTG (SEQ ID NO: 12) | F2A-oligo |
| T2A-F | 5'-CTAGTGAGGGCAGAGGAAGTCTGCTAACATGCGGTGACGTCGAGG AGAATCCTGGCCCACAATTGT (SEQ ID NO: 13) | T2A-oligo |
| T2A-R | 5'-CTAGACAATTGTGGGCCAGGATTCTCCTCGACGTCACCGCATGTTA GCAGACTTCCTCTGCCCTCA (SEQ ID NO: 14) | T2A-oligo |
| E2A-F | 5'-CTAGACAATGTACTAACTACGCTTTGTTGAAACTCGCTGGCGATGTT GAAAGTAACCCCGGTCCTGGCGCGCCCGC (SEQ ID NO: 15) | E2A-oligo |
| E2A-R | 5'-GGCCGCGGGCGCGCCAGGACCGGGGTTACTTTCAACATCGCCAGC GAGTTTCAACAAAGCGTAGTTAGTACATTGt (SEQ ID NO: 16) | E2A-oligo |
| VEE-MCS-F1 | 5'-CTAGCATATGGGCGCGCCCTCAGCATCGATGGCCGGCCTCTAGAGC GGCCGC (SEQ ID NO: 17) | MCS-oligo |
| VEE-MCS-R1 | 5'-GGCCGCGGCCGCTCTAGAGGCCGGCCATCGATGCTGAGGGCGCGC CCATATG (SEQ ID NO: 18) | MCS-oligo |
| nsP2a-F1 | 5'-CAGGACGATCTCATTCTCAC (SEQ ID NO: 19) | PCR, nsP2 |
| nsP2a-R1 | 5'-GCTTGCCACTCCTCTATCGTG (SEQ ID NO: 20) | PCR, nsP2 |
| nsP4a-F1 | 5'-CCACAATACGATCGGCAGTG (SEQ ID NO: 21) | PCR, nsP4 |
| nsP4a-R1 | 5'-ATGTCCTGCAACATATTCAAA (SEQ ID NO: 22) | PCR, nsP4 |
| hOct4RTa-F1 | 5'-CGGCGCCAGAAGGGCAAGCG (SEQ ID NO: 23) | PCR, OK |
| hKlf4RTb-R1 | 5'-CACCTGCTTGACGCAGTGTC (SEQ ID NO: 24) | PCR, OK |
| hKlf4GC2For | 5'-GCAGGAGGCGGTCTCTTCGTGCACC (SEQ ID NO: 35) | PCR, Klf4 |
| hKlf4GC2Rev | 5'-CAGGTGTGCCTTGAGATGGGAACTC (SEQ ID NO: 36) | PCR, Klf4 |
| Bis-Oct-10F | 5'-GGAGTAGAAGGATTGTTTTGGTTTA (SEQ ID NO: 25) | bisulfite, |
| Bis-Oct-9R | 5'-AAACCTTAAAAACTTAACCAAATCC (SEQ ID NO: 26) | bisulfite |
| Bis-Nanog-4F | 5'-AGAGTAGTTGGGATTATAGATATTTA (SEQ ID NO: 27) | bisulfite |

TABLE 1-continued

| PCR Cloning Primers | | |
|---|---|---|
| Bis-Nanog-3R | 5'-AACAACAAAACCTAAAAACAAACC (SEQ ID NO: 28) | bisulfite |
| EcoR1-Sac1-T7M1-VEE | 5'-CGGAATTCGAGCTCTAATACGACTCACTATAGATGGGCGGCGCATGAGAGAAGCCCAG (SEQ ID NO:37) | T7 VEE PCR |
| Xba1-BstZ17I-VEE | 5'-GCTCTAGAGTATACATCCTGGTAAACAGCGACTTGCCC (SEQ ID NO: 38) | T7 VEE PCR |

mRNA and Replicon RNA Synthesis.

pTNT-B18R plasmid was used for the synthesis of B18R mRNA. The pTNT vector contains a 5' β-globin leader sequence and a synthetic poly (A) tail (30 bases) to enhance the expression of genes. 30 bases of poly(A) were not enough to stabilize mRNA, so additional poly(A) tail was added by poly(A) tail polymerase. B18R-mRNA synthesis was performed with modified nucleotides using the RiboMAX Large Scale RNA Production System-SP6 (Promega) kit. Modification was performed with replacement of 100% of UTP with psuedouridine (Psi) (TriLink Biotechnologies) or 25% of UTP and CTP with Psi and 5-methylcytidine (5mc) (TriLink Biotechnologies), respectively. After the transcription reaction, DNA template was removed by DNase digestion. The mRNA was purified by extraction with Phenol/Chloroform/Isoamyl alcohol (PCI) and Chloroform/Isoamyl alcohol (CI), and then concentrated by ammonium acetate precipitation (2.5 M), which is selectively precipitates RNA, while leaving most of the protein, DNA and unincorporated NTPs in the supernatant according to the manufacture's protocol (Epicentre). Typically 10 μg of linearized plasmid for 100 μl reaction scale was used and received about 400 μg mRNA. For the 5'-Capping of mRNA, ScriptCap m7G Capping System™ was used and ScriptCap 2'-O-Methyltransferase (Epicentre, currently available from CELLSCRIPT) to produce cap 1-capped RNA, which proceeds to quantitative completion of capping. After 5'-Capping, mRNA was briefly purified by ammonium acetate precipitation, and then additional poly(A) tail was added by Poly(A) Polymerase (Epicentre, currently available from CELLSCRIPT). The mRNA bearing 5'-Capping and poly(A) tail was purified by extraction with PCI and CI, followed by ammonium precipitation. For the synthesis of replicon RNA, template plasmid was linearized by digestion with MluI, and then used for RNA synthesis in the same way with mRNA synthesis. The synthesis of RNA replicon was performed without RNA modification. After the DNase treatment, the synthesized RNA was purified by ammonium acetate precipitation without organic purification because most of large RNA was trapped into intermediate phase after organic extraction. The replicon RNA was added 5'-Capping and poly(A) tail as described above, and then purified by ammonium acetate precipitation without organic purification. All RNAs were resuspended in the RNA Storage Solution (Ambion) at 1 μg/μl concentration and stored at −80° C. until use.

Preparation of B18R Conditioned Medium (B18R-CM).

25% double modified B18R mRNA (1 μg for 1 well of 6-well plate) was transfected into HFFs with Lipofectamine 2000 (Invitrogen). After 3 hr, cells were cultured in Advanced DMEM (Invitrogen) containing 15% FCS (ES cell qualified, Millipore), penicillin, and streptomycin, or ES culture medium. Culture medium was collected on next day, filtrated, and diluted into 5 times with cell culture medium, and then used as B18R-CM (20% B18R-CM). The activity of B18R-CM was briefly measured by the efficiency of repeated transfection of mRNAs.

iPS Generation by Replicon Transfection.

BJ or HFFs were passaged to 6-well plate on day-0 and cultured to ~90-100% confluency ($4\times10^5$ cells/well) on day-1. 1 μg RNA mixture (3:1 ratio VEE RNA Replicon to B18R mRNA) was transfected with Lipofectamine 2000. 25% double modified B18-mRNA or 100% Psi modified mRNA were used for co-transfection. After 3 hr, transfection medium was changed to the Advanced DMEM (Invitrogen) containing 15% FCS (ES cell qualified, Millipore), penicillin, and streptomycin. Cells were cultured in medium containing B18R-CM and puromycin (0.8 μg/ml) from day-2. Medium was changed every day and transfections were performed every 3 days (day-1, 4, 7, 10 or 14). ES medium was used from day-7. Puromycin was removed at day-7 or day-11. One day after the final transfection, cells were passaged to STO feeder and cultured in ES medium containing B18R-CM. ES medium was changed every day and cultured until iPS cell colonies were generated. Colonies were mechanically picked for isolation of clones or stained with Alkaline Phosphase Detection kit (Millipore) or manually prepared AP-staining solution containing 1 mg/ml of FastRed TR (Sigma) and 0.4 mg/ml of 1-Naphthyl phosphate (Sigma) in AP buffer (100 mM Tris, 100 mM NaCl and 50 mM $MgCl_2$, pH 9.5)

RT-PCR for the Detection of RNA Replicon.

Total RNAs were isolated with RNeasy mini kit (Qiagen) or TRIzol (Invitrogen). TRIzol purified RNAs were then purified with ammonium acetate precipitation. Synthesis of cDNAs was performed with QuantiTect Rev. Transcription Kit (Qiagen) or iScript cDNA synsethis kit (Bio-Rad) from 1 μg of total RNA. 1-2 μl of 20 μl RT reaction was used for PCR amplification. PCR was performed with Taq DNA plolymerase (NEB) supplemented with PCRx enhancer (Invitrogen): 3 min at 94° C. for initial denature; 36 cycles of 94° C. for 25 sec, 56° C. for 25 sec, 68° C. for 30 sec; followed by 72° C. for 5 min. Primer sequences used RT-PCR were described in Table 1.

TagMan RT-PCR.

Total RNAs from feeder free culture of iPSCs clones, HUES-9, BJ and HFFs were isolated with RNeasy mini kit. TaqMan RT-PCR reactions were carried out using RNA-to-Ct one-step reaction (Applied Biosystem) according to manufacturer's protocol. 10 ng of total RNA were used per reaction. Primers and probes were obtained from AB TaqMan Gene Expression Assay catalog (GAPDH, Hs99999905_m1; POU5F1 Hs03005111_g1; Sox2 Hs01053049_s1; DNMT3B Hs00171876_m1; TERT Hs00972656_m1; Lin28 Hs00702808_s1; Nanog Hs02387400_g1; TDGF1 Hs02339499_g1). Quantitative PCR reactions were carried out in triplicate, and conditions were as followed: 20 min 55° C., 10 min 95° C., 40 cycles of 95° C. for 0.15 min, 65° C. for 1 min. Data were analyzed on the 7300 real-time PCR system (Applied Biosystems) using the delta-delta Ct method.

Bisulfite Genomic Sequencing.

Conversion of unmethylated cytosines into urasil of genomic DNA was performed with EZ DNA Methylation-Gold Kit (Zymo Research) according to manufactor's protocol. Converted genomic DNAs were then used for PCR amplification of promoter region of OCT4 or NANOG with ZymoTaq™ DNA Polymerase (Zymo Research). PCR products were cloned into the T-vector from pBluescript SK+, and then sequenced. Primer sequences used for PCR were described in Table 1.

Teratoma Formation.

iPSC clones were cultured with STO feeder cells. Cells were collected by accutase treatment, and then intramuscularly or subcutaneously injected into the hind limb muscles or dorsal flank of nude mice (approximately 10 cm dish cultured cells for 1 shot of injection). After 5 to 8 weeks of injection, tumors were dissected and fixed with 4% paraformaldehyde. Tumors were embedded into paraffin, and sectioning, and then hematoxilin and eosin (H&E) staining or immunostaining of three germ layers markers was performed. AE1/AE3 (cytokeratin), NF-1 (neuronal cells) and GFAP (neuronal cells) were used for markers of ectoderm, Desmin (muscle cells) for marker of mesoderm, and AFP (primitive and definitive endoderm) for marker of endoderm.

Immunofluorescence Staining.

Cells were washed twice in PBS and fixed in 4% paraformaldehyde for 10 min. Washed cells were treated with 0.1% Triton X-100 in PBS for 10 min. Cells were blocked with 2% BSA for 1 hr at room temperature (RT), and then incubated with primary antibodies in PBS at 4° C. overnight. Cells were washed and incubated with secondary antibodies followed by incubation with DAPI or Hoechst 33342, and then washed and stored in PBS. Primary antibodies such as rabbit anti-Oct4, goat anti-Nanog and anti-Sox2, mouse anti-SSEA4, anti-Tra-1-60 and anti-Tra-1-81 antibodies were used at 1:100 to 1:500 dilutions. Alexa Fluor 488 (BD Biosciences) secondary antibodies were used at 1:800 dilutions.

Antibodies.

Antibodies used in this research are as follows; anti-OCT4 (sc-9081), anti-KLF4 (sc-20691), anti-GLIS1 (sc-67584), anti-c-MYC (sc-42), anti-LIN28 (sc-54030), TRA-1-60 (sc-21705), SSEA1 (sc-21702) and SSEA4 (sc-21704) from Santa Cruz; anti-SOX2 (AF2018) and anti-NANOG (AF1997) from R&D Systems; TRA-1-81 (09-0011) from Stemgent; AE1/AE3 (RB-9010P0), Desmin (MS-376-S0), AFP (RB-365) and GFAP (RB-087) from Labvision; NF-1 (NB-300-155) from Novus Biological.

RNA Sequence.

Total RNAs were isolated with RNeasy mini kit (Qiagen), and cDNA library of each cells were synthesized and analyzed as known in the art.

To develop an RNA-based iPS generation strategy, efforts were focused on an approach that: 1) utilized a single RNA species capable of self-replicating for a limited number cell divisions, thereby reducing the number of transfections; 2) was capable of encoding at least four reprogramming factor open reading frames (ORFs); and 3) consistently expressed all four RF genes at high threshold levels over multiple cellular divisions. To ectopically express all four RFs, a modified non-infectious, self-replicating, Venezuelan Equine Encephalitis (VEE) virus RNA replicon was used that is currently being investigated as an expression platform for vaccine development. The VEE replicon is a positive-strand, single RNA species that mimics cellular mRNA with a 5'-Cap and poly(A) tail that does not utilize a DNA intermediate, so there is no potential for genomic integration. VEE encodes four non-structural replication complex proteins (nsP) as a single ORF in the 5' end of the RNA that is separated from the viral structural protein ORF in the 3' end (FIG. 1*a*). Petrakova et al. showed the ability to express exogenous proteins by replacing the 3' structural proteins ORF with GFP. However, exposure of cells to single stranded VEE RNA induces a strong IFN-alpha/beta innate immune response that has severely limited this approach.

To evaluate the VEE RNA replicon, the 3' ORF was replaced with GFP, followed by an internal ribosomal entry site (IRES) and a Puromycin resistance gene (Puror) (FIG. 1*a*). VEE-GFP RNA was produced using a standard SP6 polymerase in vitro transcription kit followed by 5'-capping, and poly(A) tail addition resulting in a high yield, full length 11,500 nt RNA transcript. To mitigate the innate immune response to VEE-GFP RNA, the B18R protein from Western Vaccinia virus was used, which binds to and neutralizes type I IFNs. A comparison of transfection of primary human foreskin fibroblasts (HFFs) with VEE-GFP RNA alone was performed, in the presence of recombinant B18R protein or with co-transfection of B18R mRNA. Consistent with induction of a strong innate immune response to cells exposed to single stranded RNA, in the absence of B18R, little to no GFP expression was observed (FIG. 1*b*). Although addition of recombinant B18R protein increased GFP expression, the GFP fluorescence level was very low. However, co-transfection of VEE-GFP RNA replicon with B18R mRNA resulted in high levels of GFP expression in HFFs (FIG. 1*b-d*), showing that B18R is required for efficient expression of proteins from the VEE RNA replicon.

Figure 1D:
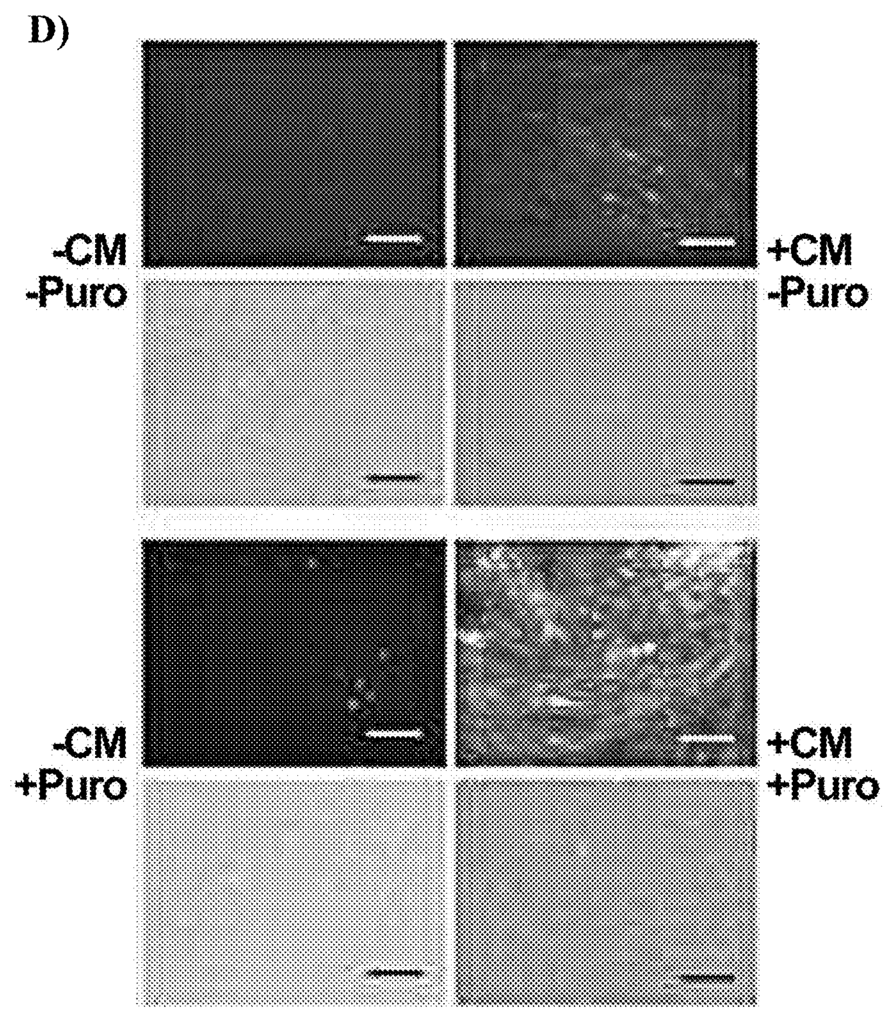
Figure 1E:
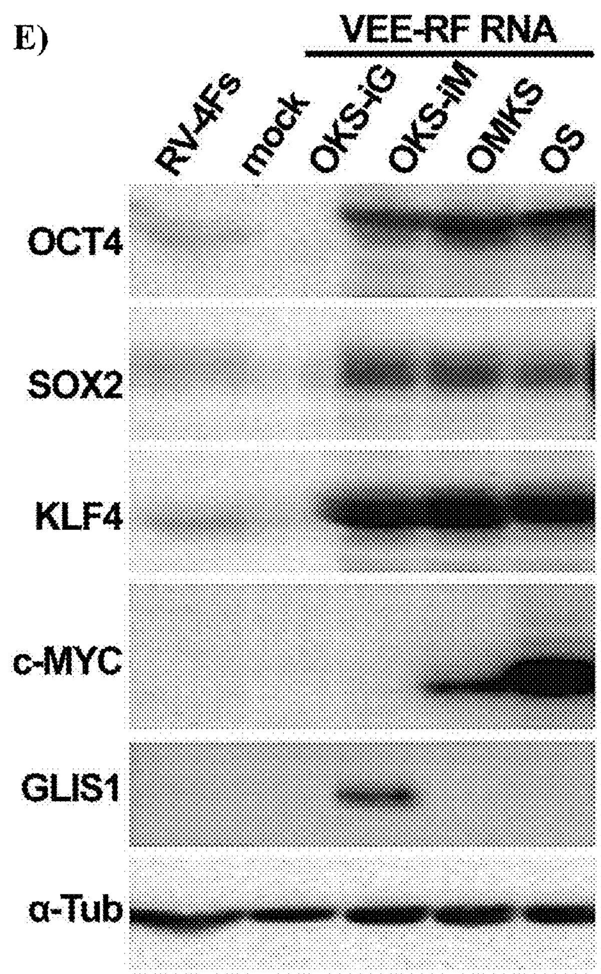

The generation of iPS cells requires consistent, high level expression of reprogramming factors for >7 days; therefore, the persistence of the VEE-GFP replicon in fibroblasts was examined. HFFs were co-transfected with VEE-GFP RNA replicon and B18R mRNA (3:1 ratio) on day 1, then cultured in the presence or absence of B18R conditioned media (CM) plus/minus puromycin on day 2. Although untreated VEE-GFP RNA/B18R mRNA transfected cells showed a high level of GFP expression on day 1, the expression level was rapidly reduced over the next several days to baseline values by day 7 (FIG. 1*e*). Moreover, in the absence of continuous B18R-CM exposure, VEE-GFP RNA transfected cells stopped growing and/or were killed by the innate immune response (FIG. 1*d*). In contrast, B18R-CM/puro treated VEE-GFP RNA/B18R mRNA transfected cells maintained persistent high levels of GFP expression in >90% of cells with healthy growth characteristics (FIG. 1*d,e*). These results showed the ability of B18R exposure to overcome the VEE RNA-induced innate immune response problem and also demonstrated the ability to selectively retain or degrade the VEE RNA replicon from cells by exposure or withdrawal of B18R-CM.

The VEE RNA replicon 3' ORF was engineered to encode a single combined ORF of three reprogramming factors, OCT4, KLF4, SOX2, separated by internal ribosomal skipping 2A peptides. The ORFs were followed by an IRES then either c-MYC (OKS-iM) or GLIS18 (OKS-iG), which avoids the genomic instability induced by c-MYC, followed by a second IRES and the Puromycin resistance gene (Puror) (FIG. 1*a*; Table 1). Similar to the VEE-GFP RNA protocol, VEE-RF RNAs were produced by SP6 in vitro transcription, 5'-capping, and poly(A) tail addition resulting in a high yield, full length ~14,500 nt VEE-OKS-iM RNA or ~15,000 nt VEE-OKS-iG RNA. Co-transfection of VEE-OKS-iM RNA or VEE-OKS-iG RNA replicons plus B18R mRNA (3:1 ratio) into BJ or HFF human fibroblasts resulted in extended high levels of expression of all four RFs that exceeded RF expression levels from retroviruses (FIG. 1*f*). These observations demonstrated the ability to express four reprogramming factors from a single, synthetic VEE-RF RNA replicon in primary human cells, while utilizing B18R to block the innate immune response.

Figure 2A:
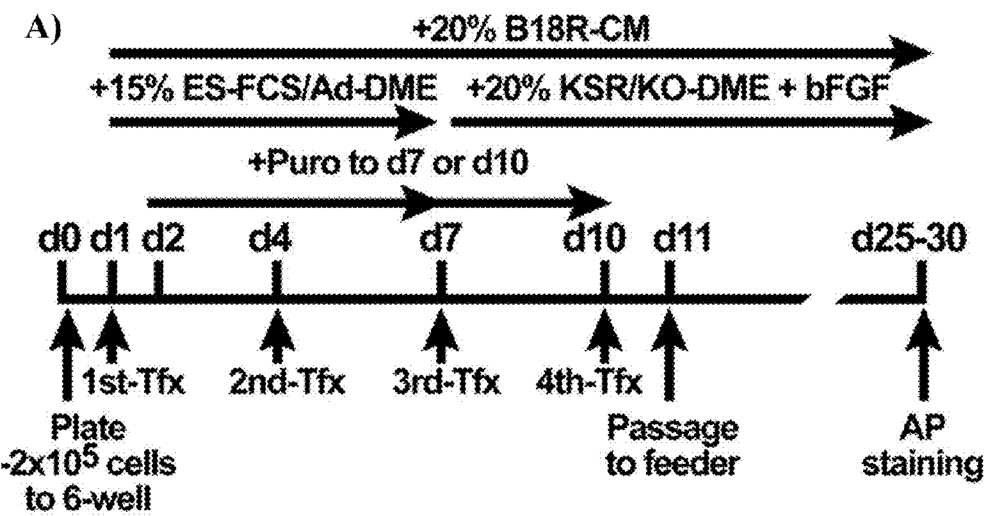
Figure 2E:
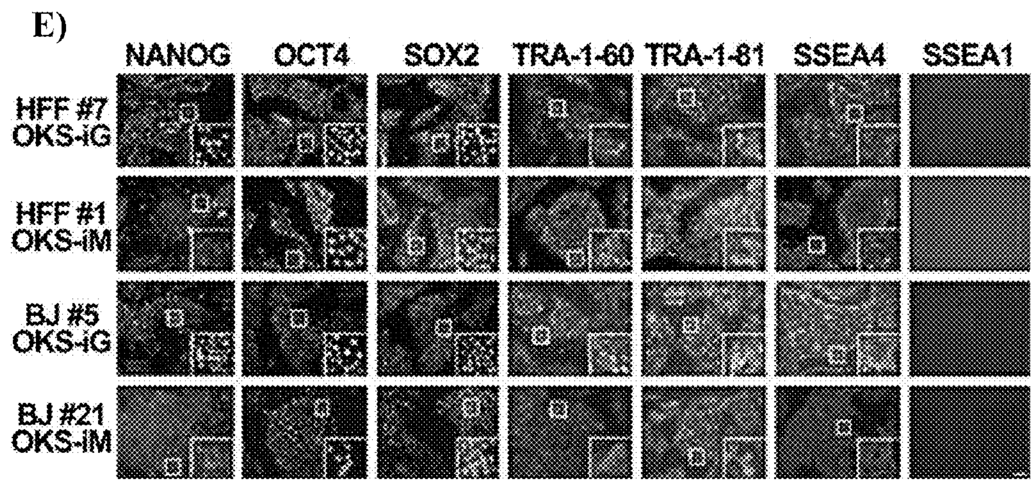

To develop an RNA-based generation iPS cell protocol, several parameters were evaluated, including number and timing of VEE-RF RNA transfections, selection for VEE-RF RNA replicon retention by puromycin, and the genetic organization of the VEE-RF RNA replicon (FIG. 1*a*, 2*a*). Although even a single or double transfection of RF-RNA resulted in iPS cell generation, three or four transfections in the presence of B18R consistently resulted in the highest generation of Alkaline Phosphatase positive (AP+) colonies (FIG. 2*b-d*). >100 iPS cell colonies were mechanically isolated from the VEE-OKS-iM and VEE-OKS-iG RNA protocols and had a >95% success rate for the ability of isolated iPS-like clones to continuously divide and retain a human embryonic stem cell (hESC) morphology. Of the >100 iPS-like clones isolated, 30 clones were isolated for expression of stem cell markers by immunofluorescence. All 30 VEE RF-RNA iPS clones analyzed (6× HFF-OKS-iM clones, 12× BJ-OKS-iM clones, 6× HFF-OKS-iG clones, 6× BJ-OKS-iG clones) showed strong nuclear staining of endogenous OCT4, SOX2 and NANOG, and strong cell surface staining of SSEA4, TRA-1-60 and TRA-1-81, with negative staining of SSEA1 (FIG. 2*e*). To eliminate the VEE-RF RNA replicon, all iPS protocols removed B18R-CM and puromycin on day 7 or 10 during reprogramming (FIG. 2*a*). To confirm the complete loss of VEE RF-RNA replicons, a highly sensitive and specific qRT-PCR protocol was developed capable of detecting <10 femtogram of the VEE RF-RNA replicon (FIG. 4). As expected, qRT-PCR analysis showed that all iPS cell clones had lost the VEE RF-RNA replicon (Table 2). Moreover, karyotype analysis of 4 independent iPS cell clones (BJ-OKS-iM #2 & #21, BJ-OKS-iG #5, HFF-OKS-iM #1) showed normal diploid karyotypes (FIG. 5).

TABLE 2

Detection of RF-RNA replicon by qRT-PCR

| | Passage # | | | | | | | Tfx times | |
|---|---|---|---|---|---|---|---|---|---|
| | P4 | P5 | P6 | P7 | P8 | P9 | P11 | | |
| [a]Clones | [b]R1R2R3 | R1R2R3 | R1R2R3 | R1R2R3 | R1R2R3 | R1R2R3 | R1R2R3 | [c]PL | [d]FD |
| BJ-iM-1 | | + + + | | | – – – | | – – ND | 5 | 2 |
| BJ-iM-2 | | – + +/– | | | – – – | | | 5 | 2 |
| BJ-iM-3 | | – – +/– | | | – – – | | | 5 | 2 |
| BJ-iM-14 | | – – – | | | – +/– – | | – – ND | 1 | 2 |
| BJ-iM-15 | | – – – | | | – – – | | | 1 | 2 |
| BJ-iM-16 | | – – – | | | – – – | | | 1 | 2 |
| BJ-iM-20 | | – – – | | | | – – – | | 5 | 0 |
| BJ-iM-21 | | – + – | | – +/– +/– | | – – – | | 5 | 0 |
| BJ-iM-22 | | – – – | | | | – – – | | 5 | 0 |
| BJ-iM-23 | | – – – | | | | – – – | | 5 | 0 |
| BJ-iM-24 | | – + – | | – – – | | – – – | | 2 | 0 |
| BJ-iM-25 | | – – – | | | | – – – | | 2 | 0 |
| HFF-iM-1 | + + ND | | – – – | | – – – | | | 2 | 2 |
| HFF-iM-2 | + + ND | | – + + | | – – – | | | 2 | 2 |
| HFF-iM-3 | + + ND | | | | – – – | | | 2 | 2 |
| HFF-iM-4 | – + – | | – – – | | – – – | | | 2 | 2 |
| HFF-iM-5 | – – – | | – – – | | – – – | | | 2 | 2 |
| HFF-iM-6 | + + + | | – +/– – | | – – – | | | 2 | 2 |
| HFF-iM-7 | + + ND | | | | – – – | | | 5 | 2 |
| HFF-iM-8 | + + ND | + + ND | | | – – – | | | 5 | 2 |
| HFF-iM-9 | – + ND | +/– +/– ND | | | – – – | | | 5 | 2 |
| HFF-iM-10 | + + + | | – +/– +/– | | – – – | | | 5 | 2 |
| HFF-iM-11 | – – – | | – – – | | – – – | | | 5 | 2 |
| HFF-iM-12 | – – – | | – – – | | – – – | | | 5 | 2 |
| BJ-iG-1 | – – – | | – – – | | – – – | | | 5 | 0 |
| BJ-iG-2 | – – – | | – – – | | – – – | | | 5 | 0 |
| BJ-iG-3 | – – – | | – – – | | – – – | | | 5 | 0 |
| BJ-iG-4 | – – – | | – – – | | – – – | | | 5 | 0 |
| BJ-iG-5 | – – – | | – – – | | – – – | | | 5 | 0 |
| BJ-iG-6 | – +/– – | | – – – | | – – – | | | 5 | 0 |
| HFF-iG-7 | – – – | | – – – | | – – – | | | 4 | 0 |
| HFF-iG-8 | – +/– – | | – – – | | – – – | | | 4 | 0 |
| HFF-iG-9 | – – – | | – – – | | – – – | | | 4 | 0 |
| HFF-iG-10 | – +/– – | | – +/– – | | – – – | | | 4 | 0 |
| HFF-iG-11 | – – +/– | | – +/– – | | – – – | | | 4 | 0 |
| HFF-iG-12 | – – – | | – – – | | – – – | | | 4 | 0 |

[a]iM indicates clones from OKS-iM RNA replicon., iG indicates clones from OKS-iG RNA replicon.

Figure 3A:
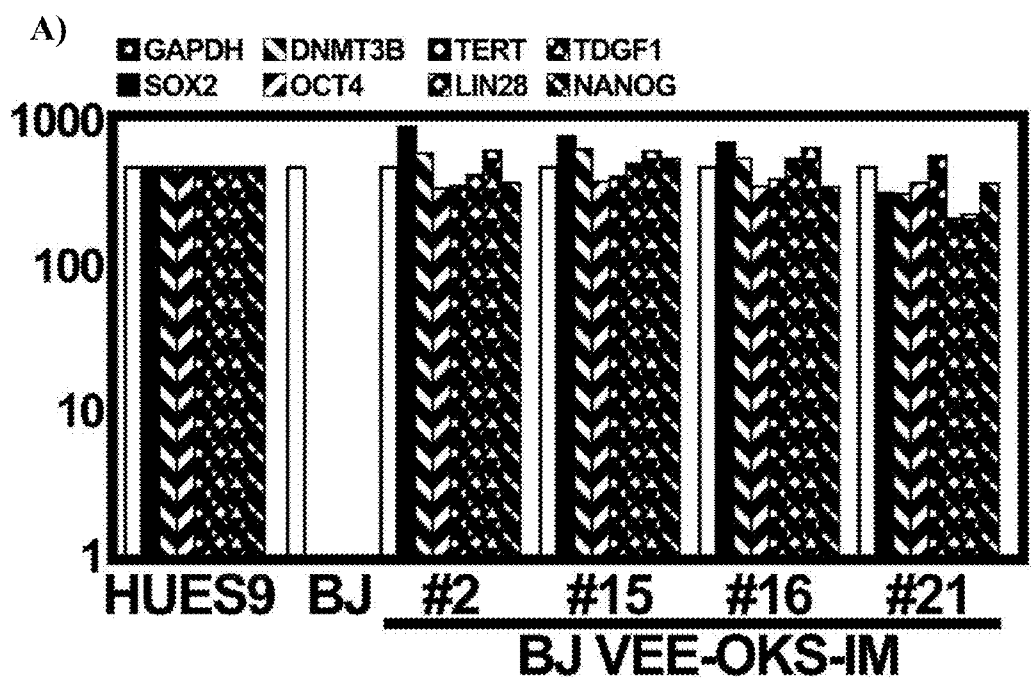
Figure 3A:
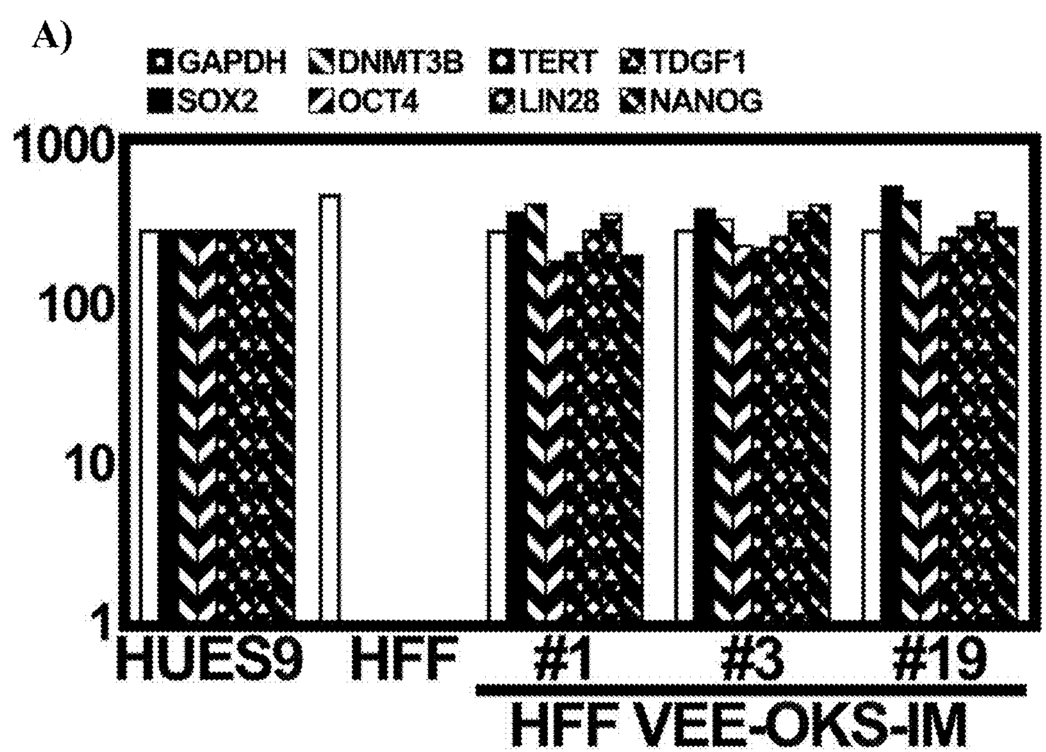
Figure 3B:
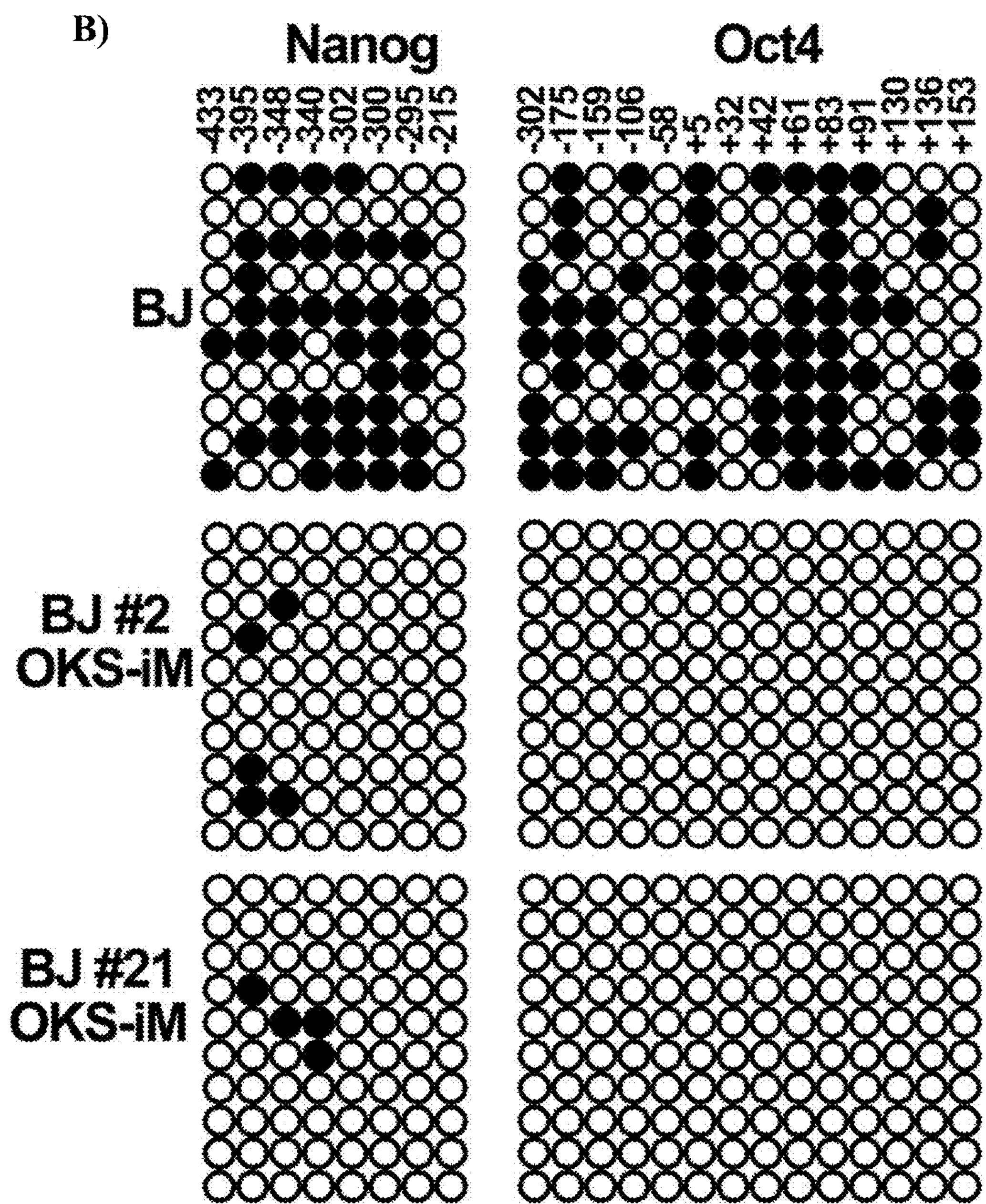
Figure 3C:
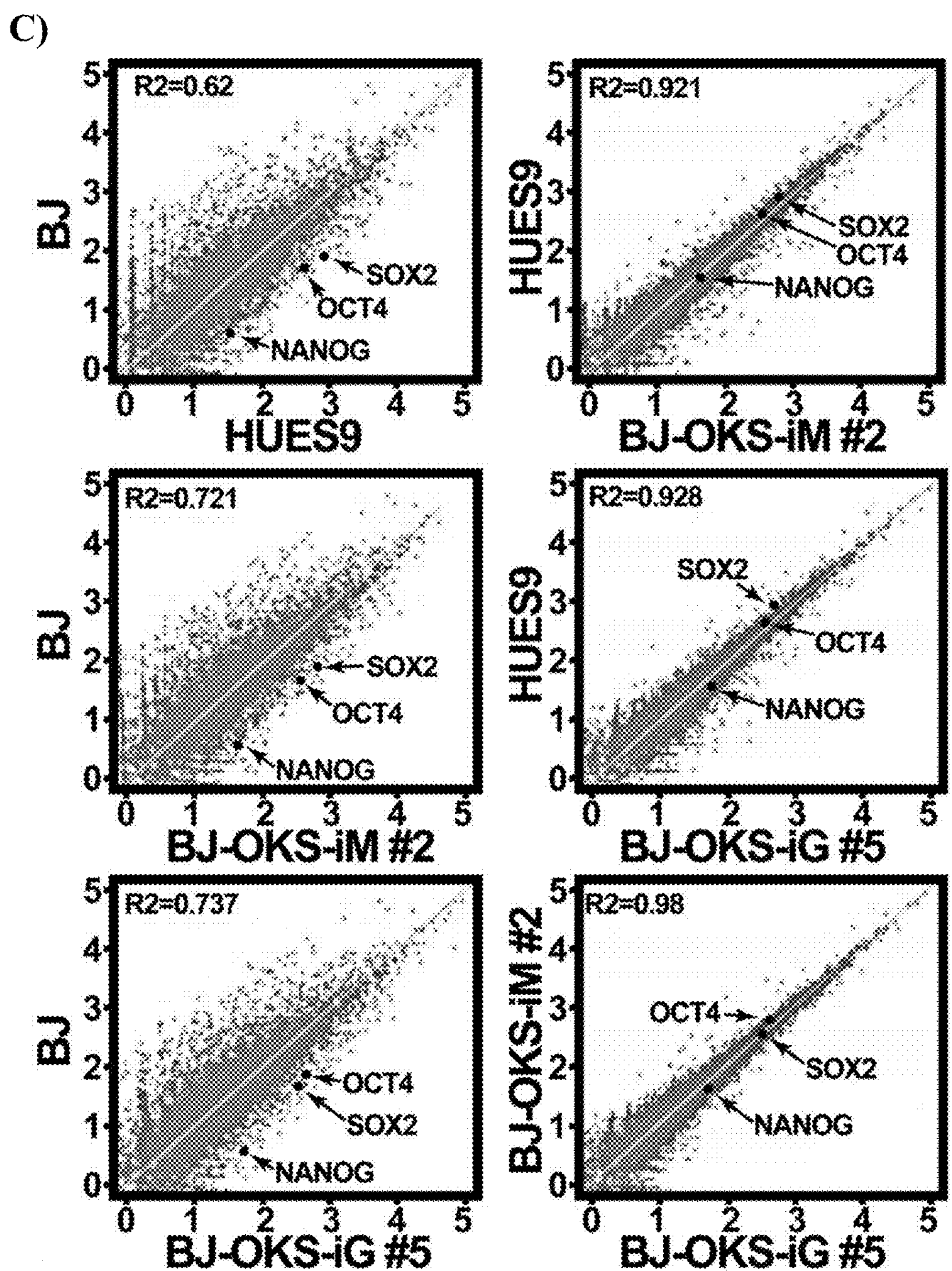

[b]regions for RT-PCR, R1; nsP2, R2; nsP4, R3; Oct4-T2A-Klf4 (OK),

[c]transfection on plate (PL) before passaging to feeder cells,

[d]transfection after passaging to feeder cells (FD). +; positive band detected, +/–; faint band detected, –; no band detected. ND; not done To further characterize the established iPS cell clones, the expression of human ES marker genes by qRT-PCR was analyzed. Consistent with expression levels in human HUES9 ES cells, iPS clones generated from both parental BJ and HFF fibroblasts with either the OKS-iM or OKS-iG VEE-RF RNA protocol expressed robust levels of endogenous OCT4, SOX2, NANOG, LIN28, TDGF1, DNMT3B and TERT, in contrast to low or no expression levels in starting parental BJ and HFF fibroblasts (FIG. 3*a*). A hallmark of induced pluripotency is reduced DNA methylation of CpG dinucleotides in the OCT4 and NANOG promoter regions. Bisulfite genomic sequencing of both the OCT4 and NANOG promoter regions showed extensive demethylation in iPS cell clones compared to parental fibroblasts (FIG. 3*b*). To investigate genome-wide mRNA expression profiles in iPS cell clones, whole genome RNA sequencing (RNA-seq) was performed of OKS-iM and OKS-iG VEE-RF RNA generated iPS cell clones, parental BJ and HUES-9 ES cell controls. All four iPS cell clones analyzed by RNA-seq showed unsupervised hierarchical clustering and expression signatures characteristic of human HUES9 ES cells that were highly divergent from parental human fibroblasts (FIG. 3*c,d*). Lastly, the in vivo pluripotency of human iPS cell clones were tested for their ability to differentiate into cells of all three germ layers by teratoma formation in immunocompromised mice. All of the VEE-RF RNA iPS clones analyzed formed teratomas containing representative cell types from the three germ layers, detected by H&E staining that were confirmed by immunohistochemistry staining (FIG. 3*e*; FIG. 6). Collectively, these observations confirm the ability of both OKS-iM and OKS-iG VEE RF-RNA replicons to efficiently generate pluripotent human iPS cells.

The generation of iPS cells has great potential for the development of personalized stem cell therapies; however, a straightforward and consistent RNA-based method to generate iPS cells has remained elusive. The disclosure provides a simple, highly reproducible RNA-based approach to generate iPS cells by transfection of a single, synthetic VEE-RF RNA replicon that expresses one, two, three, four or more independent reprogramming factors. VEE-RF RNA generated iPS cells acquired full pluripotency by rigorous in vivo biological and molecular criterion that paralleled human ES cells. The generation of the VEE RF-RNA transcript utilizes a standard SP6 in vitro transcription kit that does not require special conditions and thereby, further simplifies the approach for broad use. By expressing the four RFs at consistent, high levels over time in the same cell combined with replication of the VEE-RF RNA for a limited number of multiple cell generations, the VEE-RF RNA approach solves both of the major inefficiency problems associated with attempting to generate iPS cells by daily repeated daily transfections for >14 days of four individual RF mRNAs. Importantly, the VEE-RF RNA is an ectopic hit-and-run approach that does not utilize a DNA intermediate and therefore, there is no opportunity for integrative mutation that can occur with DNA vector-based iPS cell approaches. Moreover, the timing of VEE-RF RNA replicon loss by degradation can be regulated by B18R withdrawal from the media. Using the VEE-RF RNA approach, >100 independent iPS cell clones were generated from both OCT4/KLF4/SOX2/c-MYC and OCT4/KLF4/SOX2/GLIS1 VEE-RF RNA protocols from two independent parental human fibroblast populations. In addition, the VEE-RF RNA approach can be engineered to express alternative RF combinations and/or insertion of additional RF ORFS into the RF-RNA backbone for refining iPS cell generation from specific cell types or for use in driving transdifferentiation. In summary, the VEE-RF RNA replicon approach has broad applicability for the efficient generation of human iPS cells for ultimate use in human stem cell therapies and regenerative medicine.

Accession Numbers.

RNA-Seq data have been submitted and can be accessed by the Gene Expression Omnibus (GEO) accession number GSE38265.

TABLE 3 iPS Cell Generation with VEE-RF RNA Replicon

| RNA Replicon | Cell | Tfx Days | Puromycin selection | AP+ Colonies per starting well |
|---|---|---|---|---|
| OKS-iM | BJ | d 1, | d 2-d 7 | 6 |
| OKS-iM | BJ | d 1, 2 | d 2-d 7 | 32 |
| OKS-iM | BJ | d 1, 2, 3 | d 2-d 7 | 221 |
| OKS-iM | BJ | d 1, 4, 7, 10 | d 2-d 7 | 140 |
| OKS-iM | BJ | d 1 | none | 6 |
| OKS-iM | BJ | d 1, 2 | none | 12 |
| OKS-iM | BJ | d 1, 2, 3 | none | 8 |
| OKS-iM | HFF | d 1, 5, 9 | d 2-d 10 | 179 |
| OKS-iM | HFF | d 1, 4, 7, 10 | d 2-d 4 | 189 |
| OKS-iM | HFF | d 1, 4, 7, 10 | d 2-d 7 | 308 |
| OKS-iM | HFF | d 1, 4, 7, 10 | d 2-d 10 | 338 |
| OKS-iG | BJ | d 1, 4, 7, 10 | d 2-d 7 | 282 |
| OKS-iG | BJ | d 1, 4, 7, 10 | d 2-d 10 | 122 |
| OKS-iG | HFF | d 1, 4, 7, 10 | d 2-d 7 | 267 |
| OKS-iG | HFF | d 1, 4, 7, 10 | d 2-d 10 | 248 |

Although a number of embodiments and features have been described above, it will be understood by those skilled in the art that modifications and variations of the described embodiments and features may be made without departing from the teachings of the disclosure or the scope of the disclosure as defined by the appended claims.

What is claimed is:

1. A RNA replicon comprising:

a plurality of non-structural replicase domains from an alphavirus and at least four heterologous polynucleotide sequences that encode reprogramming factors (RFs) for inducing the generation of pluripotent stem cells when expressed in a somatic cell:

wherein the RNA replicon comprises from 5' to 3': polynucleotide sequences encoding the plurality of non-structural replicase domain sequences obtained from an alphavirus; a promoter; $RF_1$; a coding sequence for a first self-cleaving peptide; $RF_2$; a coding sequence for a second self-cleaving peptide; $RF_3$; an IRES; $RF_4$; an optional IRES or an optional promoter; an optional sequence encoding an optional selectable marker; an alphavirus 3' UTR and polyA tail;

wherein $RF_{1-4}$ are heterologous polynucleotide sequences which encode reprogramming factors that induce de-differentiation of a somatic cell to a pluripotent cell; and wherein $RF_{1-4}$ are polynucleotides encoding RFs selected from the group consisting of Oct-3, Oct-4, Klf, Sox-2, c-Myc, n-Myc, L-Myc, Nanog, and Glis1.

2. The RNA replicon of claim 1, wherein the polynucleotide sequences encoding the plurality of non-structural replicase domain sequences are obtained from an alphavirus selected from the group consisting of Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus and Buggy Creek virus.

3. The RNA replicon of claim 1, wherein the polynucleotide encoding the Klf polypeptide encodes a Klf polypeptide having a sequence selected from:

(a) having at least 95% sequence identity to the sequence of SEQ ID NO:8 and having KLF4 activity; or (b) having the sequence as set forth in SEQ ID NO:8.

4. The RNA replicon of claim 1, wherein the polynucleotide encoding the Klf polypeptide comprises the sequence as set forth in SEQ ID NO:7, wherein the thymidine residues are replaced with uracil resides.

5. The RNA replicon of claim 1, wherein the polynucleotide encoding the Sox-2 polypeptide encodes a Sox-2 polypeptide having a sequence selected from:

(a) having at least 95% sequence identity to the sequence of SEQ ID NO:6 and having Sox-2 activity, or (b) having the sequence as set forth in SEQ ID NO:6.

6. The RNA replicon of claim 1, wherein the polynucleotide encoding the Sox-2 polypeptide comprises the sequence as set forth in SEQ ID NO:5, wherein the thymidine residues are replaced with uracil resides.

7. The RNA replicon of claim 1, wherein the polynucleotide encoding the Oct-4 polypeptide encodes a Oct-4 polypeptide having a sequence selected from:

(a) having at least 95% sequence identity to the sequence of SEQ ID NO:4 and having Oct-4 activity; or (b) having the sequence as set forth in SEQ ID NO:4.

8. The RNA replicon of claim 1, wherein the polynucleotide encoding the Oct-4 polypeptide comprises the sequence as set forth in SEQ ID NO:3, wherein the thymidine residues are replaced with uracil resides.

9. The RNA replicon of claim 1, wherein the polynucleotide encoding the c-Myc polypeptide encodes a c-Myc polypeptide having a sequence selected from:

(a) having at least 95% sequence identity to the sequence of SEQ ID NO:10 and having c-Myc activity; or (b) having the sequence as set forth in SEQ ID NO:10.

10. The RNA replicon of claim 1, wherein the polynucleotide encoding the c-Myc polypeptide comprises the sequence as set forth in SEQ ID NO:9, wherein the thymidine residues are replaced with uracil resides.

11. The RNA replicon of claim 1, wherein the polynucleotide encoding the Glis1 polypeptide encodes a Glis1 polypeptide having a sequence selected from:

(a) having at least 95% sequence identity to the sequence of SEQ ID NO:34 and having Glis1 activity; or (b) having the sequence as set forth in SEQ ID NO:34.

12. The RNA replicon of claim 1, wherein the polynucleotide encoding the Glis1 polypeptide comprises the sequence as set forth in SEQ ID NO:33, wherein the thymidine residues are replaced with uracil resides.

13. The RNA replicon of claim 1, wherein the polynucleotide encoding the Nanog polypeptide encodes a Nanog polypeptide having a sequence selected from:

(a) having at least 95% sequence identity to the sequence of SEQ ID NO:2 and having Nanog activity; or (b) having the sequence as set forth in SEQ ID NO:2.

14. The RNA replicon of claim 1, wherein the polynucleotide encoding the Nanog polypeptide comprises the sequence as set forth in SEQ ID NO:1, wherein the thymidine residues are replaced with uracil resides.

15. The RNA replicon of claim 1, wherein the replicon comprises from 5' to 3':

VEE polynucleotide sequences encoding the plurality of nonstructural replicase domain sequences; a promoter; $RF_1$; a coding sequence for a first self-cleaving peptide; $RF_2$; a coding sequence for a second self-cleaving peptide; $RF_3$; an IRES; $RF_4$; an optional IRES or an optional promoter; an optional sequence encoding an optional selectable marker; a VEE 3' UTR and polyA tail;

wherein $RF_{1-4}$ are selected from the group consisting of Oct-4, Klf4, Sox-2, c-Myc, Nanog, and Glis1.

16. The RNA replicon of claim 1, wherein the replicon comprises a sequence that is 90%, 95%, 98%, 99% or 100% identical to SEQ ID NO:29, 30, 31, or 32 from about position 1 to about position 7561 wherein "T" of the sequence is substituted with "U".

17. The RNA replicon of claim 16, wherein the replicon comprises a sequence that is 100% identical to the sequence of SEQ ID NO:29, 30, 31, or 32, wherein the thymidine residues are replaced with uracil resides.

18. The RNA replicon of claim 1, wherein the promoter located 3' to the polynucleotide sequences encoding the plurality of non-structural replicase domains and 5' to $RF_1$, is a 26S internal promoter.

19. The RNA replicon of claim 1, wherein the coding sequence for the first self-cleaving peptide is a coding sequence for a T2A or E2A self-cleaving peptide.

20. The RNA replicon of claim 1, wherein the coding sequence for the second self-cleaving peptide is a coding sequence for a T2A or E2A self-cleaving peptide.

21. The RNA replicon of claim 15, wherein $RF_1$ is Oct4, $RF_2$ is cMyc, $RF_3$ is Klf4, and $RF_4$ is Sox2.

22. The RNA replicon of claim 15, wherein $RF_1$ is Oct4, $RF_2$ is Klf4, $RF_3$ is Sox2, and $RF_4$ is cMyc.

23. The RNA replicon of claim 15, wherein $RF_1$ is Oct4, $RF_2$ is Klf4, $RF_3$ is Sox2, and $RF_4$ is Glis1.

* * * * *

SEQUENCE LISTING

```
<160> NUMBER OF SEQ ID NOS: 40

<210> SEQ ID NO 1
<211> LENGTH: 918
<212> TYPE: DNA
<213> ORGANISM: Homo sapiens
<220> FEATURE:
<221> NAME/KEY: CDS
<222> LOCATION: (1)..(918)

<400> SEQUENCE: 1

atg agt gtg gat cca gct tgt ccc caa agc ttg cct tgc ttt gaa gca       48
Met Ser Val Asp Pro Ala Cys Pro Gln Ser Leu Pro Cys Phe Glu Ala
1               5                   10                  15

tcc gac tgt aaa gaa tct tca cct atg cct gtg att tgt ggg cct gaa       96
```

```
Ser Asp Cys Lys Glu Ser Ser Pro Met Pro Val Ile Cys Gly Pro Glu
            20                  25                  30

gaa aac tat cca tcc ttg caa atg tct tct gct gag atg cct cac acg      144
Glu Asn Tyr Pro Ser Leu Gln Met Ser Ser Ala Glu Met Pro His Thr
        35                  40                  45

gag act gtc tct cct ctt cct tcc tcc atg gat ctg ctt att cag gac      192
Glu Thr Val Ser Pro Leu Pro Ser Ser Met Asp Leu Leu Ile Gln Asp
    50                  55                  60

agc cct gat tct tcc acc agt ccc aaa ggc aaa caa ccc act tct gca      240
Ser Pro Asp Ser Ser Thr Ser Pro Lys Gly Lys Gln Pro Thr Ser Ala
65                  70                  75                  80

gag aag agt gtc gca aaa aag gaa gac aag gtc ccg gtc aag aaa cag      288
Glu Lys Ser Val Ala Lys Lys Glu Asp Lys Val Pro Val Lys Lys Gln
                85                  90                  95

aag acc aga act gtg ttc tct tcc acc cag ctg tgt gta ctc aat gat      336
Lys Thr Arg Thr Val Phe Ser Ser Thr Gln Leu Cys Val Leu Asn Asp
            100                 105                 110

aga ttt cag aga cag aaa tac ctc agc ctc cag cag atg caa gaa ctc      384
Arg Phe Gln Arg Gln Lys Tyr Leu Ser Leu Gln Gln Met Gln Glu Leu
        115                 120                 125

tcc aac atc ctg aac ctc agc tac aaa cag gtg aag acc tgg ttc cag      432
Ser Asn Ile Leu Asn Leu Ser Tyr Lys Gln Val Lys Thr Trp Phe Gln
    130                 135                 140

aac cag aga atg aaa tct aag agg tgg cag aaa aac aac tgg ccg aag      480
Asn Gln Arg Met Lys Ser Lys Arg Trp Gln Lys Asn Asn Trp Pro Lys
145                 150                 155                 160

aat agc aat ggt gtg acg cag aag gcc tca gca cct acc tac ccc agc      528
Asn Ser Asn Gly Val Thr Gln Lys Ala Ser Ala Pro Thr Tyr Pro Ser
                165                 170                 175

ctt tac tct tcc tac cac cag gga tgc ctg gtg aac ccg act ggg aac      576
Leu Tyr Ser Ser Tyr His Gln Gly Cys Leu Val Asn Pro Thr Gly Asn
            180                 185                 190

ctt cca atg tgg agc aac cag acc tgg aac aat tca acc tgg agc aac      624
Leu Pro Met Trp Ser Asn Gln Thr Trp Asn Asn Ser Thr Trp Ser Asn
        195                 200                 205

cag acc cag aac atc cag tcc tgg agc aac cac tcc tgg aac act cag      672
Gln Thr Gln Asn Ile Gln Ser Trp Ser Asn His Ser Trp Asn Thr Gln
    210                 215                 220

acc tgg tgc acc caa tcc tgg aac aat cag gcc tgg aac agt ccc ttc      720
Thr Trp Cys Thr Gln Ser Trp Asn Asn Gln Ala Trp Asn Ser Pro Phe
225                 230                 235                 240

tat aac tgt gga gag gaa tct ctg cag tcc tgc atg cag ttc cag cca      768
Tyr Asn Cys Gly Glu Glu Ser Leu Gln Ser Cys Met Gln Phe Gln Pro
                245                 250                 255

aat tct cct gcc agt gac ttg gag gct gcc ttg gaa gct gct ggg gaa      816
Asn Ser Pro Ala Ser Asp Leu Glu Ala Ala Leu Glu Ala Ala Gly Glu
            260                 265                 270

ggc ctt aat gta ata cag cag acc act agg tat ttt agt act cca caa      864
Gly Leu Asn Val Ile Gln Gln Thr Thr Arg Tyr Phe Ser Thr Pro Gln
        275                 280                 285

acc atg gat tta ttc cta aac tac tcc atg aac atg caa cct gaa gac      912
Thr Met Asp Leu Phe Leu Asn Tyr Ser Met Asn Met Gln Pro Glu Asp
    290                 295                 300

gtg tga                                                              918
Val
305

<210> SEQ ID NO 2
<211> LENGTH: 305
<212> TYPE: PRT
```

```
<213> ORGANISM: Homo sapiens

<400> SEQUENCE: 2

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305


<210> SEQ ID NO 3
<211> LENGTH: 1083
<212> TYPE: DNA
<213> ORGANISM: Homo sapiens
<220> FEATURE:
<221> NAME/KEY: CDS
<222> LOCATION: (1)..(1083)

<400> SEQUENCE: 3

atg gcg gga cac ctg gct tcg gat ttc gcc ttc tcg ccc cct cca ggt       48
Met Ala Gly His Leu Ala Ser Asp Phe Ala Phe Ser Pro Pro Pro Gly
1               5                   10                  15
```

```
ggt gga ggt gat ggg cca ggg ggg ccg gag ccg ggc tgg gtt gat cct        96
Gly Gly Gly Asp Gly Pro Gly Gly Pro Glu Pro Gly Trp Val Asp Pro
            20                  25                  30

cgg acc tgg cta agc ttc caa ggc cct cct gga ggg cca gga atc ggg       144
Arg Thr Trp Leu Ser Phe Gln Gly Pro Pro Gly Gly Pro Gly Ile Gly
        35                  40                  45

ccg ggg gtt ggg cca ggc tct gag gtg tgg ggg att ccc cca tgc ccc       192
Pro Gly Val Gly Pro Gly Ser Glu Val Trp Gly Ile Pro Pro Cys Pro
    50                  55                  60

ccg ccg tat gag ttc tgt ggg ggg atg gcg tac tgt ggg ccc cag gtt       240
Pro Pro Tyr Glu Phe Cys Gly Gly Met Ala Tyr Cys Gly Pro Gln Val
65                  70                  75                  80

gga gtg ggg cta gtg ccc caa ggc ggc ttg gag acc tct cag cct gag       288
Gly Val Gly Leu Val Pro Gln Gly Gly Leu Glu Thr Ser Gln Pro Glu
                85                  90                  95

ggc gaa gca gga gtc ggg gtg gag agc aac tcc gat ggg gcc tcc ccg       336
Gly Glu Ala Gly Val Gly Val Glu Ser Asn Ser Asp Gly Ala Ser Pro
            100                 105                 110

gag ccc tgc acc gtc acc cct ggt gcc gtg aag ctg gag aag gag aag       384
Glu Pro Cys Thr Val Thr Pro Gly Ala Val Lys Leu Glu Lys Glu Lys
        115                 120                 125

ctg gag caa aac ccg gag gag tcc cag gac atc aaa gct ctg cag aaa       432
Leu Glu Gln Asn Pro Glu Glu Ser Gln Asp Ile Lys Ala Leu Gln Lys
    130                 135                 140

gaa ctc gag caa ttt gcc aag ctc ctg aag cag aag agg atc acc ctg       480
Glu Leu Glu Gln Phe Ala Lys Leu Leu Lys Gln Lys Arg Ile Thr Leu
145                 150                 155                 160

gga tat aca cag gcc gat gtg ggg ctc acc ctg ggg gtt cta ttt ggg       528
Gly Tyr Thr Gln Ala Asp Val Gly Leu Thr Leu Gly Val Leu Phe Gly
                165                 170                 175

aag gta ttc agc caa acg acc atc tgc cgc ttt gag gct ctg cag ctt       576
Lys Val Phe Ser Gln Thr Thr Ile Cys Arg Phe Glu Ala Leu Gln Leu
            180                 185                 190

agc ttc aag aac atg tgt aag ctg cgg ccc ttg ctg cag aag tgg gtg       624
Ser Phe Lys Asn Met Cys Lys Leu Arg Pro Leu Leu Gln Lys Trp Val
        195                 200                 205

gag gaa gct gac aac aat gaa aat ctt cag gag ata tgc aaa gca gaa       672
Glu Glu Ala Asp Asn Asn Glu Asn Leu Gln Glu Ile Cys Lys Ala Glu
    210                 215                 220

acc ctc gtg cag gcc cga aag aga aag cga acc agt atc gag aac cga       720
Thr Leu Val Gln Ala Arg Lys Arg Lys Arg Thr Ser Ile Glu Asn Arg
225                 230                 235                 240

gtg aga ggc aac ctg gag aat ttg ttc ctg cag tgc ccg aaa ccc aca       768
Val Arg Gly Asn Leu Glu Asn Leu Phe Leu Gln Cys Pro Lys Pro Thr
                245                 250                 255

ctg cag cag atc agc cac atc gcc cag cag ctt ggg ctc gag aag gat       816
Leu Gln Gln Ile Ser His Ile Ala Gln Gln Leu Gly Leu Glu Lys Asp
            260                 265                 270

gtg gtc cga gtg tgg ttc tgt aac cgg cgc cag aag ggc aag cga tca       864
Val Val Arg Val Trp Phe Cys Asn Arg Arg Gln Lys Gly Lys Arg Ser
        275                 280                 285

agc agc gac tat gca caa cga gag gat ttt gag gct gct ggg tct cct       912
Ser Ser Asp Tyr Ala Gln Arg Glu Asp Phe Glu Ala Ala Gly Ser Pro
    290                 295                 300

ttc tca ggg gga cca gtg tcc ttt cct ctg gcc cca ggg ccc cat ttt       960
Phe Ser Gly Gly Pro Val Ser Phe Pro Leu Ala Pro Gly Pro His Phe
305                 310                 315                 320

ggt acc cca ggc tat ggg agc cct cac ttc act gca ctg tac tcc tcg      1008
Gly Thr Pro Gly Tyr Gly Ser Pro His Phe Thr Ala Leu Tyr Ser Ser
                325                 330                 335
```

```
gtc cct ttc cct gag ggg gaa gcc ttt ccc cct gtc tcc gtc acc act      1056
Val Pro Phe Pro Glu Gly Glu Ala Phe Pro Pro Val Ser Val Thr Thr
            340                 345                 350

ctg ggc tct ccc atg cat tca aac tga                                  1083
Leu Gly Ser Pro Met His Ser Asn
        355                 360


<210> SEQ ID NO 4
<211> LENGTH: 360
<212> TYPE: PRT
<213> ORGANISM: Homo sapiens

<400> SEQUENCE: 4

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335
```

```
Val Pro Phe Pro Glu Gly Glu Ala Phe Pro Pro Val Ser Val Thr Thr
            340                 345                 350

Leu Gly Ser Pro Met His Ser Asn
        355                 360


<210> SEQ ID NO 5
<211> LENGTH: 954
<212> TYPE: DNA
<213> ORGANISM: Homo sapiens
<220> FEATURE:
<221> NAME/KEY: CDS
<222> LOCATION: (1)..(954)

<400> SEQUENCE: 5

atg tac aac atg atg gag acg gag ctg aag ccg ccg ggc ccg cag caa       48
Met Tyr Asn Met Met Glu Thr Glu Leu Lys Pro Pro Gly Pro Gln Gln
1               5                   10                  15

act tcg ggg ggc ggc ggc ggc aac tcc acc gcg gcg gcg gcc ggc ggc       96
Thr Ser Gly Gly Gly Gly Gly Asn Ser Thr Ala Ala Ala Ala Gly Gly
            20                  25                  30

aac cag aaa aac agc ccg gac cgc gtc aag cgg ccc atg aat gcc ttc      144
Asn Gln Lys Asn Ser Pro Asp Arg Val Lys Arg Pro Met Asn Ala Phe
        35                  40                  45

atg gtg tgg tcc cgc ggg cag cgg cgc aag atg gcc cag gag aac ccc      192
Met Val Trp Ser Arg Gly Gln Arg Arg Lys Met Ala Gln Glu Asn Pro
    50                  55                  60

aag atg cac aac tcg gag atc agc aag cgc ctg ggc gcc gag tgg aaa      240
Lys Met His Asn Ser Glu Ile Ser Lys Arg Leu Gly Ala Glu Trp Lys
65                  70                  75                  80

ctt ttg tcg gag acg gag aag cgg ccg ttc atc gac gag gct aag cgg      288
Leu Leu Ser Glu Thr Glu Lys Arg Pro Phe Ile Asp Glu Ala Lys Arg
                85                  90                  95

ctg cga gcg ctg cac atg aag gag cac ccg gat tat aaa tac cgg ccc      336
Leu Arg Ala Leu His Met Lys Glu His Pro Asp Tyr Lys Tyr Arg Pro
            100                 105                 110

cgg cgg aaa acc aag acg ctc atg aag aag gat aag tac acg ctg ccc      384
Arg Arg Lys Thr Lys Thr Leu Met Lys Lys Asp Lys Tyr Thr Leu Pro
        115                 120                 125

ggc ggg ctg ctg gcc ccc ggc ggc aat agc atg gcg agc ggg gtc ggg      432
Gly Gly Leu Leu Ala Pro Gly Gly Asn Ser Met Ala Ser Gly Val Gly
    130                 135                 140

gtg ggc gcc ggc ctg ggc gcg ggc gtg aac cag cgc atg gac agt tac      480
Val Gly Ala Gly Leu Gly Ala Gly Val Asn Gln Arg Met Asp Ser Tyr
145                 150                 155                 160

gcg cac atg aac ggc tgg agc aac ggc agc tac agc atg atg cag gac      528
Ala His Met Asn Gly Trp Ser Asn Gly Ser Tyr Ser Met Met Gln Asp
                165                 170                 175

cag ctg ggc tac ccg cag cac ccg ggc ctc aat gcg cac ggc gca gcg      576
Gln Leu Gly Tyr Pro Gln His Pro Gly Leu Asn Ala His Gly Ala Ala
            180                 185                 190

cag atg cag ccc atg cac cgc tac gac gtg agc gcc ctg cag tac aac      624
Gln Met Gln Pro Met His Arg Tyr Asp Val Ser Ala Leu Gln Tyr Asn
        195                 200                 205

tcc atg acc agc tcg cag acc tac atg aac ggc tcg ccc acc tac agc      672
Ser Met Thr Ser Ser Gln Thr Tyr Met Asn Gly Ser Pro Thr Tyr Ser
    210                 215                 220

atg tcc tac tcg cag cag ggc acc cct ggc atg gct ctt ggc tcc atg      720
Met Ser Tyr Ser Gln Gln Gly Thr Pro Gly Met Ala Leu Gly Ser Met
225                 230                 235                 240

ggt tcg gtg gtc aag tcc gag gcc agc tcc agc ccc cct gtg gtt acc      768
```

```
Gly Ser Val Val Lys Ser Glu Ala Ser Ser Ser Pro Pro Val Val Thr
                245                 250                 255

tct tcc tcc cac tcc agg gcg ccc tgc cag gcc ggg gac ctc cgg gac      816
Ser Ser Ser His Ser Arg Ala Pro Cys Gln Ala Gly Asp Leu Arg Asp
            260                 265                 270

atg atc agc atg tat ctc ccc ggc gcc gag gtg ccg gaa ccc gcc gcc      864
Met Ile Ser Met Tyr Leu Pro Gly Ala Glu Val Pro Glu Pro Ala Ala
        275                 280                 285

ccc agc aga ctt cac atg tcc cag cac tac cag agc ggc ccg gtg ccc      912
Pro Ser Arg Leu His Met Ser Gln His Tyr Gln Ser Gly Pro Val Pro
    290                 295                 300

ggc acg gcc att aac ggc aca ctg ccc ctc tca cac atg tga              954
Gly Thr Ala Ile Asn Gly Thr Leu Pro Leu Ser His Met
305                 310                 315


<210> SEQ ID NO 6
<211> LENGTH: 317
<212> TYPE: PRT
<213> ORGANISM: Homo sapiens

<400> SEQUENCE: 6

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
```

```
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315


<210> SEQ ID NO 7
<211> LENGTH: 1440
<212> TYPE: DNA
<213> ORGANISM: Homo sapiens
<220> FEATURE:
<221> NAME/KEY: CDS
<222> LOCATION: (1)..(1440)

<400> SEQUENCE: 7

atg agg cag cca cct ggc gag tct gac atg gct gtc agc gac gcg ctg       48
Met Arg Gln Pro Pro Gly Glu Ser Asp Met Ala Val Ser Asp Ala Leu
1               5                   10                  15

ctc cca tct ttc tcc acg ttc gcg tct ggc ccg gcg gga agg gag aag       96
Leu Pro Ser Phe Ser Thr Phe Ala Ser Gly Pro Ala Gly Arg Glu Lys
            20                  25                  30

aca ctg cgt caa gca ggt gcc ccg aat aac cgc tgg cgg gag gag ctc      144
Thr Leu Arg Gln Ala Gly Ala Pro Asn Asn Arg Trp Arg Glu Glu Leu
        35                  40                  45

tcc cac atg aag cga ctt ccc cca gtg ctt ccc ggc cgc ccc tat gac      192
Ser His Met Lys Arg Leu Pro Pro Val Leu Pro Gly Arg Pro Tyr Asp
    50                  55                  60

ctg gcg gcg gcg acc gtg gcc aca gac ctg gag agc ggc gga gcc ggt      240
Leu Ala Ala Ala Thr Val Ala Thr Asp Leu Glu Ser Gly Gly Ala Gly
65                  70                  75                  80

gcg gct tgc ggc ggt agc aac ctg gcg ccc cta cct cgg aga gag acc      288
Ala Ala Cys Gly Gly Ser Asn Leu Ala Pro Leu Pro Arg Arg Glu Thr
                85                  90                  95

gag gag ttc aac gat ctc ctg gac ctg gac ttt att ctc tcc aat tcg      336
Glu Glu Phe Asn Asp Leu Leu Asp Leu Asp Phe Ile Leu Ser Asn Ser
            100                 105                 110

ctg acc cat cct ccg gag tca gtg gcc gcc acc gtg tcc tcg tca gcg      384
Leu Thr His Pro Pro Glu Ser Val Ala Ala Thr Val Ser Ser Ser Ala
        115                 120                 125

tca gcc tcc tct tcg tcg tcg ccg tcg agc agc ggc cct gcc agc gcg      432
Ser Ala Ser Ser Ser Ser Ser Pro Ser Ser Ser Gly Pro Ala Ser Ala
    130                 135                 140

ccc tcc acc tgc agc ttc acc tat ccg atc cgg gcc ggg aac gac ccg      480
Pro Ser Thr Cys Ser Phe Thr Tyr Pro Ile Arg Ala Gly Asn Asp Pro
145                 150                 155                 160

ggc gtg gcg ccg ggc ggc acg ggc gga ggc ctc ctc tat ggc agg gag      528
Gly Val Ala Pro Gly Gly Thr Gly Gly Gly Leu Leu Tyr Gly Arg Glu
                165                 170                 175

tcc gct ccc cct ccg acg gct ccc ttc aac ctg gcg gac atc aac gac      576
Ser Ala Pro Pro Pro Thr Ala Pro Phe Asn Leu Ala Asp Ile Asn Asp
            180                 185                 190

gtg agc ccc tcg ggc ggc ttc gtg gcc gag ctc ctg cgg cca gaa ttg      624
Val Ser Pro Ser Gly Gly Phe Val Ala Glu Leu Leu Arg Pro Glu Leu
        195                 200                 205

gac ccg gtg tac att ccg ccg cag cag ccg cag ccg cca ggt ggc ggg      672
Asp Pro Val Tyr Ile Pro Pro Gln Gln Pro Gln Pro Pro Gly Gly Gly
    210                 215                 220

ctg atg ggc aag ttc gtg ctg aag gcg tcg ctg agc gcc cct ggc agc      720
Leu Met Gly Lys Phe Val Leu Lys Ala Ser Leu Ser Ala Pro Gly Ser
225                 230                 235                 240
```

```
gag tac ggc agc ccg tcg gtc atc agc gtc agc aaa ggc agc cct gac      768
Glu Tyr Gly Ser Pro Ser Val Ile Ser Val Ser Lys Gly Ser Pro Asp
                245                 250                 255

ggc agc cac ccg gtg gtg gtg gcg ccc tac aac ggc ggg ccg ccg cgc      816
Gly Ser His Pro Val Val Val Ala Pro Tyr Asn Gly Gly Pro Pro Arg
            260                 265                 270

acg tgc ccc aag atc aag cag gag gcg gtc tct tcg tgc acc cac ttg      864
Thr Cys Pro Lys Ile Lys Gln Glu Ala Val Ser Ser Cys Thr His Leu
        275                 280                 285

ggc gct gga ccc cct ctc agc aat ggc cac cgg ccg gct gca cac gac      912
Gly Ala Gly Pro Pro Leu Ser Asn Gly His Arg Pro Ala Ala His Asp
    290                 295                 300

ttc ccc ctg ggg cgg cag ctc ccc agc agg act acc ccg acc ctg ggt      960
Phe Pro Leu Gly Arg Gln Leu Pro Ser Arg Thr Thr Pro Thr Leu Gly
305                 310                 315                 320

ctt gag gaa gtg ctg agc agc agg gac tgt cac cct gcc ctg ccg ctt     1008
Leu Glu Glu Val Leu Ser Ser Arg Asp Cys His Pro Ala Leu Pro Leu
                325                 330                 335

cct ccc ggc ttc cat ccc cac ccg ggg ccc aat tac cca tcc ttc ctg     1056
Pro Pro Gly Phe His Pro His Pro Gly Pro Asn Tyr Pro Ser Phe Leu
            340                 345                 350

ccc gat cag atg cag ccg caa gtc ccg ccg ctc cat tac caa gag ctc     1104
Pro Asp Gln Met Gln Pro Gln Val Pro Pro Leu His Tyr Gln Glu Leu
        355                 360                 365

atg cca ccc ggt tcc tgc atg cca gag gag ccc aag cca aag agg gga     1152
Met Pro Pro Gly Ser Cys Met Pro Glu Glu Pro Lys Pro Lys Arg Gly
    370                 375                 380

aga cga tcg tgg ccc cgg aaa agg acc gcc acc cac act tgt gat tac     1200
Arg Arg Ser Trp Pro Arg Lys Arg Thr Ala Thr His Thr Cys Asp Tyr
385                 390                 395                 400

gcg ggc tgc ggc aaa acc tac aca aag agt tcc cat ctc aag gca cac     1248
Ala Gly Cys Gly Lys Thr Tyr Thr Lys Ser Ser His Leu Lys Ala His
                405                 410                 415

ctg cga acc cac aca ggt gag aaa cct tac cac tgt gac tgg gac ggc     1296
Leu Arg Thr His Thr Gly Glu Lys Pro Tyr His Cys Asp Trp Asp Gly
            420                 425                 430

tgt gga tgg aaa ttc gcc cgc tca gat gaa ctg acc agg cac tac cgt     1344
Cys Gly Trp Lys Phe Ala Arg Ser Asp Glu Leu Thr Arg His Tyr Arg
        435                 440                 445

aaa cac acg ggg cac cgc ccg ttc cag tgc caa aaa tgc gac cga gca     1392
Lys His Thr Gly His Arg Pro Phe Gln Cys Gln Lys Cys Asp Arg Ala
    450                 455                 460

ttt tcc agg tcg gac cac ctc gcc tta cac atg aag agg cat ttt taa     1440
Phe Ser Arg Ser Asp His Leu Ala Leu His Met Lys Arg His Phe
465                 470                 475
```

<210> SEQ ID NO 8
<211> LENGTH: 479
<212> TYPE: PRT
<213> ORGANISM: Homo sapiens

<400> SEQUENCE: 8

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60
```

```
Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475
```

<210> SEQ ID NO 9
<211> LENGTH: 1323
<212> TYPE: DNA
<213> ORGANISM: Homo sapiens
<220> FEATURE:
<221> NAME/KEY: CDS
<222> LOCATION: (1)..(1323)

<400> SEQUENCE: 9

```
atg ggc ccc ctc aac gtt agc ttc acc aac agg aac tat gac ctc gac       48
Met Gly Pro Leu Asn Val Ser Phe Thr Asn Arg Asn Tyr Asp Leu Asp
1               5                   10                  15

tac gac tcg gtg cag ccg tat ttc tac tgc gac gag gag gag aac ttc       96
Tyr Asp Ser Val Gln Pro Tyr Phe Tyr Cys Asp Glu Glu Glu Asn Phe
            20                  25                  30

tac cag cag cag cag cag agc gag ctg cag ccc ccg gcg ccc agc gag      144
Tyr Gln Gln Gln Gln Gln Ser Glu Leu Gln Pro Pro Ala Pro Ser Glu
        35                  40                  45

gat atc tgg aag aaa ttc gag ctg ctg ccc acc ccg ccc ctg tcc cct      192
Asp Ile Trp Lys Lys Phe Glu Leu Leu Pro Thr Pro Pro Leu Ser Pro
    50                  55                  60

agc cgc cgc tcc ggg ctc tgc tcg ccc tcc tac gtt gcg gtc aca ccc      240
Ser Arg Arg Ser Gly Leu Cys Ser Pro Ser Tyr Val Ala Val Thr Pro
65                  70                  75                  80

ttc tcc ctt cgg gga gac aac gac ggc ggt ggc ggg agc ttc tcc acg      288
Phe Ser Leu Arg Gly Asp Asn Asp Gly Gly Gly Gly Ser Phe Ser Thr
                85                  90                  95

gcc gac cag ctg gag atg gtg acc gag ctg ctg gga gga gac atg gtg      336
Ala Asp Gln Leu Glu Met Val Thr Glu Leu Leu Gly Gly Asp Met Val
            100                 105                 110

aac cag agt ttc atc tgc gac ccg gac gac gag acc ttc atc aaa aac      384
Asn Gln Ser Phe Ile Cys Asp Pro Asp Asp Glu Thr Phe Ile Lys Asn
        115                 120                 125

atc atc atc cag gac tgt atg tgg agc ggc ttc tcg gcc gcc gcc aag      432
Ile Ile Ile Gln Asp Cys Met Trp Ser Gly Phe Ser Ala Ala Ala Lys
    130                 135                 140

ctc gtc tca gag aag ctg gcc tcc tac cag gct gcg cgc aaa gac agc      480
Leu Val Ser Glu Lys Leu Ala Ser Tyr Gln Ala Ala Arg Lys Asp Ser
145                 150                 155                 160

ggc agc ccg aac ccc gcc cgc ggc cac agc gtc tgc tcc acc tcc agc      528
Gly Ser Pro Asn Pro Ala Arg Gly His Ser Val Cys Ser Thr Ser Ser
                165                 170                 175

ttg tac ctg cag gat ctg agc gcc gcc gcc tca gag tgc atc gac ccc      576
Leu Tyr Leu Gln Asp Leu Ser Ala Ala Ala Ser Glu Cys Ile Asp Pro
            180                 185                 190

tcg gtg gtc ttc ccc tac cct ctc aac gac agc agc tcg ccc aag tcc      624
Ser Val Val Phe Pro Tyr Pro Leu Asn Asp Ser Ser Ser Pro Lys Ser
        195                 200                 205

tgc gcc tcg caa gac tcc agc gcc ttc tct ccg tcc tcg gat tct ctg      672
Cys Ala Ser Gln Asp Ser Ser Ala Phe Ser Pro Ser Ser Asp Ser Leu
    210                 215                 220

ctc tcc tcg acg gag tcc tcc ccg cag ggc agc ccc gag ccc ctg gtg      720
Leu Ser Ser Thr Glu Ser Ser Pro Gln Gly Ser Pro Glu Pro Leu Val
225                 230                 235                 240

ctc cat gag gag aca ccg ccc acc acc agc agc gac tct gag gag gaa      768
Leu His Glu Glu Thr Pro Pro Thr Thr Ser Ser Asp Ser Glu Glu Glu
                245                 250                 255

caa gaa gat gag gaa gaa atc gat gtt gtt tct gtg gaa aag agg cag      816
Gln Glu Asp Glu Glu Glu Ile Asp Val Val Ser Val Glu Lys Arg Gln
            260                 265                 270
```

```
gct cct ggc aaa agg tca gag tct gga tca cct tct gct gga ggc cac      864
Ala Pro Gly Lys Arg Ser Glu Ser Gly Ser Pro Ser Ala Gly Gly His
        275                 280                 285

agc aaa cct cct cac agc cca ctg gtc ctc aag agg tgc cac gtc tcc      912
Ser Lys Pro Pro His Ser Pro Leu Val Leu Lys Arg Cys His Val Ser
    290                 295                 300

aca cat cag cac aac tac gca gcg cct ccc tcc act cgg aag gac tat      960
Thr His Gln His Asn Tyr Ala Ala Pro Pro Ser Thr Arg Lys Asp Tyr
305                 310                 315                 320

cct gct gcc aag agg gtc aag ttg gac agt gtc aga gtc ctg aga cag     1008
Pro Ala Ala Lys Arg Val Lys Leu Asp Ser Val Arg Val Leu Arg Gln
                325                 330                 335

atc agc aac aac cga aaa tgc acc agc ccc agg tcc tcg gac acc gag     1056
Ile Ser Asn Asn Arg Lys Cys Thr Ser Pro Arg Ser Ser Asp Thr Glu
            340                 345                 350

gag aat gtc aag agg cga aca cac aac gtc ttg gag cgc cag agg agg     1104
Glu Asn Val Lys Arg Arg Thr His Asn Val Leu Glu Arg Gln Arg Arg
        355                 360                 365

aac gag cta aaa cgg agc ttt ttt gcc ctg cgt gac cag atc ccg gag     1152
Asn Glu Leu Lys Arg Ser Phe Phe Ala Leu Arg Asp Gln Ile Pro Glu
    370                 375                 380

ttg gaa aac aat gaa aag gcc ccc aag gta gtt atc ctt aaa aaa gcc     1200
Leu Glu Asn Asn Glu Lys Ala Pro Lys Val Val Ile Leu Lys Lys Ala
385                 390                 395                 400

aca gca tac atc ctg tcc gtc caa gca gag gag caa aag ctc att tct     1248
Thr Ala Tyr Ile Leu Ser Val Gln Ala Glu Glu Gln Lys Leu Ile Ser
                405                 410                 415

gaa gag gac ttg ttg cgg aaa cga cga gaa cag ttg aaa cac aaa ctt     1296
Glu Glu Asp Leu Leu Arg Lys Arg Arg Glu Gln Leu Lys His Lys Leu
            420                 425                 430

gaa cag cta cgg aac tct tgt gcg taa                                 1323
Glu Gln Leu Arg Asn Ser Cys Ala
        435                 440


<210> SEQ ID NO 10
<211> LENGTH: 440
<212> TYPE: PRT
<213> ORGANISM: Homo sapiens

<400> SEQUENCE: 10

Met Gly Pro Leu Asn Val Ser Phe Thr Asn Arg Asn Tyr Asp Leu Asp
1               5                   10                  15

Tyr Asp Ser Val Gln Pro Tyr Phe Tyr Cys Asp Glu Glu Glu Asn Phe
            20                  25                  30

Tyr Gln Gln Gln Gln Ser Glu Leu Gln Pro Pro Ala Pro Ser Glu
        35                  40                  45

Asp Ile Trp Lys Lys Phe Glu Leu Leu Pro Thr Pro Pro Leu Ser Pro
    50                  55                  60

Ser Arg Arg Ser Gly Leu Cys Ser Pro Ser Tyr Val Ala Val Thr Pro
65                  70                  75                  80

Phe Ser Leu Arg Gly Asp Asn Asp Gly Gly Gly Gly Ser Phe Ser Thr
                85                  90                  95

Ala Asp Gln Leu Glu Met Val Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
    130                 135                 140
```

```
Leu Val Ser Glu Lys Leu Ala Ser Tyr Gln Ala Ala Arg Lys Asp Ser
145                 150                 155                 160

Gly Ser Pro Asn Pro Ala Arg Gly His Ser Val Cys Ser Thr Ser Ser
                165                 170                 175

Leu Tyr Leu Gln Asp Leu Ser Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Ala Ser Gln Asp Ser Ser Ala Phe Ser Pro Ser Ser Asp Ser Leu
    210                 215                 220

Leu Ser Ser Thr Glu Ser Ser Pro Gln Gly Ser Pro Glu Pro Leu Val
225                 230                 235                 240

Leu His Glu Glu Thr Pro Pro Thr Thr Ser Ser Asp Ser Glu Glu Glu
                245                 250                 255

Gln Glu Asp Glu Glu Glu Ile Asp Val Val Ser Val Glu Lys Arg Gln
            260                 265                 270

Ala Pro Gly Lys Arg Ser Glu Ser Gly Ser Pro Ser Ala Gly Gly His
        275                 280                 285

Ser Lys Pro Pro His Ser Pro Leu Val Leu Lys Arg Cys His Val Ser
    290                 295                 300

Thr His Gln His Asn Tyr Ala Ala Pro Pro Ser Thr Arg Lys Asp Tyr
305                 310                 315                 320

Pro Ala Ala Lys Arg Val Lys Leu Asp Ser Val Arg Val Leu Arg Gln
                325                 330                 335

Ile Ser Asn Asn Arg Lys Cys Thr Ser Pro Arg Ser Ser Asp Thr Glu
            340                 345                 350

Glu Asn Val Lys Arg Arg Thr His Asn Val Leu Glu Arg Gln Arg Arg
        355                 360                 365

Asn Glu Leu Lys Arg Ser Phe Phe Ala Leu Arg Asp Gln Ile Pro Glu
    370                 375                 380

Leu Glu Asn Asn Glu Lys Ala Pro Lys Val Val Ile Leu Lys Lys Ala
385                 390                 395                 400

Thr Ala Tyr Ile Leu Ser Val Gln Ala Glu Glu Gln Lys Leu Ile Ser
                405                 410                 415

Glu Glu Asp Leu Leu Arg Lys Arg Arg Glu Gln Leu Lys His Lys Leu
            420                 425                 430

Glu Gln Leu Arg Asn Ser Cys Ala
        435                 440


<210> SEQ ID NO 11
<211> LENGTH: 84
<212> TYPE: DNA
<213> ORGANISM: Artificial Sequence
<220> FEATURE:
<223> OTHER INFORMATION: Oligonucleotide primer - Forward F2A

<400> SEQUENCE: 11

aattcaccgg tgtgaaacag actttgaatt ttgaccttct caagttggcg ggagacgtgg     60

agtccaaccc agggcccaga tcta                                            84


<210> SEQ ID NO 12
<211> LENGTH: 84
<212> TYPE: DNA
<213> ORGANISM: Artificial Sequence
<220> FEATURE:
<223> OTHER INFORMATION: Oligonucleotide primer - Reverse F2A
```

<400> SEQUENCE: 12
ctagtagatc tgggccctgg gttggactcc acgtctcccg ccaacttgag aaggtcaaaa 60
ttcaaagtct gtttcacacc ggtg 84

<210> SEQ ID NO 13
<211> LENGTH: 66
<212> TYPE: DNA
<213> ORGANISM: Artificial Sequence
<220> FEATURE:
<223> OTHER INFORMATION: Oligonucleotide Primer - Forward T2A

<400> SEQUENCE: 13
ctagtgaggg cagaggaagt ctgctaacat gcggtgacgt cgaggagaat cctggcccac 60
aattgt 66

<210> SEQ ID NO 14
<211> LENGTH: 66
<212> TYPE: DNA
<213> ORGANISM: Artificial Sequence
<220> FEATURE:
<223> OTHER INFORMATION: Oligonucleotide primer - Reverse T2A

<400> SEQUENCE: 14
ctagacaatt gtgggccagg attctcctcg acgtcaccgc atgttagcag acttcctctg 60
ccctca 66

<210> SEQ ID NO 15
<211> LENGTH: 76
<212> TYPE: DNA
<213> ORGANISM: Artificial Sequence
<220> FEATURE:
<223> OTHER INFORMATION: Oligonucleotide Primer - Forward E2A

<400> SEQUENCE: 15
ctagacaatg tactaactac gctttgttga aactcgctgg cgatgttgaa agtaaccccg 60
gtcctggcgc gcccgc 76

<210> SEQ ID NO 16
<211> LENGTH: 76
<212> TYPE: DNA
<213> ORGANISM: Artificial Sequence
<220> FEATURE:
<223> OTHER INFORMATION: Oligonucleotide primer - Reverse E2A

<400> SEQUENCE: 16
ggccgcgggc gcgccaggac cggggttact ttcaacatcg ccagcgagtt tcaacaaagc 60
gtagttagta cattgt 76

<210> SEQ ID NO 17
<211> LENGTH: 52
<212> TYPE: DNA
<213> ORGANISM: Artificial Sequence
<220> FEATURE:
<223> OTHER INFORMATION: Oligonucleotide primer - Forward VEE-MCS

<400> SEQUENCE: 17
ctagcatatg ggcgcgccct cagcatcgat ggccggcctc tagagcggcc gc 52

<210> SEQ ID NO 18
<211> LENGTH: 52
<212> TYPE: DNA
<213> ORGANISM: Artificial Sequence
<220> FEATURE:
<223> OTHER INFORMATION: Oligonucleotide primer - Reverse VEE-MCS

<400> SEQUENCE: 18
ggccgcggcc gctctagagg ccggccatcg atgctgaggg cgcgcccata tg 52

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer - Forward nsP2a

<400> SEQUENCE: 19
caggacgatc tcattctcac 20

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide primer - Reverse nsP2a

<400> SEQUENCE: 20
gcttgccact cctctatcgt g 21

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer - Forward nsP4a

<400> SEQUENCE: 21
ccacaatacg atcggcagtg 20

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide primer - Reverse nsP4a

<400> SEQUENCE: 22
atgtcctgca acatattcaa a 21

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer - Forward Oct4RTa

<400> SEQUENCE: 23
cggcgccaga agggcaagcg 20

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer - Klf4RTb

<400> SEQUENCE: 24
cacctgcttg acgcagtgtc 20

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide primer - Bis-Oct-10F

<400> SEQUENCE: 25
ggagtagaag gattgttttg gttta 25

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide primer - Bis-Oct-9R

<400> SEQUENCE: 26
aaaccttaaa aacttaacca aatcc 25

<210> SEQ ID NO 27
<211> LENGTH: 26
<212> TYPE: DNA
<213> ORGANISM: Artificial Sequence
<220> FEATURE:
<223> OTHER INFORMATION: Oligonucleotide primer - Bis-Nanog-4F

<400> SEQUENCE: 27
agagtagttg ggattataga tattta 26

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide primer - Bis-Nanog-3R

<400> SEQUENCE: 28
aacaacaaaa cctaaaaaca aacc 24

<210> SEQ ID NO 29
<211> LENGTH: 16337
<212> TYPE: DNA
<213> ORGANISM: Artificial Sequence
<220> FEATURE:
<223> OTHER INFORMATION: VEE-Oct-Klf-Sox-cMyc

<400> SEQUENCE: 29
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660

```
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
```

```
cagagcatga tgccatcatg aggcacatct tggagagacc ggaccctacc gacgtcttcc   3060

agaataaggc aaacgtgtgt tgggccaagg ctttagtgcc ggtgctgaag accgctggca   3120

tagacatgac cactgaacaa tggaacactg tggattattt tgaaacggac aaagctcact   3180

cagcagagat agtattgaac caactatgcg tgaggttctt tggactcgat ctggactccg   3240

gtctattttc tgcacccact gttccgttat ccattaggaa taatcactgg gataactccc   3300

cgtcgcctaa catgtacggg ctgaataaag aagtggtccg tcagctctct cgcaggtacc   3360

cacaactgcc tcgggcagtt gccactggaa gagtctatga catgaacact ggtacactgc   3420

gcaattatga tccgcgcata aacctagtac ctgtaaacag aagactgcct catgctttag   3480

tcctccacca taatgaacac ccacagagtg acttttcttc attcgtcagc aaattgaagg   3540

gcagaactgt cctggtggtc ggggaaaagt tgtccgtccc aggcaaaatg gttgactggt   3600

tgtcagaccg gcctgaggct accttcagag ctcggctgga tttaggcatc ccaggtgatg   3660

tgcccaaata tgacataata tttgttaatg tgaggacccc atataaatac catcactatc   3720

agcagtgtga agaccatgcc attaagctta gcatgttgac caagaaagct tgtctgcatc   3780

tgaatcccgg cggaacctgt gtcagcatag gttatggtta cgctgacagg gccagcgaaa   3840

gcatcattgg tgctatagcg cggcagttca agttttcccg ggtatgcaaa ccgaaatcct   3900

cacttgaaga gacggaagtt ctgtttgtat tcattgggta cgatcgcaag gcccgtacgc   3960

acaattctta caagctttca tcaaccttga ccaacattta tacaggttcc agactccacg   4020

aagccggatg tgcaccctca tatcatgtgg tgcgagggga tattgccacg gccaccgaag   4080

gagtgattat aaatgctgct aacagcaaag gacaacctgg cggaggggtg tgcggagcgc   4140

tgtataagaa attcccggaa agcttcgatt tacagccgat cgaagtagga aaagcgcgac   4200

tggtcaaagg tgcagctaaa catatcattc atgccgtagg accaaacttc aacaaagttt   4260

cggaggttga aggtgacaaa cagttggcag aggcttatga gtccatcgct aagattgtca   4320

acgataacaa ttacaagtca gtagcgattc cactgttgtc caccggcatc ttttccggga   4380

acaaagatcg actaacccaa tcattgaacc atttgctgac agctttagac accactgatg   4440

cagatgtagc catatactgc agggacaaga aatgggaaat gactctcaag gaagcagtgg   4500

ctaggagaga agcagtggag gagatatgca tatccgacga ctcttcagtg acagaacctg   4560

atgcagagct ggtgagggtg catccgaaga gttctttggc tggaaggaag ggctacagca   4620

caagcgatgg caaaactttc tcatatttgg aagggaccaa gtttcaccag gcggccaagg   4680

atatagcaga aattaatgcc atgtggcccg ttgcaacgga ggccaatgag caggtatgca   4740

tgtatatcct cggagaaagc atgagcagta ttaggtcgaa atgccccgtc gaagagtcgg   4800

aagcctccac accacctagc acgctgcctt gcttgtgcat ccatgccatg actccagaaa   4860

gagtacagcg cctaaaagcc tcacgtccag aacaaattac tgtgtgctca tcctttccat   4920

tgccgaagta tagaatcact ggtgtgcaga agatccaatg ctcccagcct atattgttct   4980

caccgaaagt gcctgcgtat attcatccaa ggaagtatct cgtggaaaca ccaccggtag   5040

acgagactcc ggagccatcg gcagagaacc aatccacaga ggggacacct gaacaaccac   5100

cacttataac cgaggatgag accaggacta gaacgcctga gccgatcatc atcgaagagg   5160

aagaagagga tagcataagt ttgctgtcag atggcccgac ccaccaggtg ctgcaagtcg   5220

aggcagacat tcacgggccg ccctctgtat ctagctcatc ctggtccatt cctcatgcat   5280

ccgactttga tgtggacagt ttatccatac ttgacaccct ggagggagct agcgtgacca   5340

gcggggcaac gtcagccgag actaactctt acttcgcaaa gagtatggag tttctggcgc   5400
```

```
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgtg aattcgccac catggcggga cacctggctt cggatttcgc   7620
cttctcgccc cctccaggtg gtggaggtga tgggccaggg gggccggagc cgggctgggt   7680
tgatcctcgg acctggctaa gcttccaagg ccctcctgga gggccaggaa tcgggccggg   7740
```

```
ggttgggcca ggctctgagg tgtgggggat tcccccatgc cccccgccgt atgagttctg   7800
tggggggatg gcgtactgtg ggccccaggt tggagtgggg ctagtgcccc aaggcggctt   7860
ggagacctct cagcctgagg gcgaagcagg agtcggggtg gagagcaact ccgatggggc   7920
ctccccggag ccctgcaccg tcacccctgg tgccgtgaag ctggagaagg agaagctgga   7980
gcaaaacccg gaggagtccc aggacatcaa agctctgcag aaagaactcg agcaatttgc   8040
caagctcctg aagcagaaga ggatcaccct gggatataca caggccgatg tggggctcac   8100
cctgggggtt ctatttggga aggtattcag ccaaacgacc atctgccgct ttgaggctct   8160
gcagcttagc ttcaagaaca tgtgtaagct gcggcccttg ctgcagaagt gggtggagga   8220
agctgacaac aatgaaaatc ttcaggagat atgcaaagca gaaaccctcg tgcaggcccg   8280
aaagagaaag cgaaccagta tcgagaaccg agtgagaggc aacctggaga atttgttcct   8340
gcagtgcccg aaacccacac tgcagcagat cagccacatc gcccagcagc ttgggctcga   8400
gaaggatgtg gtccgagtgt ggttctgtaa ccggcgccag aagggcaagc gatcaagcag   8460
cgactatgca caacgagagg attttgaggc tgctgggtct cctttctcag gggaccagt    8520
gtcctttcct ctggccccag ggccccattt tggtacccca ggctatggga gccctcactt   8580
cactgcactg tactcctcgg tccctttccc tgagggggaa gcctttcccc ctgtctccgt   8640
caccactctg ggctctccca tgcattcaaa ctctagtgag ggcagaggaa gtctgctaac   8700
atgcggtgac gtcgaggaga atcctggccc acaattgatg gctgtcagcg acgcgctgct   8760
cccatctttc tccacgttcg cgtctggccc ggcgggaagg gagaagacac tgcgtcaagc   8820
aggtgccccg aataaccgct ggcgggagga gctctcccac atgaagcgac ttcccccagt   8880
gcttcccggc cgcccctatg acctggcggc ggcgaccgtg gccacagacc tggagagcgg   8940
cggagccggt gcggcttgcg gcggtagcaa cctggcgccc ctacctcgga gagagaccga   9000
ggagttcaac gatctcctgg acctggactt tattctctcc aattcgctga cccatcctcc   9060
ggagtcagtg gccgccaccg tgtcctcgtc agcgtcagcc tcctcttcgt cgtcgccgtc   9120
gagcagcggc cctgccagcg cgccctccac ctgcagcttc acctatccga tccgggccgg   9180
gaacgacccg ggcgtggcgc cgggcggcac gggcggaggc ctcctctatg gcagggagtc   9240
cgctcccccct ccgacggctc ccttcaacct ggcggacatc aacgacgtga gcccctcggg   9300
cggcttcgtg gccgagctcc tgcggccaga attggacccg gtgtacattc cgccgcagca   9360
gccgcagccg ccaggtggcg ggctgatggg caagttcgtg ctgaaggcgt cgctgagcgc   9420
ccctggcagc gagtacggca gcccgtcggt catcagcgtc agcaaaggca gccctgacgg   9480
cagccacccg gtggtggtgg cgccctacaa cggcgggccg ccgcgcacgt gccccaagat   9540
caagcaggag gcggtctctt cgtgcaccca cttgggcgct ggaccccctc tcagcaatgg   9600
ccaccggccg gctgcacacg acttcccccct ggggcggcag ctccccagca ggactacccc   9660
gaccctgggt cttgaggaag tgctgagcag cagggactgt caccctgccc tgccgcttcc   9720
tcccggcttc catccccacc cggggcccaa ttacccatcc ttcctgcccg atcagatgca   9780
gccgcaagtc ccgccgctcc attaccaaga gctcatgcca cccggttcct gcatgccaga   9840
ggagcccaag ccaaagaggg gaagacgatc gtggccccgg aaaaggaccg ccacccacac   9900
ttgtgattac gcgggctgcg gcaaaaccta cacaaagagt tcccatctca aggcacacct   9960
gcgaacccac acaggtgaga aaccttacca ctgtgactgg gacggctgtg gatggaaatt  10020
cgcccgctca gatgaactga ccaggcacta ccgtaaacac acggggcacc gcccgttcca  10080
gtgccaaaaa tgcgaccgag cattttccag gtcggaccac ctcgccttac acatgaagag  10140
```

```
gcatttttct agacaatgta ctaactacgc tttgttgaaa ctcgctggcg atgttgaaag  10200
taaccccggt cctggcgcgc ccatgtacaa catgatggag acggagctga agccgccggg  10260
cccgcagcaa acttcggggg gcggcggcgg caactccacc gcggcggcgg ccggcggcaa  10320
ccagaaaaac agcccggacc gcgtcaagcg gcccatgaat gccttcatgg tgtggtcccg  10380
cgggcagcgg cgcaagatgg cccaggagaa ccccaagatg cacaactcgg agatcagcaa  10440
gcgcctgggc gccgagtgga aacttttgtc ggagacggag aagcggccgt tcatcgacga  10500
ggctaagcgg ctgcgagcgc tgcacatgaa ggagcacccg gattataaat accggccccg  10560
gcggaaaacc aagacgctca tgaagaagga taagtacacg ctgcccggcg ggctgctggc  10620
ccccggcggc aatagcatgg cgagcggggt cggggtgggc gccggcctgg gcgcgggcgt  10680
gaaccagcgc atggacagtt acgcgcacat gaacggctgg agcaacggca gctacagcat  10740
gatgcaggac cagctgggct acccgcagca cccgggcctc aatgcgcacg gcgcagcgca  10800
gatgcagccc atgcaccgct acgacgtgag cgccctgcag tacaactcca tgaccagctc  10860
gcagacctac atgaacggct cgcccaccta cagcatgtcc tactcgcagc agggcacccc  10920
tggcatggct cttggctcca tgggttcggt ggtcaagtcc gaggccagct ccagcccccc  10980
tgtggttacc tcttcctccc actccagggc gccctgccag gccggggacc tccgggacat  11040
gatcagcatg tatctccccg gcgccgaggt gccggaaccc gccgccccca gcagacttca  11100
catgtcccag cactaccaga gcggcccggt gcccggcacg gccattaacg gcacactgcc  11160
cctctcacac atgtgagcgg ccatcgatgt cgacaactaa cttaagctag caacggtttc  11220
cctctagcgg gatcaattcc gccccccccc cctaacgtta ctggccgaag ccgcttggaa  11280
taaggccggt gtgcgtttgt ctatatgtta ttttccacca tattgccgtc ttttggcaat  11340
gtgagggccc ggaaacctgg ccctgtcttc ttgacgagca ttcctagggg tctttcccct  11400
ctcgccaaag gaatgcaagg tctgttgaat gtcgtgaagg aagcagttcc tctggaagct  11460
tcttgaagac aaacaacgtc tgtagcgacc ctttgcaggc agcggaaccc cccacctggc  11520
gacaggtgcc tctgcggcca aaagccacgt gtataagata cacctgcaaa ggcggcacaa  11580
ccccagtgcc acgttgtgag ttggatagtt gtggaaagag tcaaatggct ctcctcaagc  11640
gtattcaaca aggggctgaa ggatgcccag aaggtacccc attgtatggg atctgatctg  11700
gggcctcggt gcacatgctt tacatgtgtt tagtcgaggt taaaaaaacg tctaggcccc  11760
ccgaaccacg gggacgtggt tttcctttga aaaacacgat aataccaatt cgccaccatg  11820
ggcccctca acgttagctt caccaacagg aactatgacc tcgactacga ctcggtgcag  11880
ccgtatttct actgcgacga ggaggagaac ttctaccagc agcagcagca gagcgagctg  11940
cagcccccgg cgcccagcga ggatatctgg aagaaattcg agctgctgcc cacccccgccc  12000
ctgtccccta gccgccgctc cgggctctgc tcgccctcct acgttgcggt cacacccttc  12060
tcccttcggg gagacaacga cggcggtggc gggagcttct ccacggccga ccagctggag  12120
atggtgaccg agctgctggg aggagacatg gtgaaccaga gtttcatctg cgacccggac  12180
gacgagacct tcatcaaaaa catcatcatc caggactgta tgtggagcgg cttctcggcc  12240
gccgccaagc tcgtctcaga gaagctggcc tcctaccagg ctgcgcgcaa agacagcggc  12300
agcccgaacc ccgcccgcgg ccacagcgtc tgctccacct ccagcttgta cctgcaggat  12360
ctgagcgccg ccgcctcaga gtgcatcgac ccctcggtgg tcttccccta ccctctcaac  12420
gacagcagct cgcccaagtc ctgcgcctcg caagactcca gcgccttctc tccgtcctcg  12480
```

```
gattctctgc tctcctcgac ggagtcctcc ccgcagggca gccccgagcc cctggtgctc  12540
catgaggaga caccgcccac caccagcagc gactctgagg aggaacaaga agatgaggaa  12600
gaaatcgatg ttgtttctgt ggaaaagagg caggctcctg gcaaaaggtc agagtctgga  12660
tcaccttctg ctggaggcca cagcaaacct cctcacagcc cactggtcct caagaggtgc  12720
cacgtctcca cacatcagca caactacgca gcgcctccct ccactcggaa ggactatcct  12780
gctgccaaga gggtcaagtt ggacagtgtc agagtcctga gacagatcag caacaaccga  12840
aaatgcacca gccccaggtc ctcggacacc gaggagaatg tcaagaggcg aacacacaac  12900
gtcttggagc gccagaggag gaacgagcta aaacggagct tttttgccct gcgtgaccag  12960
atcccggagt tggaaaacaa tgaaaaggcc cccaaggtag ttatccttaa aaaagccaca  13020
gcatacatcc tgtccgtcca agcagaggag caaaagctca tttctgaaga ggacttgttg  13080
cggaaacgac gagaacagtt gaaacacaaa cttgaacagc tacggaactc ttgtgcgtaa  13140
tctagagtcg acccgggcgg ccgcaactaa cttaagctag caacggtttc cctctagcgg  13200
gatcaattcc gccccccccc cctaacgtta ctggccgaag ccgcttggaa taaggccggt  13260
gtgcgtttgt ctatatgtta ttttccacca tattgccgtc ttttggcaat gtgagggccc  13320
ggaaacctgg ccctgtcttc ttgacgagca ttcctagggg tctttcccct ctcgccaaag  13380
gaatgcaagg tctgttgaat gtcgtgaagg aagcagttcc tctggaagct tcttgaagac  13440
aaacaacgtc tgtagcgacc ctttgcaggc agcggaaccc cccacctggc gacaggtgcc  13500
tctgcggcca aaagccacgt gtataagata cacctgcaaa ggcggcacaa ccccagtgcc  13560
acgttgtgag ttggatagtt gtggaaagag tcaaatggct ctcctcaagc gtattcaaca  13620
aggggctgaa ggatgcccag aaggtacccc attgtatggg atctgatctg gggcctcggt  13680
gcacatgctt tacatgtgtt tagtcgaggt taaaaaaacg tctaggcccc ccgaaccacg  13740
gggacgtggt tttcctttga aaaacacgat aataccatga ccgagtacaa gcccacggtg  13800
cgcctcgcca cccgcgacga cgtccccagg gccgtacgca ccctcgccgc cgcgttcgcc  13860
gactaccccg ccacgcgcca caccgtcgat ccggaccgcc acatcgagcg ggtcaccgag  13920
ctgcaagaac tcttcctcac gcgcgtcggg ctcgacatcg gcaaggtgtg ggtcgcggac  13980
gacggcgccg cggtggcggt ctggaccacg ccggagagcg tcgaagcggg ggcggtgttc  14040
gccgagatcg gcccgcgcat ggccgagttg agcggttccc ggctggccgc gcagcaacag  14100
atggaaggcc tcctggcgcc gcaccggccc aaggagcccg cgtggttcct ggccaccgtc  14160
ggcgtctcgc ccgaccacca gggcaagggt ctgggcagcg ccgtcgtgct ccccggagtg  14220
gaggcggccg agcgcgccgg ggtgcccgcc ttcctggaga cctccgcgcc ccgcaacctc  14280
cccttctacg agcggctcgg cttcaccgtc accgccgacg tcgaggtgcc cgaaggaccg  14340
cgcacctggt gcatgacccg caagcccggt gcctgagaat tggcaagctg cttacataga  14400
actcgcggcg attggcatgc cgccttaaaa tttttatttt atttttcttt tcttttccga  14460
atcggatttt gtttttaata tttcaaaaaa aaaaaaaaaa aaaaaaaaaa cgcgtcgagg  14520
ggaattaatt cttgaagacg aaagggccag gtggcacttt tcggggaaat gtgcgcggaa  14580
cccctatttg tttatttttc taaatacatt caaatatgta tccgctcatg agacaataac  14640
cctgataaat gcttcaataa tattgaaaaa ggaagagtat gagtattcaa catttccgtg  14700
tcgcccttat tccctttttt gcggcatttt gccttcctgt ttttgctcac ccagaaacgc  14760
tggtgaaagt aaaagatgct gaagatcagt tgggtgcacg agtgggttac atcgaactgg  14820
atctcaacag cggtaagatc cttgagagtt ttcgccccga agaacgtttt ccaatgatga  14880
```

```
gcacttttaa agttctgcta tgtggcgcgg tattatcccg tgttgacgcc gggcaagagc  14940

aactcggtcg ccgcatacac tattctcaga atgacttggt tgagtactca ccagtcacag  15000

aaaagcatct tacggatggc atgacagtaa gagaattatg cagtgctgcc ataaccatga  15060

gtgataacac tgcggccaac ttacttctga caacgatcgg aggaccgaag gagctaaccg  15120

ctttttttgca caacatgggg gatcatgtaa ctcgccttga tcgttgggaa ccggagctga  15180

atgaagccat accaaacgac gagcgtgaca ccacgatgcc tgtagcaatg gcaacaacgt  15240

tgcgcaaact attaactggc gaactactta ctctagcttc ccggcaacaa ttaatagact  15300

ggatggaggc ggataaagtt gcaggaccac ttctgcgctc ggcccttccg gctggctggt  15360

ttattgctga taaatctgga gccggtgagc gtgggtctcg cggtatcatt gcagcactgg  15420

ggccagatgg taagccctcc cgtatcgtag ttatctacac gacggggagt caggcaacta  15480

tggatgaacg aaatagacag atcgctgaga taggtgcctc actgattaag cattggtaac  15540

tgtcagacca agtttactca tatatacttt agattgattt aaaacttcat ttttaattta  15600

aaaggatcta ggtgaagatc ctttttgata atctcatgac caaaatccct taacgtgagt  15660

tttcgttcca ctgagcgtca gaccccgtag aaaagatcaa aggatcttct tgagatcctt  15720

tttttctgcg cgtaatctgc tgcttgcaaa caaaaaaacc accgctacca gcggtggttt  15780

gtttgccgga tcaagagcta ccaactcttt ttccgaaggt aactggcttc agcagagcgc  15840

agataccaaa tactgtcctt ctagtgtagc cgtagttagg ccaccacttc aagaactctg  15900

tagcaccgcc tacatacctc gctctgctaa tcctgttacc agtggctgct gccagtggcg  15960

ataagtcgtg tcttaccggg ttggactcaa gacgatagtt accggataag gcgcagcggt  16020

cgggctgaac ggggggttcg tgcacacagc ccagcttgga gcgaacgacc tacaccgaac  16080

tgagatacct acagcgtgag cattgagaaa gcgccacgct tcccgaaggg agaaaggcgg  16140

acaggtatcc ggtaagcggc agggtcggaa caggagagcg cacgagggag cttccagggg  16200

gaaacgcctg gtatctttat agtcctgtcg ggtttcgcca cctctgactt gagcgtcgat  16260

ttttgtgatg ctcgtcaggg gggcggagcc tatggaaaaa cgccagcaac gcgagctcga  16320

tttaggtgac actatag                                                 16337
```

<210> SEQ ID NO 30
<211> LENGTH: 16336
<212> TYPE: DNA
<213> ORGANISM: Artificial Sequence
<220> FEATURE:
<223> OTHER INFORMATION: VEE-Oct-Klf-Sox-cMyc-T7promoter

<400> SEQUENCE: 30

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540
```

```
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
```

```
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
```

```
ccgactttga tgtggacagt ttatccatac ttgacaccct ggagggagct agcgtgacca   5340

gcggggcaac gtcagccgag actaactctt acttcgcaaa gagtatggag tttctggcgc   5400

gaccggtgcc tgcgcctcga acagtattca ggaaccctcc acatcccgct ccgcgcacaa   5460

gaacaccgtc acttgcaccc agcagggcct gctcgagaac cagcctagtt tccaccccgc   5520

caggcgtgaa tagggtgatc actagagagg agctcgaggc gcttaccccg tcacgcactc   5580

ctagcaggtc ggtctcgaga accagcctgg tctccaaccc gccaggcgta aatagggtga   5640

ttacaagaga ggagtttgag gcgttcgtag cacaacaaca atgacggttt gatgcgggtg   5700

catacatctt ttcctccgac accggtcaag ggcatttaca acaaaaatca gtaaggcaaa   5760

cggtgctatc cgaagtggtg ttggagagga ccgaattgga gatttcgtat gccccgcgcc   5820

tcgaccaaga aaaagaagaa ttactacgca agaaattaca gttaaatccc acacctgcta   5880

acagaagcag ataccagtcc aggaaggtgg agaacatgaa agccataaca gctagacgta   5940

ttctgcaagg cctagggcat tatttgaagg cagaaggaaa agtggagtgc taccgaaccc   6000

tgcatcctgt tcctttgtat tcatctagtg tgaaccgtgc cttttcaagc cccaaggtcg   6060

cagtggaagc ctgtaacgcc atgttgaaag agaactttcc gactgtggct tcttactgta   6120

ttattccaga gtacgatgcc tatttggaca tggttgacgg agcttcatgc tgcttagaca   6180

ctgccagttt ttgccctgca aagctgcgca gctttccaaa gaaacactcc tatttggaac   6240

ccacaatacg atcggcagtg ccttcagcga tccagaacac gctccagaac gtcctggcag   6300

ctgccacaaa aagaaattgc aatgtcacgc aaatgagaga attgcccgta ttggattcgg   6360

cggcctttaa tgtggaatgc ttcaagaaat atgcgtgtaa taatgaatat tgggaaacgt   6420

ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga ccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

ggcccctat aactctctac ggctaacctg aatggactac gacatagtct agtccgccaa   7560

gtctagcata tgggcgcgtg aattcgccac catggcggga cacctggctt cggatttcgc   7620

cttctcgccc cctccaggtg gtggaggtga tgggccaggg ggccggagc cgggctgggt   7680
```

```
tgatcctcgg acctggctaa gcttccaagg ccctcctgga gggccaggaa tcgggccggg   7740
ggttgggcca ggctctgagg tgtgggggat tcccccatgc cccccgccgt atgagttctg   7800
tggggggatg gcgtactgtg ggccccaggt tggagtgggg ctagtgcccc aaggcggctt   7860
ggagacctct cagcctgagg gcgaagcagg agtcggggtg gagagcaact ccgatggggc   7920
ctccccggag ccctgcaccg tcacccctgg tgccgtgaag ctggagaagg agaagctgga   7980
gcaaaacccg gaggagtccc aggacatcaa agctctgcag aaagaactcg agcaatttgc   8040
caagctcctg aagcagaaga ggatcaccct gggatataca caggccgatg tggggctcac   8100
cctgggggtt ctatttggga aggtattcag ccaaacgacc atctgccgct ttgaggctct   8160
gcagcttagc ttcaagaaca tgtgtaagct gcggcccttg ctgcagaagt gggtggagga   8220
agctgacaac aatgaaaatc ttcaggagat atgcaaagca gaaaccctcg tgcaggcccg   8280
aaagagaaag cgaaccagta tcgagaaccg agtgagaggc aacctggaga atttgttcct   8340
gcagtgcccg aaacccacac tgcagcagat cagccacatc gcccagcagc ttgggctcga   8400
gaaggatgtg gtccgagtgt ggttctgtaa ccggcgccag aagggcaagc gatcaagcag   8460
cgactatgca caacgagagg attttgaggc tgctgggtct cctttctcag ggggaccagt   8520
gtcctttcct ctggccccag ggccccattt tggtacccca ggctatggga gccctcactt   8580
cactgcactg tactcctcgg tccctttccc tgagggggaa gcctttcccc ctgtctccgt   8640
caccactctg ggctctccca tgcattcaaa ctctagtgag ggcagaggaa gtctgctaac   8700
atgcggtgac gtcgaggaga atcctggccc acaattgatg gctgtcagcg acgcgctgct   8760
cccatctttc tccacgttcg cgtctggccc ggcgggaagg gagaagacac tgcgtcaagc   8820
aggtgccccg aataaccgct ggcgggagga gctctcccac atgaagcgac ttcccccagt   8880
gcttcccggc cgcccctatg acctggcggc ggcgaccgtg gccacagacc tggagagcgg   8940
cggagccggt gcggcttgcg gcggtagcaa cctggcgccc ctacctcgga gagagaccga   9000
ggagttcaac gatctcctgg acctggactt tattctctcc aattcgctga cccatcctcc   9060
ggagtcagtg gccgccaccg tgtcctcgtc agcgtcagcc tcctcttcgt cgtcgccgtc   9120
gagcagcggc cctgccagcg cgccctccac ctgcagcttc acctatccga tccgggccgg   9180
gaacgacccg ggcgtggcgc cgggcggcac gggcggaggc ctcctctatg gcagggagtc   9240
cgctccccct ccgacggctc ccttcaacct ggcggacatc aacgacgtga gcccctcggg   9300
cggcttcgtg gccgagctcc tgcggccaga attggacccg gtgtacattc cgccgcagca   9360
gccgcagccg ccaggtggcg ggctgatggg caagttcgtg ctgaaggcgt cgctgagcgc   9420
ccctggcagc gagtacggca gcccgtcggt catcagcgtc agcaaaggca gccctgacgg   9480
cagccacccg gtggtggtgg cgccctacaa cggcgggccg ccgcgcacgt gccccaagat   9540
caagcaggag gcggtctctt cgtgcaccca cttgggcgct ggaccccctc tcagcaatgg   9600
ccaccggccg gctgcacacg acttccccct ggggcggcag ctccccagca ggactacccc   9660
gaccctgggt cttgaggaag tgctgagcag cagggactgt caccctgccc tgccgcttcc   9720
tcccggcttc catccccacc cggggcccaa ttacccatcc ttcctgcccg atcagatgca   9780
gccgcaagtc ccgccgctcc attaccaaga gctcatgcca cccggttcct gcatgccaga   9840
ggagcccaag ccaaagaggg gaagacgatc gtggccccgg aaaaggaccg ccacccacac   9900
ttgtgattac gcgggctgcg gcaaaaccta cacaaagagt tcccatctca aggcacacct   9960
gcgaacccac acaggtgaga aaccttacca ctgtgactgg gacggctgtg gatggaaatt  10020
```

```
cgcccgctca gatgaactga ccaggcacta ccgtaaacac acggggcacc gcccgttcca  10080
gtgccaaaaa tgcgaccgag cattttccag gtcggaccac ctcgccttac acatgaagag  10140
gcatttttct agacaatgta ctaactacgc tttgttgaaa ctcgctggcg atgttgaaag  10200
taaccccggt cctggcgcgc ccatgtacaa catgatggag acggagctga agccgccggg  10260
cccgcagcaa acttcggggg gcggcggcgg caactccacc gcggcggcgg ccggcggcaa  10320
ccagaaaaac agcccggacc gcgtcaagcg gcccatgaat gccttcatgg tgtggtcccg  10380
cgggcagcgg cgcaagatgg cccaggagaa ccccaagatg cacaactcgg agatcagcaa  10440
gcgcctgggc gccgagtgga aacttttgtc ggagacggag aagcggccgt tcatcgacga  10500
ggctaagcgg ctgcgagcgc tgcacatgaa ggagcacccg gattataaat accggccccg  10560
gcggaaaacc aagacgctca tgaagaagga taagtacacg ctgcccggcg ggctgctggc  10620
ccccggcggc aatagcatgg cgagcggggt cggggtgggc gccggcctgg gcgcgggcgt  10680
gaaccagcgc atggacagtt acgcgcacat gaacggctgg agcaacggca gctacagcat  10740
gatgcaggac cagctgggct acccgcagca cccgggcctc aatgcgcacg gcgcagcgca  10800
gatgcagccc atgcaccgct acgacgtgag cgccctgcag tacaactcca tgaccagctc  10860
gcagacctac atgaacggct cgcccaccta cagcatgtcc tactcgcagc agggcacccc  10920
tggcatggct cttggctcca tgggttcggt ggtcaagtcc gaggccagct ccagcccccc  10980
tgtggttacc tcttcctccc actccagggc gccctgccag gccggggacc tccgggacat  11040
gatcagcatg tatctccccg gcgccgaggt gccggaaccc gccgccccca gcagacttca  11100
catgtcccag cactaccaga gcggcccggt gcccggcacg gccattaacg gcacactgcc  11160
cctctcacac atgtgagcgg ccatcgatgt cgacaactaa cttaagctag caacggtttc  11220
cctctagcgg gatcaattcc gccccccccc cctaacgtta ctggccgaag ccgcttggaa  11280
taaggccggt gtgcgtttgt ctatatgtta ttttccacca tattgccgtc ttttggcaat  11340
gtgagggccc ggaaacctgg ccctgtcttc ttgacgagca ttcctagggg tctttcccct  11400
ctcgccaaag gaatgcaagg tctgttgaat gtcgtgaagg aagcagttcc tctggaagct  11460
tcttgaagac aaacaacgtc tgtagcgacc ctttgcaggc agcggaaccc cccacctggc  11520
gacaggtgcc tctgcggcca aaagccacgt gtataagata cacctgcaaa ggcggcacaa  11580
ccccagtgcc acgttgtgag ttggatagtt gtggaaagag tcaaatggct ctcctcaagc  11640
gtattcaaca aggggctgaa ggatgcccag aaggtacccc attgtatggg atctgatctg  11700
gggcctcggt gcacatgctt tacatgtgtt tagtcgaggt taaaaaaacg tctaggcccc  11760
ccgaaccacg gggacgtggt tttcctttga aaaacacgat aataccaatt cgccaccatg  11820
ggccccctca acgttagctt caccaacagg aactatgacc tcgactacga ctcggtgcag  11880
ccgtatttct actgcgacga ggaggagaac ttctaccagc agcagcagca gagcgagctg  11940
cagcccccgg cgcccagcga ggatatctgg aagaaattcg agctgctgcc caccccgccc  12000
ctgtccccta gccgccgctc cgggctctgc tcgccctcct acgttgcggt cacacccttc  12060
tcccttcggg gagacaacga cggcggtggc gggagcttct ccacggccga ccagctggag  12120
atggtgaccg agctgctggg aggagacatg gtgaaccaga gtttcatctg cgacccggac  12180
gacgagacct tcatcaaaaa catcatcatc caggactgta tgtggagcgg cttctcggcc  12240
gccgccaagc tcgtctcaga gaagctggcc tcctaccagg ctgcgcgcaa agacagcggc  12300
agcccgaacc ccgcccgcgg ccacagcgtc tgctccacct ccagcttgta cctgcaggat  12360
ctgagcgccg ccgcctcaga gtgcatcgac ccctcggtgg tcttccccta ccctctcaac  12420
```

```
gacagcagct cgcccaagtc ctgcgcctcg caagactcca gcgccttctc tccgtcctcg  12480
gattctctgc tctcctcgac ggagtcctcc ccgcagggca gccccgagcc cctggtgctc  12540
catgaggaga caccgcccac caccagcagc gactctgagg aggaacaaga agatgaggaa  12600
gaaatcgatg ttgtttctgt ggaaaagagg caggctcctg gcaaaaggtc agagtctgga  12660
tcaccttctg ctggaggcca cagcaaacct cctcacagcc cactggtcct caagaggtgc  12720
cacgtctcca cacatcagca caactacgca gcgcctccct ccactcggaa ggactatcct  12780
gctgccaaga gggtcaagtt ggacagtgtc agagtcctga gacagatcag caacaaccga  12840
aaatgcacca gccccaggtc ctcggacacc gaggagaatg tcaagaggcg aacacacaac  12900
gtcttggagc gccagaggag gaacgagcta aaacggagct tttttgccct gcgtgaccag  12960
atcccggagt tggaaaacaa tgaaaaggcc cccaaggtag ttatccttaa aaaagccaca  13020
gcatacatcc tgtccgtcca agcagaggag caaaagctca tttctgaaga ggacttgttg  13080
cggaaacgac gagaacagtt gaaacacaaa cttgaacagc tacggaactc ttgtgcgtaa  13140
tctagagtcg acccgggcgg ccgcaactaa cttaagctag caacggtttc cctctagcgg  13200
gatcaattcc gcccccccccc cctaacgtta ctggccgaag ccgcttggaa taaggccggt  13260
gtgcgtttgt ctatatgtta ttttccacca tattgccgtc ttttggcaat gtgagggccc  13320
ggaaacctgg ccctgtcttc ttgacgagca ttcctagggg tctttcccct ctcgccaaag  13380
gaatgcaagg tctgttgaat gtcgtgaagg aagcagttcc tctggaagct tcttgaagac  13440
aaacaacgtc tgtagcgacc ctttgcaggc agcggaaccc cccacctggc gacaggtgcc  13500
tctgcggcca aaagccacgt gtataagata cacctgcaaa ggcggcacaa ccccagtgcc  13560
acgttgtgag ttggatagtt gtggaaagag tcaaatggct ctcctcaagc gtattcaaca  13620
aggggctgaa ggatgcccag aaggtacccc attgtatggg atctgatctg gggcctcggt  13680
gcacatgctt tacatgtgtt tagtcgaggt taaaaaaacg tctaggcccc ccgaaccacg  13740
gggacgtggt tttcctttga aaaacacgat aataccatga ccgagtacaa gcccacggtg  13800
cgcctcgcca cccgcgacga cgtccccagg gccgtacgca ccctcgccgc cgcgttcgcc  13860
gactaccccg ccacgcgcca caccgtcgat ccggaccgcc acatcgagcg ggtcaccgag  13920
ctgcaagaac tcttcctcac gcgcgtcggg ctcgacatcg gcaaggtgtg ggtcgcggac  13980
gacggcgccg cggtggcggt ctggaccacg ccggagagcg tcgaagcggg ggcggtgttc  14040
gccgagatcg gcccgcgcat ggccgagttg agcggttccc ggctggccgc gcagcaacag  14100
atggaaggcc tcctggcgcc gcaccggccc aaggagcccg cgtggttcct ggccaccgtc  14160
ggcgtctcgc ccgaccacca gggcaagggt ctgggcagcg ccgtcgtgct ccccggagtg  14220
gaggcggccg agcgcgccgg ggtgcccgcc ttcctggaga cctccgcgcc ccgcaacctc  14280
cccttctacg agcggctcgg cttcaccgtc accgccgacg tcgaggtgcc cgaaggaccg  14340
cgcacctggt gcatgacccg caagcccggt gcctgagaat tggcaagctg cttacataga  14400
actcgcggcg attggcatgc cgccttaaaa tttttatttt atttttcttt tcttttccga  14460
atcggatttt gtttttaata tttcaaaaaa aaaaaaaaaa aaaaaaaaaa cgcgtcgagg  14520
ggaattaatt cttgaagacg aaagggccag gtggcacttt tcggggaaat gtgcgcggaa  14580
cccctatttg tttatttttc taaatacatt caaatatgta tccgctcatg agacaataac  14640
cctgataaat gcttcaataa tattgaaaaa ggaagagtat gagtattcaa catttccgtg  14700
tcgcccttat tccctttttt gcggcatttt gccttcctgt ttttgctcac ccagaaacgc  14760
```

```
tggtgaaagt aaaagatgct gaagatcagt tgggtgcacg agtgggttac atcgaactgg  14820

atctcaacag cggtaagatc cttgagagtt ttcgccccga agaacgtttt ccaatgatga  14880

gcacttttaa agttctgcta tgtggcgcgg tattatcccg tgttgacgcc gggcaagagc  14940

aactcggtcg ccgcatacac tattctcaga atgacttggt tgagtactca ccagtcacag  15000

aaaagcatct tacggatggc atgacagtaa gagaattatg cagtgctgcc ataaccatga  15060

gtgataacac tgcggccaac ttacttctga caacgatcgg aggaccgaag gagctaaccg  15120

ctttttgca caacatgggg gatcatgtaa ctcgccttga tcgttgggaa ccggagctga  15180

atgaagccat accaaacgac gagcgtgaca ccacgatgcc tgtagcaatg gcaacaacgt  15240

tgcgcaaact attaactggc gaactactta ctctagcttc ccggcaacaa ttaatagact  15300

ggatggaggc ggataaagtt gcaggaccac ttctgcgctc ggcccttccg gctggctggt  15360

ttattgctga taaatctgga gccggtgagc gtgggtctcg cggtatcatt gcagcactgg  15420

ggccagatgg taagccctcc cgtatcgtag ttatctacac gacggggagt caggcaacta  15480

tggatgaacg aaatagacag atcgctgaga taggtgcctc actgattaag cattggtaac  15540

tgtcagacca agtttactca tatatacttt agattgattt aaaacttcat ttttaattta  15600

aaaggatcta ggtgaagatc ctttttgata atctcatgac caaaatccct taacgtgagt  15660

tttcgttcca ctgagcgtca gaccccgtag aaaagatcaa aggatcttct tgagatcctt  15720

tttttctgcg cgtaatctgc tgcttgcaaa caaaaaaacc accgctacca gcggtggttt  15780

gtttgccgga tcaagagcta ccaactcttt ttccgaaggt aactggcttc agcagagcgc  15840

agataccaaa tactgtcctt ctagtgtagc cgtagttagg ccaccacttc aagaactctg  15900

tagcaccgcc tacatacctc gctctgctaa tcctgttacc agtggctgct gccagtggcg  15960

ataagtcgtg tcttaccggg ttggactcaa gacgatagtt accggataag gcgcagcggt  16020

cgggctgaac ggggggttcg tgcacacagc ccagcttgga gcgaacgacc tacaccgaac  16080

tgagatacct acagcgtgag cattgagaaa gcgccacgct tcccgaaggg agaaaggcgg  16140

acaggtatcc ggtaagcggc agggtcggaa caggagagcg cacgagggag cttccagggg  16200

gaaacgcctg gtatctttat agtcctgtcg ggtttcgcca cctctgactt gagcgtcgat  16260

ttttgtgatg ctcgtcaggg gggcggagcc tatggaaaaa cgccagcaac gcgagctcta  16320

atacgactca ctatag                                                  16336
```

<210> SEQ ID NO 31
<211> LENGTH: 16861
<212> TYPE: DNA
<213> ORGANISM: Artificial Sequence
<220> FEATURE:
<223> OTHER INFORMATION: VEE-Oct-Klf-Sox-Glis-SP6

<400> SEQUENCE: 31

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480
```

```
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
```

```
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
```

```
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
```

```
gtctagcata tgggcgcgtg aattcgccac catggcggga cacctggctt cggatttcgc   7620
cttctcgccc cctccaggtg gtggaggtga tgggccaggg gggccggagc cgggctgggt   7680
tgatcctcgg acctggctaa gcttccaagg ccctcctgga gggccaggaa tcgggccggg   7740
ggttgggcca ggctctgagg tgtgggggat tcccccatgc cccccgccgt atgagttctg   7800
tggggggatg gcgtactgtg ggccccaggt tggagtgggg ctagtgcccc aaggcggctt   7860
ggagacctct cagcctgagg gcgaagcagg agtcggggtg gagagcaact ccgatggggc   7920
ctccccggag ccctgcaccg tcacccctgg tgccgtgaag ctggagaagg agaagctgga   7980
gcaaaacccg gaggagtccc aggacatcaa agctctgcag aaagaactcg agcaatttgc   8040
caagctcctg aagcagaaga ggatcaccct gggatataca caggccgatg tggggctcac   8100
cctgggggtt ctatttggga aggtattcag ccaaacgacc atctgccgct ttgaggctct   8160
gcagcttagc ttcaagaaca tgtgtaagct gcggcccttg ctgcagaagt gggtggagga   8220
agctgacaac aatgaaaatc ttcaggagat atgcaaagca gaaaccctcg tgcaggcccg   8280
aaagagaaag cgaaccagta tcgagaaccg agtgagaggc aacctggaga atttgttcct   8340
gcagtgcccg aaacccacac tgcagcagat cagccacatc gcccagcagc ttgggctcga   8400
gaaggatgtg gtccgagtgt ggttctgtaa ccggcgccag aagggcaagc gatcaagcag   8460
cgactatgca caacgagagg attttgaggc tgctgggtct cctttctcag gggaccagt    8520
gtcctttcct ctggccccag ggccccattt tggtacccca ggctatggga gccctcactt   8580
cactgcactg tactcctcgg tccctttccc tgagggggaa gcctttcccc ctgtctccgt   8640
caccactctg ggctctccca tgcattcaaa ctctagtgag ggcagaggaa gtctgctaac   8700
atgcggtgac gtcgaggaga atcctggccc acaattgatg gctgtcagcg acgcgctgct   8760
cccatctttc tccacgttcg cgtctggccc ggcgggaagg gagaagacac tgcgtcaagc   8820
aggtgccccg aataaccgct ggcgggagga gctctcccac atgaagcgac ttcccccagt   8880
gcttcccggc cgcccctatg acctggcggc ggcgaccgtg gccacagacc tggagagcgg   8940
cggagccggt gcggcttgcg gcggtagcaa cctggcgccc ctacctcgga gagagaccga   9000
ggagttcaac gatctcctgg acctggactt tattctctcc aattcgctga cccatcctcc   9060
ggagtcagtg gccgccaccg tgtcctcgtc agcgtcagcc tcctcttcgt cgtcgccgtc   9120
gagcagcggc cctgccagcg cgccctccac ctgcagcttc acctatccga tccgggccgg   9180
gaacgacccg ggcgtggcgc cgggcggcac gggcggaggc ctcctctatg gcagggagtc   9240
cgctccccct ccgacggctc ccttcaacct ggcggacatc aacgacgtga gcccctcggg   9300
cggcttcgtg gccgagctcc tgcggccaga attggacccg gtgtacattc cgccgcagca   9360
gccgcagccg ccaggtggcg ggctgatggg caagttcgtg ctgaaggcgt cgctgagcgc   9420
ccctggcagc gagtacggca gcccgtcggt catcagcgtc agcaaaggca gccctgacgg   9480
cagccacccg gtggtggtgg cgccctacaa cggcgggccg ccgcgcacgt gccccaagat   9540
caagcaggag gcggtctctt cgtgcaccca cttgggcgct ggaccccctc tcagcaatgg   9600
ccaccggccg gctgcacacg acttccccct ggggcggcag ctccccagca ggactacccc   9660
gaccctgggt cttgaggaag tgctgagcag cagggactgt caccctgccc tgccgcttcc   9720
tcccggcttc catccccacc cggggcccaa ttacccatcc ttcctgcccg atcagatgca   9780
gccgcaagtc ccgccgctcc attaccaaga gctcatgcca cccggttcct gcatgccaga   9840
ggagcccaag ccaaagaggg gaagacgatc gtggccccgg aaaaggaccg ccacccacac   9900
ttgtgattac gcgggctgcg gcaaaaccta cacaaagagt tcccatctca aggcacacct   9960
```

```
gcgaacccac acaggtgaga aaccttacca ctgtgactgg gacggctgtg gatggaaatt  10020
cgcccgctca gatgaactga ccaggcacta ccgtaaacac acggggcacc gcccgttcca  10080
gtgccaaaaa tgcgaccgag cattttccag gtcggaccac ctcgccttac acatgaagag  10140
gcatttttct agacaatgta ctaactacgc tttgttgaaa ctcgctggcg atgttgaaag  10200
taaccccggt cctggcgcgc ccatgtacaa catgatggag acggagctga agccgccggg  10260
cccgcagcaa acttcggggg gcggcggcgg caactccacc gcggcggcgg ccggcggcaa  10320
ccagaaaaac agcccggacc gcgtcaagcg gcccatgaat gccttcatgg tgtggtcccg  10380
cgggcagcgg cgcaagatgg cccaggagaa ccccaagatg cacaactcgg agatcagcaa  10440
gcgcctgggc gccgagtgga aacttttgtc ggagacggag aagcggccgt tcatcgacga  10500
ggctaagcgg ctgcgagcgc tgcacatgaa ggagcacccg gattataaat accggccccg  10560
gcggaaaacc aagacgctca tgaagaagga taagtacacg ctgcccggcg ggctgctggc  10620
ccccggcggc aatagcatgg cgagcggggt cggggtgggc gccggcctgg gcgcgggcgt  10680
gaaccagcgc atggacagtt acgcgcacat gaacggctgg agcaacggca gctacagcat  10740
gatgcaggac cagctgggct acccgcagca cccgggcctc aatgcgcacg gcgcagcgca  10800
gatgcagccc atgcaccgct acgacgtgag cgccctgcag tacaactcca tgaccagctc  10860
gcagacctac atgaacggct cgcccaccta cagcatgtcc tactcgcagc agggcacccc  10920
tggcatggct cttggctcca tgggttcggt ggtcaagtcc gaggccagct ccagcccccc  10980
tgtggttacc tcttcctccc actccagggc gccctgccag gccggggacc tccgggacat  11040
gatcagcatg tatctccccg gcgccgaggt gccggaaccc gccgccccca gcagacttca  11100
catgtcccag cactaccaga gcggcccggt gcccggcacg gccattaacg gcacactgcc  11160
cctctcacac atgtgagcgg ccatcgatgt cgacaactaa cttaagctag caacggtttc  11220
cctctagcgg gatcaattcc gccccccccc cctaacgtta ctggccgaag ccgcttggaa  11280
taaggccggt gtgcgtttgt ctatatgtta ttttccacca tattgccgtc ttttggcaat  11340
gtgagggccc ggaaacctgg ccctgtcttc ttgacgagca ttcctagggg tctttcccct  11400
ctcgccaaag gaatgcaagg tctgttgaat gtcgtgaagg aagcagttcc tctggaagct  11460
tcttgaagac aaacaacgtc tgtagcgacc ctttgcaggc agcggaaccc cccacctggc  11520
gacaggtgcc tctgcggcca aaagccacgt gtataagata cacctgcaaa ggcggcacaa  11580
ccccagtgcc acgttgtgag ttggatagtt gtggaaagag tcaaatggct ctcctcaagc  11640
gtattcaaca aggggctgaa ggatgcccag aaggtacccc attgtatggg atctgatctg  11700
gggcctcggt gcacatgctt tacatgtgtt tagtcgaggt taaaaaaacg tctaggcccc  11760
ccgaaccacg gggacgtggt tttcctttga aaaacacgat aataccaatt cgccaccatg  11820
gcagaggccc gcacatccct gtctgcccac tgtcggggcc cgctggccac tggcctgcac  11880
ccagacctgg acctcccggg ccgaagcctc gccacccctg cgccttcctg ctaccttctg  11940
ggcagcgaac ccagctctgg cctgggcctc cagcccgaga cccacctccc cgagggcagc  12000
ctgaagcggt gctgcgtctt gggcctaccc cccacctccc cagcctcctc ctcaccctgt  12060
gcctcctccg acgtcacctc catcatccgc tcctcccaga cgtctctggt cacctgtgta  12120
aatggactcc ggagcccccc tctgacggga gatctggggg gcccttccaa gcgggcccgg  12180
cctggccctg catcgacgga cagccatgag ggcagcttgc aacttgaagc ctgccggaag  12240
gcgagcttcc tgaagcagga acccgcggat gagttttcag agctctttgg gcctcaccag  12300
```

```
cagggcctgc cgccccccta tcccctgtct cagttgccgc ctggcccaag ccttggaggc  12360
ctggggctgg gcctggcagg cagggtggtg gccgggcggc aggcgtgccg ctgggtggac  12420
tgctgtgcag cctatgagca gcaggaggag ctggtgcggc acatcgagaa gagccacatc  12480
gaccagcgca agggcgagga cttcacctgc ttctgggctg gctgcgtgcg ccgctacaag  12540
cccttcaacg cccgctacaa gctgctcatc cacatgcgag tgcactcggg cgagaagccc  12600
aacaagtgca tgtttgaagg ctgcagcaag gccttctcac ggctggagaa cctcaagatc  12660
cacctgagga gccacacggg cgagaagccg tacctgtgcc agcacccggg ttgccagaag  12720
gccttcagca actccagcga ccgcgccaag caccagcgca cccacctaga cacgaagccg  12780
tacgcctgtc agatccctgg ctgctccaag cgctacacag accccagctc cctccgcaag  12840
cacgtcaagg cccattcagc caaagagcag caggtgcgta agaagctgca tgcgggccct  12900
gacaccgagg ccgacgtcct gaccgagtgt ctggtcctgc agcagctcca cacgtccaca  12960
cagctggctg ccagcgacgg caagggtggc tgtggcctgg gccaggagct gctcccaggt  13020
gtgtatcctg gctccatcac cccccataac ggacttgcat cgggcctcct gcccccagcg  13080
cacgacgtac cttccaggca ccacccgctg gatgccacca ccagttccca ccaccatctg  13140
tcccctctgc ccatggctga gagcacccgg gatgggttgg ggcccggcct cctctcacca  13200
atagtcagcc ccctgaaggg gctggggcca ccgccgctgc cccatcctc tcagagccat  13260
tctccggggg gccagccctt ccccacactc cccagcaagc cgtcctaccc acccttccag  13320
agccctccac ccccgcctct gcccagccca caaggttacc agggcagttt ccactccatc  13380
cagagttgct tcccctatgg cgactgctac cggatggctg aaccagcagc cggtggggac  13440
ggactggtcg gggagaccca cggtttcaac cccctgcggc ccaatggcta ccacagcctc  13500
agcacgccct tgcctgccac aggctatgag gccctggctg aggcctcatg ccccacagcg  13560
ctgccacagc agccatctga agatgtggtg tccagcggcc ccgaggactg tggcttcttc  13620
cccaatggag cctttgacca ctgcctgggc cacatcccct ccatctacac agacacctga  13680
gcggccgcaa ctaacttaag ctagcaacgg tttccctcta gcgggatcaa ttccgccccc  13740
ccccctaac gttactggcc gaagccgctt ggaataaggc cggtgtgcgt ttgtctatat  13800
gttattttcc accatattgc cgtcttttgg caatgtgagg gcccggaaac ctggccctgt  13860
cttcttgacg agcattccta ggggtctttc ccctctcgcc aaaggaatgc aaggtctgtt  13920
gaatgtcgtg aaggaagcag ttcctctgga agcttcttga agacaaacaa cgtctgtagc  13980
gaccctttgc aggcagcgga acccccacc tggcgacagg tgcctctgcg gccaaaagcc  14040
acgtgtataa gatacacctg caaaggcggc acaaccccag tgccacgttg tgagttggat  14100
agttgtggaa agagtcaaat ggctctcctc aagcgtattc aacaaggggc tgaaggatgc  14160
ccagaaggta ccccattgta tgggatctga tctggggcct cggtgcacat gctttacatg  14220
tgtttagtcg aggttaaaaa aacgtctagg ccccccgaac cacggggacg tggttttcct  14280
ttgaaaaaca cgataatacc atgaccgagt acaagcccac ggtgcgcctc gccacccgcg  14340
acgacgtccc cagggccgta cgcaccctcg ccgccgcgtt cgccgactac cccgccacgc  14400
gccacaccgt cgatccggac cgccacatcg agcgggtcac cgagctgcaa gaactcttcc  14460
tcacgcgcgt cgggctcgac atcggcaagg tgtgggtcgc ggacgacggc gccgcggtgg  14520
cggtctggac cacgccggag agcgtcgaag cgggggcggt gttcgccgag atcggcccgc  14580
gcatggccga gttgagcggt tcccggctgg ccgcgcagca acagatggaa ggcctcctgg  14640
cgccgcaccg gcccaaggag cccgcgtggt tcctggccac cgtcggcgtc tcgcccgacc  14700
```

```
accagggcaa gggtctgggc agcgccgtcg tgctccccgg agtggaggcg gccgagcgcg  14760
ccggggtgcc cgccttcctg gagacctccg cgccccgcaa cctccccttc tacgagcggc  14820
tcggcttcac cgtcaccgcc gacgtcgagg tgcccgaagg accgcgcacc tggtgcatga  14880
cccgcaagcc cggtgcctga gaattggcaa gctgcttaca tagaactcgc ggcgattggc  14940
atgccgcctt aaaattttta ttttattttt cttttctttt ccgaatcgga ttttgttttt  15000
aatatttcaa aaaaaaaaaa aaaaaaaaaa aaaacgcgtc gaggggaatt aattcttgaa  15060
gacgaaaggg ccaggtggca cttttcgggg aaatgtgcgc ggaaccccta tttgtttatt  15120
tttctaaata cattcaaata tgtatccgct catgagacaa taaccctgat aaatgcttca  15180
ataatattga aaaaggaaga gtatgagtat tcaacatttc cgtgtcgccc ttattccctt  15240
ttttgcggca ttttgccttc ctgtttttgc tcacccagaa acgctggtga aagtaaaaga  15300
tgctgaagat cagttgggtg cacgagtggg ttacatcgaa ctggatctca acagcggtaa  15360
gatccttgag agttttcgcc ccgaagaacg ttttccaatg atgagcactt ttaaagttct  15420
gctatgtggc gcggtattat cccgtgttga cgccgggcaa gagcaactcg gtcgccgcat  15480
acactattct cagaatgact tggttgagta ctcaccagtc acagaaaagc atcttacgga  15540
tggcatgaca gtaagagaat tatgcagtgc tgccataacc atgagtgata acactgcggc  15600
caacttactt ctgacaacga tcggaggacc gaaggagcta accgcttttt tgcacaacat  15660
gggggatcat gtaactcgcc ttgatcgttg ggaaccggag ctgaatgaag ccataccaaa  15720
cgacgagcgt gacaccacga tgcctgtagc aatggcaaca acgttgcgca aactattaac  15780
tggcgaacta cttactctag cttcccggca acaattaata gactggatgg aggcggataa  15840
agttgcagga ccacttctgc gctcggccct tccggctggc tggtttattg ctgataaatc  15900
tggagccggt gagcgtgggt ctcgcggtat cattgcagca ctggggccag atggtaagcc  15960
ctcccgtatc gtagttatct acacgacggg gagtcaggca actatggatg aacgaaatag  16020
acagatcgct gagataggtg cctcactgat taagcattgg taactgtcag accaagttta  16080
ctcatatata ctttagattg atttaaaact tcatttttaa tttaaaagga tctaggtgaa  16140
gatccttttt gataatctca tgaccaaaat cccttaacgt gagttttcgt tccactgagc  16200
gtcagacccc gtagaaaaga tcaaaggatc ttcttgagat cctttttttc tgcgcgtaat  16260
ctgctgcttg caaacaaaaa aaccaccgct accagcggtg gtttgtttgc cggatcaaga  16320
gctaccaact ctttttccga aggtaactgg cttcagcaga gcgcagatac caaatactgt  16380
ccttctagtg tagccgtagt taggccacca cttcaagaac tctgtagcac cgcctacata  16440
cctcgctctg ctaatcctgt taccagtggc tgctgccagt ggcgataagt cgtgtcttac  16500
cgggttggac tcaagacgat agttaccgga taaggcgcag cggtcgggct gaacgggggg  16560
ttcgtgcaca cagcccagct tggagcgaac gacctacacc gaactgagat acctacagcg  16620
tgagcattga gaaagcgcca cgcttcccga agggagaaag gcggacaggt atccggtaag  16680
cggcagggtc ggaacaggag agcgcacgag ggagcttcca gggggaaacg cctggtatct  16740
ttatagtcct gtcgggtttc gccacctctg acttgagcgt cgatttttgt gatgctcgtc  16800
aggggggcgg agcctatgga aaaacgccag caacgcgagc tcgatttagg tgacactata  16860
g                                                                 16861
```

<210> SEQ ID NO 32
<211> LENGTH: 16860
<212> TYPE: DNA

<213> ORGANISM: Artificial Sequence
<220> FEATURE:
<223> OTHER INFORMATION: VEE-Oct-Klf-Sox-Glis-T7

<400> SEQUENCE: 32

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
```

```
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
```

```
atgcagagct ggtgagggtg catccgaaga gttctttggc tggaaggaag ggctacagca   4620

caagcgatgg caaaactttc tcatatttgg aagggaccaa gtttcaccag gcggccaagg   4680

atatagcaga aattaatgcc atgtggcccg ttgcaacgga ggccaatgag caggtatgca   4740

tgtatatcct cggagaaagc atgagcagta ttaggtcgaa atgccccgtc gaagagtcgg   4800

aagcctccac accacctagc acgctgcctt gcttgtgcat ccatgccatg actccagaaa   4860

gagtacagcg cctaaaagcc tcacgtccag aacaaattac tgtgtgctca tcctttccat   4920

tgccgaagta tagaatcact ggtgtgcaga agatccaatg ctcccagcct atattgttct   4980

caccgaaagt gcctgcgtat attcatccaa ggaagtatct cgtggaaaca ccaccggtag   5040

acgagactcc ggagccatcg gcagagaacc aatccacaga ggggacacct gaacaaccac   5100

cacttataac cgaggatgag accaggacta gaacgcctga gccgatcatc atcgaagagg   5160

aagaagagga tagcataagt ttgctgtcag atggcccgac ccaccaggtg ctgcaagtcg   5220

aggcagacat tcacgggccg ccctctgtat ctagctcatc ctggtccatt cctcatgcat   5280

ccgactttga tgtggacagt ttatccatac ttgacaccct ggagggagct agcgtgacca   5340

gcggggcaac gtcagccgag actaactctt acttcgcaaa gagtatggag tttctggcgc   5400

gaccggtgcc tgcgcctcga acagtattca ggaaccctcc acatcccgct ccgcgcacaa   5460

gaacaccgtc acttgcaccc agcagggcct gctcgagaac cagcctagtt tccaccccgc   5520

caggcgtgaa tagggtgatc actagagagg agctcgaggc gcttaccccg tcacgcactc   5580

ctagcaggtc ggtctcgaga accagcctgg tctccaaccc gccaggcgta aatagggtga   5640

ttacaagaga ggagtttgag gcgttcgtag cacaacaaca atgacggttt gatgcgggtg   5700

catacatctt ttcctccgac accggtcaag ggcatttaca acaaaaatca gtaaggcaaa   5760

cggtgctatc cgaagtggtg ttggagagga ccgaattgga gatttcgtat gccccgcgcc   5820

tcgaccaaga aaaagaagaa ttactacgca agaaattaca gttaaatccc acacctgcta   5880

acagaagcag ataccagtcc aggaaggtgg agaacatgaa agccataaca gctagacgta   5940

ttctgcaagg cctagggcat tatttgaagg cagaaggaaa agtggagtgc taccgaaccc   6000

tgcatcctgt tcctttgtat tcatctagtg tgaaccgtgc cttttcaagc cccaaggtcg   6060

cagtggaagc ctgtaacgcc atgttgaaag agaactttcc gactgtggct tcttactgta   6120

ttattccaga gtacgatgcc tatttggaca tggttgacgg agcttcatgc tgcttagaca   6180

ctgccagttt ttgccctgca aagctgcgca gctttccaaa gaaacactcc tatttggaac   6240

ccacaatacg atcggcagtg ccttcagcga tccagaacac gctccagaac gtcctggcag   6300

ctgccacaaa aagaaattgc aatgtcacgc aaatgagaga attgcccgta ttggattcgg   6360

cggcctttaa tgtggaatgc ttcaagaaat atgcgtgtaa taatgaatat tgggaaacgt   6420

ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960
```

```
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgtg aattcgccac catggcggga cacctggctt cggatttcgc   7620
cttctcgccc cctccaggtg gtggaggtga tgggccaggg gggccggagc cgggctgggt   7680
tgatcctcgg acctggctaa gcttccaagg ccctcctgga gggccaggaa tcgggccggg   7740
ggttgggcca ggctctgagg tgtgggggat tcccccatgc cccccgccgt atgagttctg   7800
tggggggatg gcgtactgtg ggccccaggt tggagtgggg ctagtgcccc aaggcggctt   7860
ggagacctct cagcctgagg gcgaagcagg agtcggggtg gagagcaact ccgatggggc   7920
ctccccggag ccctgcaccg tcacccctgg tgccgtgaag ctggagaagg agaagctgga   7980
gcaaaacccg gaggagtccc aggacatcaa agctctgcag aaagaactcg agcaatttgc   8040
caagctcctg aagcagaaga ggatcaccct gggatataca caggccgatg tggggctcac   8100
cctgggggtt ctatttggga aggtattcag ccaaacgacc atctgccgct ttgaggctct   8160
gcagcttagc ttcaagaaca tgtgtaagct gcggcccttg ctgcagaagt gggtggagga   8220
agctgacaac aatgaaaatc ttcaggagat atgcaaagca gaaaccctcg tgcaggcccg   8280
aaagagaaag cgaaccagta tcgagaaccg agtgagaggc aacctggaga atttgttcct   8340
gcagtgcccg aaacccacac tgcagcagat cagccacatc gcccagcagc ttgggctcga   8400
gaaggatgtg gtccgagtgt ggttctgtaa ccggcgccag aagggcaagc gatcaagcag   8460
cgactatgca caacgagagg attttgaggc tgctgggtct cctttctcag gggaccagt   8520
gtcctttcct ctggccccag ggccccattt tggtacccca ggctatggga gccctcactt   8580
cactgcactg tactcctcgg tccctttccc tgagggggaa gcctttcccc ctgtctccgt   8640
caccactctg ggctctccca tgcattcaaa ctctagtgag ggcagaggaa gtctgctaac   8700
atgcggtgac gtcgaggaga atcctggccc acaattgatg gctgtcagcg acgcgctgct   8760
cccatctttc tccacgttcg cgtctggccc ggcgggaagg gagaagacac tgcgtcaagc   8820
aggtgccccg aataaccgct ggcgggagga gctctcccac atgaagcgac ttcccccagt   8880
gcttcccggc cgcccctatg acctggcggc ggcgaccgtg gccacagacc tggagagcgg   8940
cggagccggt gcggcttgcg gcggtagcaa cctggcgccc ctacctcgga gagagaccga   9000
ggagttcaac gatctcctgg acctggactt tattctctcc aattcgctga cccatcctcc   9060
ggagtcagtg gccgccaccg tgtcctcgtc agcgtcagcc tcctcttcgt cgtcgccgtc   9120
gagcagcggc cctgccagcg cgccctccac ctgcagcttc acctatccga tccgggccgg   9180
gaacgacccg ggcgtggcgc cgggcggcac gggcggaggc ctcctctatg gcagggagtc   9240
cgctcccccct ccgacggctc ccttcaacct ggcggacatc aacgacgtga gcccctcggg   9300
```

```
cggcttcgtg gccgagctcc tgcggccaga attggacccg gtgtacattc cgccgcagca   9360
gccgcagccg ccaggtggcg ggctgatggg caagttcgtg ctgaaggcgt cgctgagcgc   9420
ccctggcagc gagtacggca gcccgtcggt catcagcgtc agcaaaggca gccctgacgg   9480
cagccacccg gtggtggtgg cgccctacaa cggcgggccg ccgcgcacgt gccccaagat   9540
caagcaggag gcggtctctt cgtgcaccca cttgggcgct ggacccccctc tcagcaatgg   9600
ccaccggccg gctgcacacg acttcccccct ggggcggcag ctccccagca ggactacccc   9660
gaccctgggt cttgaggaag tgctgagcag cagggactgt caccctgccc tgccgcttcc   9720
tcccggcttc catccccacc cggggcccaa ttacccatcc ttcctgcccg atcagatgca   9780
gccgcaagtc ccgccgctcc attaccaaga gctcatgcca cccggttcct gcatgccaga   9840
ggagcccaag ccaaagaggg gaagacgatc gtggccccgg aaaaggaccg ccacccacac   9900
ttgtgattac gcgggctgcg gcaaaaccta cacaaagagt tcccatctca aggcacacct   9960
gcgaacccac acaggtgaga aaccttacca ctgtgactgg gacggctgtg gatggaaatt  10020
cgcccgctca gatgaactga ccaggcacta ccgtaaacac acggggcacc gcccgttcca  10080
gtgccaaaaa tgcgaccgag cattttccag gtcggaccac ctcgccttac acatgaagag  10140
gcatttttct agacaatgta ctaactacgc tttgttgaaa ctcgctggcg atgttgaaag  10200
taaccccggt cctggcgcgc ccatgtacaa catgatggag acggagctga agccgccggg  10260
cccgcagcaa acttcggggg gcggcggcgg caactccacc gcggcggcgg ccggcggcaa  10320
ccagaaaaac agcccggacc gcgtcaagcg gcccatgaat gccttcatgg tgtggtcccg  10380
cgggcagcgg cgcaagatgg cccaggagaa ccccaagatg cacaactcgg agatcagcaa  10440
gcgcctgggc gccgagtgga aacttttgtc ggagacggag aagcggccgt tcatcgacga  10500
ggctaagcgg ctgcgagcgc tgcacatgaa ggagcacccg gattataaat accggccccg  10560
gcggaaaacc aagacgctca tgaagaagga taagtacacg ctgcccggcg ggctgctggc  10620
ccccggcggc aatagcatgg cgagcggggt cggggtgggc gccggcctgg gcgcgggcgt  10680
gaaccagcgc atggacagtt acgcgcacat gaacggctgg agcaacggca gctacagcat  10740
gatgcaggac cagctgggct acccgcagca cccgggcctc aatgcgcacg gcgcagcgca  10800
gatgcagccc atgcaccgct acgacgtgag cgccctgcag tacaactcca tgaccagctc  10860
gcagacctac atgaacggct cgcccaccta cagcatgtcc tactcgcagc agggcacccc  10920
tggcatggct cttggctcca tgggttcggt ggtcaagtcc gaggccagct ccagcccccc  10980
tgtggttacc tcttcctccc actccagggc gccctgccag gccggggacc tccgggacat  11040
gatcagcatg tatctccccg gcgccgaggt gccggaaccc gccgccccca gcagacttca  11100
catgtcccag cactaccaga gcggcccggt gcccggcacg gccattaacg gcacactgcc  11160
cctctcacac atgtgagcgg ccatcgatgt cgacaactaa cttaagctag caacggtttc  11220
cctctagcgg gatcaattcc gcccccccccc cctaacgtta ctggccgaag ccgcttggaa  11280
taaggccggt gtgcgtttgt ctatatgtta ttttccacca tattgccgtc ttttggcaat  11340
gtgagggccc ggaaacctgg ccctgtcttc ttgacgagca ttcctagggg tctttcccct  11400
ctcgccaaag gaatgcaagg tctgttgaat gtcgtgaagg aagcagttcc tctggaagct  11460
tcttgaagac aaacaacgtc tgtagcgacc ctttgcaggc agcggaaccc cccacctggc  11520
gacaggtgcc tctgcggcca aaagccacgt gtataagata cacctgcaaa ggcggcacaa  11580
ccccagtgcc acgttgtgag ttggatagtt gtggaaagag tcaaatggct ctcctcaagc  11640
gtattcaaca aggggctgaa ggatgcccag aaggtacccc attgtatggg atctgatctg  11700
```

```
gggcctcggt gcacatgctt tacatgtgtt tagtcgaggt taaaaaaacg tctaggcccc  11760
ccgaaccacg gggacgtggt tttcctttga aaaacacgat aataccaatt cgccaccatg  11820
gcagaggccc gcacatccct gtctgcccac tgtcggggcc cgctggccac tggcctgcac  11880
ccagacctgg acctcccggg ccgaagcctc gccacccctg cgccttcctg ctaccttctg  11940
ggcagcgaac ccagctctgg cctgggcctc cagcccgaga cccacctccc cgagggcagc  12000
ctgaagcggt gctgcgtctt gggcctaccc cccacctccc cagcctcctc ctcaccctgt  12060
gcctcctccg acgtcacctc catcatccgc tcctcccaga cgtctctggt cacctgtgta  12120
aatggactcc ggagcccccc tctgacggga gatctggggg gcccttccaa gcgggcccgg  12180
cctggccctg catcgacgga cagccatgag ggcagcttgc aacttgaagc ctgccggaag  12240
gcgagcttcc tgaagcagga acccgcggat gagttttcag agctctttgg gcctcaccag  12300
cagggcctgc cgccccccta tcccctgtct cagttgccgc ctggcccaag ccttggaggc  12360
ctggggctgg gcctggcagg cagggtggtg gccgggcggc aggcgtgccg ctgggtggac  12420
tgctgtgcag cctatgagca gcaggaggag ctggtgcggc acatcgagaa gagccacatc  12480
gaccagcgca agggcgagga cttcacctgc ttctgggctg gctgcgtgcg ccgctacaag  12540
cccttcaacg cccgctacaa gctgctcatc cacatgcgag tgcactcggg cgagaagccc  12600
aacaagtgca tgtttgaagg ctgcagcaag gccttctcac ggctggagaa cctcaagatc  12660
cacctgagga gccacacggg cgagaagccg tacctgtgcc agcacccggg ttgccagaag  12720
gccttcagca actccagcga ccgcgccaag caccagcgca cccacctaga cacgaagccg  12780
tacgcctgtc agatccctgg ctgctccaag cgctacacag accccagctc cctccgcaag  12840
cacgtcaagg cccattcagc caaagagcag caggtgcgta agaagctgca tgcgggccct  12900
gacaccgagg ccgacgtcct gaccgagtgt ctggtcctgc agcagctcca cacgtccaca  12960
cagctggctg ccagcgacgg caagggtggc tgtggcctgg gccaggagct gctcccaggt  13020
gtgtatcctg gctccatcac cccccataac ggacttgcat cgggcctcct gcccccagcg  13080
cacgacgtac cttccaggca ccacccgctg gatgccacca ccagttccca ccaccatctg  13140
tcccctctgc ccatggctga gagcacccgg gatgggttgg ggcccggcct cctctcacca  13200
atagtcagcc ccctgaaggg gctggggcca ccgccgctgc ccccatcctc tcagagccat  13260
tctccggggg gccagccctt ccccacactc cccagcaagc cgtcctaccc acccttccag  13320
agccctccac ccccgcctct gcccagccca caaggttacc agggcagttt ccactccatc  13380
cagagttgct tcccctatgg cgactgctac cggatggctg aaccagcagc cggtggggac  13440
ggactggtcg gggagaccca cggtttcaac cccctgcggc ccaatggcta ccacagcctc  13500
agcacgccct tgcctgccac aggctatgag gccctggctg aggcctcatg ccccacagcg  13560
ctgccacagc agccatctga agatgtggtg tccagcggcc ccgaggactg tggcttcttc  13620
cccaatggag cctttgacca ctgcctgggc cacatcccct ccatctacac agacacctga  13680
gcggccgcaa ctaacttaag ctagcaacgg tttccctcta gcgggatcaa ttccgccccc  13740
ccccccctaac gttactggcc gaagccgctt ggaataaggc cggtgtgcgt ttgtctatat  13800
gttattttcc accatattgc cgtcttttgg caatgtgagg gcccggaaac ctggccctgt  13860
cttcttgacg agcattccta ggggtctttc ccctctcgcc aaaggaatgc aaggtctgtt  13920
gaatgtcgtg aaggaagcag ttcctctgga agcttcttga agacaaacaa cgtctgtagc  13980
gaccctttgc aggcagcgga accccccacc tggcgacagg tgcctctgcg gccaaaagcc  14040
```

-continued

```
acgtgtataa gatacacctg caaaggcggc acaaccccag tgccacgttg tgagttggat  14100
agttgtggaa agagtcaaat ggctctcctc aagcgtattc aacaaggggc tgaaggatgc  14160
ccagaaggta ccccattgta tgggatctga tctggggcct cggtgcacat gctttacatg  14220
tgtttagtcg aggttaaaaa aacgtctagg ccccccgaac cacggggacg tggttttcct  14280
ttgaaaaaca cgataatacc atgaccgagt acaagcccac ggtgcgcctc gccacccgcg  14340
acgacgtccc cagggccgta cgcaccctcg ccgccgcgtt cgccgactac cccgccacgc  14400
gccacaccgt cgatccggac cgccacatcg agcgggtcac cgagctgcaa gaactcttcc  14460
tcacgcgcgt cgggctcgac atcggcaagg tgtgggtcgc ggacgacggc gccgcggtgg  14520
cggtctggac cacgccggag agcgtcgaag cgggggcggt gttcgccgag atcggcccgc  14580
gcatggccga gttgagcggt tcccggctgg ccgcgcagca acagatggaa ggcctcctgg  14640
cgccgcaccg gcccaaggag cccgcgtggt tcctggccac cgtcggcgtc tcgcccgacc  14700
accagggcaa gggtctgggc agcgccgtcg tgctccccgg agtggaggcg gccgagcgcg  14760
ccggggtgcc cgccttcctg gagacctccg cgccccgcaa cctccccttc tacgagcggc  14820
tcggcttcac cgtcaccgcc gacgtcgagg tgcccgaagg accgcgcacc tggtgcatga  14880
cccgcaagcc cggtgcctga gaattggcaa gctgcttaca tagaactcgc ggcgattggc  14940
atgccgcctt aaaattttta ttttattttt cttttctttt ccgaatcgga ttttgttttt  15000
aatatttcaa aaaaaaaaaa aaaaaaaaaa aaaacgcgtc gaggggaatt aattcttgaa  15060
gacgaaaggg ccaggtggca cttttcgggg aaatgtgcgc ggaaccccta tttgtttatt  15120
tttctaaata cattcaaata tgtatccgct catgagacaa taaccctgat aaatgcttca  15180
ataatattga aaaaggaaga gtatgagtat tcaacatttc cgtgtcgccc ttattccctt  15240
ttttgcggca ttttgccttc ctgtttttgc tcacccagaa acgctggtga aagtaaaaga  15300
tgctgaagat cagttgggtg cacgagtggg ttacatcgaa ctggatctca acagcggtaa  15360
gatccttgag agttttcgcc ccgaagaacg ttttccaatg atgagcactt ttaaagttct  15420
gctatgtggc gcggtattat cccgtgttga cgccgggcaa gagcaactcg gtcgccgcat  15480
acactattct cagaatgact tggttgagta ctcaccagtc acagaaaagc atcttacgga  15540
tggcatgaca gtaagagaat tatgcagtgc tgccataacc atgagtgata acactgcggc  15600
caacttactt ctgacaacga tcggaggacc gaaggagcta accgcttttt tgcacaacat  15660
gggggatcat gtaactcgcc ttgatcgttg ggaaccggag ctgaatgaag ccataccaaa  15720
cgacgagcgt gacaccacga tgcctgtagc aatggcaaca acgttgcgca aactattaac  15780
tggcgaacta cttactctag cttcccggca acaattaata gactggatgg aggcggataa  15840
agttgcagga ccacttctgc gctcggccct tccggctggc tggtttattg ctgataaatc  15900
tggagccggt gagcgtgggt ctcgcggtat cattgcagca ctggggccag atggtaagcc  15960
ctcccgtatc gtagttatct acacgacggg gagtcaggca actatggatg aacgaaatag  16020
acagatcgct gagataggtg cctcactgat taagcattgg taactgtcag accaagttta  16080
ctcatatata ctttagattg atttaaaact tcatttttaa tttaaaagga tctaggtgaa  16140
gatccttttt gataatctca tgaccaaaat cccttaacgt gagttttcgt tccactgagc  16200
gtcagacccc gtagaaaaga tcaaaggatc ttcttgagat cctttttttc tgcgcgtaat  16260
ctgctgcttg caaacaaaaa aaccaccgct accagcggtg gtttgtttgc cggatcaaga  16320
gctaccaact ctttttccga aggtaactgg cttcagcaga gcgcagatac caaatactgt  16380
ccttctagtg tagccgtagt taggccacca cttcaagaac tctgtagcac cgcctacata  16440
```

```
cctcgctctg ctaatcctgt taccagtggc tgctgccagt ggcgataagt cgtgtcttac  16500

cgggttggac tcaagacgat agttaccgga taaggcgcag cggtcgggct gaacgggggg  16560

ttcgtgcaca cagcccagct tggagcgaac gacctacacc gaactgagat acctacagcg  16620

tgagcattga gaaagcgcca cgcttcccga agggagaaag gcggacaggt atccggtaag  16680

cggcagggtc ggaacaggag agcgcacgag ggagcttcca gggggaaacg cctggtatct  16740

ttatagtcct gtcgggtttc gccacctctg acttgagcgt cgatttttgt gatgctcgtc  16800

aggggggcgg agcctatgga aaaacgccag caacgcgagc tctaatacga ctcactatag  16860
```

```
<210> SEQ ID NO 33
<211> LENGTH: 1863
<212> TYPE: DNA
<213> ORGANISM: Homo sapiens
<220> FEATURE:
<221> NAME/KEY: CDS
<222> LOCATION: (1)..(1863)

<400> SEQUENCE: 33

atg gca gag gcc cgc aca tcc ctg tct gcc cac tgt cgg ggc ccg ctg       48
Met Ala Glu Ala Arg Thr Ser Leu Ser Ala His Cys Arg Gly Pro Leu
1               5                   10                  15

gcc act ggc ctg cac cca gac ctg gac ctc ccg ggc cga agc ctc gcc       96
Ala Thr Gly Leu His Pro Asp Leu Asp Leu Pro Gly Arg Ser Leu Ala
            20                  25                  30

acc cct gcg cct tcc tgc tac ctt ctg ggc agc gaa ccc agc tct ggc      144
Thr Pro Ala Pro Ser Cys Tyr Leu Leu Gly Ser Glu Pro Ser Ser Gly
        35                  40                  45

ctg ggc ctc cag ccc gag acc cac ctc ccc gag ggc agc ctg aag cgg      192
Leu Gly Leu Gln Pro Glu Thr His Leu Pro Glu Gly Ser Leu Lys Arg
    50                  55                  60

tgc tgc gtc ttg ggc cta ccc ccc acc tcc cca gcc tcc tcc tca ccc      240
Cys Cys Val Leu Gly Leu Pro Pro Thr Ser Pro Ala Ser Ser Ser Pro
65                  70                  75                  80

tgt gcc tcc tcc gac gtc acc tcc atc atc cgc tcc tcc cag acg tct      288
Cys Ala Ser Ser Asp Val Thr Ser Ile Ile Arg Ser Ser Gln Thr Ser
                85                  90                  95

ctg gtc acc tgt gta aat gga ctc cgg agc ccc cct ctg acg gga gat      336
Leu Val Thr Cys Val Asn Gly Leu Arg Ser Pro Pro Leu Thr Gly Asp
            100                 105                 110

ctg ggg ggc cct tcc aag cgg gcc cgg cct ggc cct gca tcg acg gac      384
Leu Gly Gly Pro Ser Lys Arg Ala Arg Pro Gly Pro Ala Ser Thr Asp
        115                 120                 125

agc cat gag ggc agc ttg caa ctt gaa gcc tgc cgg aag gcg agc ttc      432
Ser His Glu Gly Ser Leu Gln Leu Glu Ala Cys Arg Lys Ala Ser Phe
    130                 135                 140

ctg aag cag gaa ccc gcg gat gag ttt tca gag ctc ttt ggg cct cac      480
Leu Lys Gln Glu Pro Ala Asp Glu Phe Ser Glu Leu Phe Gly Pro His
145                 150                 155                 160

cag cag ggc ctg ccg ccc ccc tat ccc ctg tct cag ttg ccg cct ggc      528
Gln Gln Gly Leu Pro Pro Pro Tyr Pro Leu Ser Gln Leu Pro Pro Gly
                165                 170                 175

cca agc ctt gga ggc ctg ggg ctg ggc ctg gca ggc agg gtg gtg gcc      576
Pro Ser Leu Gly Gly Leu Gly Leu Gly Leu Ala Gly Arg Val Val Ala
            180                 185                 190

ggg cgg cag gcg tgc cgc tgg gtg gac tgc tgt gca gcc tat gag cag      624
Gly Arg Gln Ala Cys Arg Trp Val Asp Cys Cys Ala Ala Tyr Glu Gln
        195                 200                 205

cag gag gag ctg gtg cgg cac atc gag aag agc cac atc gac cag cgc      672
```

```
Gln Glu Glu Leu Val Arg His Ile Glu Lys Ser His Ile Asp Gln Arg
    210                 215                 220

aag ggc gag gac ttc acc tgc ttc tgg gct ggc tgc gtg cgc cgc tac      720
Lys Gly Glu Asp Phe Thr Cys Phe Trp Ala Gly Cys Val Arg Arg Tyr
225                 230                 235                 240

aag ccc ttc aac gcc cgc tac aag ctg ctc atc cac atg cga gtg cac      768
Lys Pro Phe Asn Ala Arg Tyr Lys Leu Leu Ile His Met Arg Val His
                245                 250                 255

tcg ggc gag aag ccc aac aag tgc atg ttt gaa ggc tgc agc aag gcc      816
Ser Gly Glu Lys Pro Asn Lys Cys Met Phe Glu Gly Cys Ser Lys Ala
            260                 265                 270

ttc tca cgg ctg gag aac ctc aag atc cac ctg agg agc cac acg ggc      864
Phe Ser Arg Leu Glu Asn Leu Lys Ile His Leu Arg Ser His Thr Gly
        275                 280                 285

gag aag ccg tac ctg tgc cag cac ccg ggt tgc cag aag gcc ttc agc      912
Glu Lys Pro Tyr Leu Cys Gln His Pro Gly Cys Gln Lys Ala Phe Ser
    290                 295                 300

aac tcc agc gac cgc gcc aag cac cag cgc acc cac cta gac acg aag      960
Asn Ser Ser Asp Arg Ala Lys His Gln Arg Thr His Leu Asp Thr Lys
305                 310                 315                 320

ccg tac gcc tgt cag atc cct ggc tgc tcc aag cgc tac aca gac ccc     1008
Pro Tyr Ala Cys Gln Ile Pro Gly Cys Ser Lys Arg Tyr Thr Asp Pro
                325                 330                 335

agc tcc ctc cgc aag cac gtc aag gcc cat tca gcc aaa gag cag cag     1056
Ser Ser Leu Arg Lys His Val Lys Ala His Ser Ala Lys Glu Gln Gln
            340                 345                 350

gtg cgt aag aag ctg cat gcg ggc cct gac acc gag gcc gac gtc ctg     1104
Val Arg Lys Lys Leu His Ala Gly Pro Asp Thr Glu Ala Asp Val Leu
        355                 360                 365

acc gag tgt ctg gtc ctg cag cag ctc cac acg tcc aca cag ctg gct     1152
Thr Glu Cys Leu Val Leu Gln Gln Leu His Thr Ser Thr Gln Leu Ala
    370                 375                 380

gcc agc gac ggc aag ggt ggc tgt ggc ctg ggc cag gag ctg ctc cca     1200
Ala Ser Asp Gly Lys Gly Gly Cys Gly Leu Gly Gln Glu Leu Leu Pro
385                 390                 395                 400

ggt gtg tat cct ggc tcc atc acc ccc cat aac gga ctt gca tcg ggc     1248
Gly Val Tyr Pro Gly Ser Ile Thr Pro His Asn Gly Leu Ala Ser Gly
                405                 410                 415

ctc ctg ccc cca gcg cac gac gta cct tcc agg cac cac ccg ctg gat     1296
Leu Leu Pro Pro Ala His Asp Val Pro Ser Arg His His Pro Leu Asp
            420                 425                 430

gcc acc acc agt tcc cac cac cat ctg tcc cct ctg ccc atg gct gag     1344
Ala Thr Thr Ser Ser His His His Leu Ser Pro Leu Pro Met Ala Glu
        435                 440                 445

agc acc cgg gat ggg ttg ggg ccc ggc ctc ctc tca cca ata gtc agc     1392
Ser Thr Arg Asp Gly Leu Gly Pro Gly Leu Leu Ser Pro Ile Val Ser
    450                 455                 460

ccc ctg aag ggg ctg ggg cca ccg ccg ctg ccc cca tcc tct cag agc     1440
Pro Leu Lys Gly Leu Gly Pro Pro Pro Leu Pro Pro Ser Ser Gln Ser
465                 470                 475                 480

cat tct ccg ggg ggc cag ccc ttc ccc aca ctc ccc agc aag ccg tcc     1488
His Ser Pro Gly Gly Gln Pro Phe Pro Thr Leu Pro Ser Lys Pro Ser
                485                 490                 495

tac cca ccc ttc cag agc cct cca ccc ccg cct ctg ccc agc cca caa     1536
Tyr Pro Pro Phe Gln Ser Pro Pro Pro Pro Pro Leu Pro Ser Pro Gln
            500                 505                 510

ggt tac cag ggc agt ttc cac tcc atc cag agt tgc ttc ccc tat ggc     1584
Gly Tyr Gln Gly Ser Phe His Ser Ile Gln Ser Cys Phe Pro Tyr Gly
        515                 520                 525
```

```
gac tgc tac cgg atg gct gaa cca gca gcc ggt ggg gac gga ctg gtc     1632
Asp Cys Tyr Arg Met Ala Glu Pro Ala Ala Gly Gly Asp Gly Leu Val
    530                 535                 540

ggg gag acc cac ggt ttc aac ccc ctg cgg ccc aat ggc tac cac agc     1680
Gly Glu Thr His Gly Phe Asn Pro Leu Arg Pro Asn Gly Tyr His Ser
545                 550                 555                 560

ctc agc acg ccc ttg cct gcc aca ggc tat gag gcc ctg gct gag gcc     1728
Leu Ser Thr Pro Leu Pro Ala Thr Gly Tyr Glu Ala Leu Ala Glu Ala
                565                 570                 575

tca tgc ccc aca gcg ctg cca cag cag cca tct gaa gat gtg gtg tcc     1776
Ser Cys Pro Thr Ala Leu Pro Gln Gln Pro Ser Glu Asp Val Val Ser
            580                 585                 590

agc ggc ccc gag gac tgt ggc ttc ttc ccc aat gga gcc ttt gac cac     1824
Ser Gly Pro Glu Asp Cys Gly Phe Phe Pro Asn Gly Ala Phe Asp His
        595                 600                 605

tgc ctg ggc cac atc ccc tcc atc tac aca gac acc tga                 1863
Cys Leu Gly His Ile Pro Ser Ile Tyr Thr Asp Thr
    610                 615                 620


<210> SEQ ID NO 34
<211> LENGTH: 620
<212> TYPE: PRT
<213> ORGANISM: Homo sapiens

<400> SEQUENCE: 34

Met Ala Glu Ala Arg Thr Ser Leu Ser Ala His Cys Arg Gly Pro Leu
1               5                   10                  15

Ala Thr Gly Leu His Pro Asp Leu Asp Leu Pro Gly Arg Ser Leu Ala
            20                  25                  30

Thr Pro Ala Pro Ser Cys Tyr Leu Leu Gly Ser Glu Pro Ser Ser Gly
        35                  40                  45

Leu Gly Leu Gln Pro Glu Thr His Leu Pro Glu Gly Ser Leu Lys Arg
    50                  55                  60

Cys Cys Val Leu Gly Leu Pro Pro Thr Ser Pro Ala Ser Ser Ser Pro
65                  70                  75                  80

Cys Ala Ser Ser Asp Val Thr Ser Ile Ile Arg Ser Ser Gln Thr Ser
                85                  90                  95

Leu Val Thr Cys Val Asn Gly Leu Arg Ser Pro Pro Leu Thr Gly Asp
            100                 105                 110

Leu Gly Gly Pro Ser Lys Arg Ala Arg Pro Gly Pro Ala Ser Thr Asp
        115                 120                 125

Ser His Glu Gly Ser Leu Gln Leu Glu Ala Cys Arg Lys Ala Ser Phe
    130                 135                 140

Leu Lys Gln Glu Pro Ala Asp Glu Phe Ser Glu Leu Phe Gly Pro His
145                 150                 155                 160

Gln Gln Gly Leu Pro Pro Pro Tyr Pro Leu Ser Gln Leu Pro Pro Gly
                165                 170                 175

Pro Ser Leu Gly Gly Leu Gly Leu Gly Leu Ala Gly Arg Val Val Ala
            180                 185                 190

Gly Arg Gln Ala Cys Arg Trp Val Asp Cys Cys Ala Ala Tyr Glu Gln
        195                 200                 205

Gln Glu Glu Leu Val Arg His Ile Glu Lys Ser His Ile Asp Gln Arg
    210                 215                 220

Lys Gly Glu Asp Phe Thr Cys Phe Trp Ala Gly Cys Val Arg Arg Tyr
225                 230                 235                 240

Lys Pro Phe Asn Ala Arg Tyr Lys Leu Leu Ile His Met Arg Val His
                245                 250                 255
```

```
Ser Gly Glu Lys Pro Asn Lys Cys Met Phe Glu Gly Cys Ser Lys Ala
            260                 265                 270

Phe Ser Arg Leu Glu Asn Leu Lys Ile His Leu Arg Ser His Thr Gly
        275                 280                 285

Glu Lys Pro Tyr Leu Cys Gln His Pro Gly Cys Gln Lys Ala Phe Ser
    290                 295                 300

Asn Ser Ser Asp Arg Ala Lys His Gln Arg Thr His Leu Asp Thr Lys
305                 310                 315                 320

Pro Tyr Ala Cys Gln Ile Pro Gly Cys Ser Lys Arg Tyr Thr Asp Pro
                325                 330                 335

Ser Ser Leu Arg Lys His Val Lys Ala His Ser Ala Lys Glu Gln Gln
            340                 345                 350

Val Arg Lys Lys Leu His Ala Gly Pro Asp Thr Glu Ala Asp Val Leu
        355                 360                 365

Thr Glu Cys Leu Val Leu Gln Gln Leu His Thr Ser Thr Gln Leu Ala
    370                 375                 380

Ala Ser Asp Gly Lys Gly Gly Cys Gly Leu Gly Gln Glu Leu Leu Pro
385                 390                 395                 400

Gly Val Tyr Pro Gly Ser Ile Thr Pro His Asn Gly Leu Ala Ser Gly
                405                 410                 415

Leu Leu Pro Pro Ala His Asp Val Pro Ser Arg His His Pro Leu Asp
            420                 425                 430

Ala Thr Thr Ser Ser His His His Leu Ser Pro Leu Pro Met Ala Glu
        435                 440                 445

Ser Thr Arg Asp Gly Leu Gly Pro Gly Leu Leu Ser Pro Ile Val Ser
    450                 455                 460

Pro Leu Lys Gly Leu Gly Pro Pro Pro Leu Pro Pro Ser Ser Gln Ser
465                 470                 475                 480

His Ser Pro Gly Gly Gln Pro Phe Pro Thr Leu Pro Ser Lys Pro Ser
                485                 490                 495

Tyr Pro Pro Phe Gln Ser Pro Pro Pro Pro Pro Leu Pro Ser Pro Gln
            500                 505                 510

Gly Tyr Gln Gly Ser Phe His Ser Ile Gln Ser Cys Phe Pro Tyr Gly
        515                 520                 525

Asp Cys Tyr Arg Met Ala Glu Pro Ala Ala Gly Gly Asp Gly Leu Val
    530                 535                 540

Gly Glu Thr His Gly Phe Asn Pro Leu Arg Pro Asn Gly Tyr His Ser
545                 550                 555                 560

Leu Ser Thr Pro Leu Pro Ala Thr Gly Tyr Glu Ala Leu Ala Glu Ala
                565                 570                 575

Ser Cys Pro Thr Ala Leu Pro Gln Gln Pro Ser Glu Asp Val Val Ser
            580                 585                 590

Ser Gly Pro Glu Asp Cys Gly Phe Phe Pro Asn Gly Ala Phe Asp His
        595                 600                 605

Cys Leu Gly His Ile Pro Ser Ile Tyr Thr Asp Thr
    610                 615                 620
```

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide primer - hKlfGC2For

<400> SEQUENCE: 35

```
gcaggaggcg gtctcttcgt gcacc                                          25


<210> SEQ ID NO 36
<211> LENGTH: 25
<212> TYPE: DNA
<213> ORGANISM: Artificial Sequence
<220> FEATURE:
<223> OTHER INFORMATION: Oligonucleotide primer - hKlf4GC2Rev

<400> SEQUENCE: 36

caggtgtgcc ttgagatggg aactc                                          25


<210> SEQ ID NO 37
<211> LENGTH: 58
<212> TYPE: DNA
<213> ORGANISM: Artificial Sequence
<220> FEATURE:
<223> OTHER INFORMATION: Oligonucleotide primer - EcoR1-Sac1-T7M1-VEE

<400> SEQUENCE: 37

cggaattcga gctctaatac gactcactat agatgggcgg cgcatgagag aagcccag      58


<210> SEQ ID NO 38
<211> LENGTH: 38
<212> TYPE: DNA
<213> ORGANISM: Artificial Sequence
<220> FEATURE:
<223> OTHER INFORMATION: Oligonucleotide primer - Xba1-BstZ17I-VEE

<400> SEQUENCE: 38

gctctagagt atacatcctg gtaaacagcg acttgccc                            38


<210> SEQ ID NO 39
<211> LENGTH: 1056
<212> TYPE: DNA
<213> ORGANISM: Vaccinia virus
<220> FEATURE:
<221> NAME/KEY: CDS
<222> LOCATION: (1)..(1056)

<400> SEQUENCE: 39

atg acg atg aaa atg atg gta cat ata tat ttc gta tca tta ttg tta      48
Met Thr Met Lys Met Met Val His Ile Tyr Phe Val Ser Leu Leu Leu
1               5                   10                  15

ttg cta ttc cac agt tac gcc ata gac atc gaa aat gaa atc aca gaa      96
Leu Leu Phe His Ser Tyr Ala Ile Asp Ile Glu Asn Glu Ile Thr Glu
            20                  25                  30

ttc ttc aat aaa atg aga gat act cta cca gct aaa gac tct aaa tgg     144
Phe Phe Asn Lys Met Arg Asp Thr Leu Pro Ala Lys Asp Ser Lys Trp
        35                  40                  45

ttg aat cca gca tgt atg ttc gga ggc aca atg aat gat ata gcc gct     192
Leu Asn Pro Ala Cys Met Phe Gly Gly Thr Met Asn Asp Ile Ala Ala
    50                  55                  60

cta gga gag cca ttc agc gca aag tgt cct cct att gaa gac agt ctt     240
Leu Gly Glu Pro Phe Ser Ala Lys Cys Pro Pro Ile Glu Asp Ser Leu
65                  70                  75                  80

tta tcg cac aga tat aaa gac tat gtg gtt aaa tgg gaa agg cta gaa     288
Leu Ser His Arg Tyr Lys Asp Tyr Val Val Lys Trp Glu Arg Leu Glu
                85                  90                  95

aaa aat aga cgg cga cag gtt tct aat aaa cgt gtt aaa cat ggt gat     336
Lys Asn Arg Arg Arg Gln Val Ser Asn Lys Arg Val Lys His Gly Asp
            100                 105                 110

tta tgg ata gcc aac tat aca tct aaa ttc agt aac cgt agg tat ttg     384
```

```
Leu Trp Ile Ala Asn Tyr Thr Ser Lys Phe Ser Asn Arg Arg Tyr Leu
        115                 120                 125

tgc acc gta act aca aag aat ggt gac tgt gtt cag ggt ata gtt aga      432
Cys Thr Val Thr Thr Lys Asn Gly Asp Cys Val Gln Gly Ile Val Arg
    130                 135                 140

tct cat att aga aaa cct cct tca tgc att cca aaa aca tat gaa cta      480
Ser His Ile Arg Lys Pro Pro Ser Cys Ile Pro Lys Thr Tyr Glu Leu
145                 150                 155                 160

ggt act cat gat aag tat ggc ata gac tta tac tgt gga att ctt tac      528
Gly Thr His Asp Lys Tyr Gly Ile Asp Leu Tyr Cys Gly Ile Leu Tyr
                165                 170                 175

gca aaa cat tat aat aat ata act tgg tat aaa gat aat aag gaa att      576
Ala Lys His Tyr Asn Asn Ile Thr Trp Tyr Lys Asp Asn Lys Glu Ile
            180                 185                 190

aat atc gac gac att aag tat tca caa acg gga aag gaa tta att att      624
Asn Ile Asp Asp Ile Lys Tyr Ser Gln Thr Gly Lys Glu Leu Ile Ile
        195                 200                 205

cat aat cca gag tta gaa gat agc gga aga tac gac tgt tac gtt cat      672
His Asn Pro Glu Leu Glu Asp Ser Gly Arg Tyr Asp Cys Tyr Val His
    210                 215                 220

tac gac gac gtt aga atc aag aat gat atc gta gta tca aga tgt aaa      720
Tyr Asp Asp Val Arg Ile Lys Asn Asp Ile Val Val Ser Arg Cys Lys
225                 230                 235                 240

ata ctt acg gtt ata ccg tca caa gac cac agg ttt aaa cta ata cta      768
Ile Leu Thr Val Ile Pro Ser Gln Asp His Arg Phe Lys Leu Ile Leu
                245                 250                 255

gat cca aaa atc aac gta acg ata gga gaa cct gcc aat ata aca tgc      816
Asp Pro Lys Ile Asn Val Thr Ile Gly Glu Pro Ala Asn Ile Thr Cys
            260                 265                 270

act gct gtg tca acg tca tta ttg att gac gat gta ctg att gaa tgg      864
Thr Ala Val Ser Thr Ser Leu Leu Ile Asp Asp Val Leu Ile Glu Trp
        275                 280                 285

gaa aat cca tcc gga tgg ctt ata gga ttc gat ttt gat gta tac tct      912
Glu Asn Pro Ser Gly Trp Leu Ile Gly Phe Asp Phe Asp Val Tyr Ser
    290                 295                 300

gtt tta act agt aga ggc ggt att acc gag gcg acc ttg tac ttt gaa      960
Val Leu Thr Ser Arg Gly Gly Ile Thr Glu Ala Thr Leu Tyr Phe Glu
305                 310                 315                 320

aat gtt act gaa gaa tat ata ggt aat aca tat aaa tgt cgt gga cac     1008
Asn Val Thr Glu Glu Tyr Ile Gly Asn Thr Tyr Lys Cys Arg Gly His
                325                 330                 335

aac tat tat ttt gaa aaa acc ctt aca act aca gta gta ttg gag taa     1056
Asn Tyr Tyr Phe Glu Lys Thr Leu Thr Thr Thr Val Val Leu Glu
            340                 345                 350


<210> SEQ ID NO 40
<211> LENGTH: 351
<212> TYPE: PRT
<213> ORGANISM: Vaccinia virus

<400> SEQUENCE: 40

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60
```

-continued

```
Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
        195                 200                 205

His Asn Pro Glu Leu Glu Asp Ser Gly Arg Tyr Asp Cys Tyr Val His
    210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
            260                 265                 270

Thr Ala Val Ser Thr Ser Leu Leu Ile Asp Asp Val Leu Ile Glu Trp
        275                 280                 285

Glu Asn Pro Ser Gly Trp Leu Ile Gly Phe Asp Phe Asp Val Tyr Ser
    290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
            340                 345                 350
```